US011458213B2

(12) United States Patent
Ray et al.

(10) Patent No.: US 11,458,213 B2
(45) Date of Patent: Oct. 4, 2022

(54) PROSTATE-SPECIFIC MEMBRANE ANTIGEN TARGETED HIGH-AFFINITY AGENTS FOR ENDORADIOTHERAPY OF PROSTATE CANCER

(71) Applicant: THE JOHNS HOPKINS UNIVERSITY, Baltimore, MD (US)

(72) Inventors: Sangeeta Ray, Ellicott City, MD (US); Martin G. Pomper, Baltimore, MD (US)

(*) Notice: Subject to any disclaimer, the term of this patent is extended or adjusted under 35 U.S.C. 154(b) by 54 days.

(21) Appl. No.: 16/087,395

(22) PCT Filed: Mar. 22, 2017

(86) PCT No.: PCT/US2017/023508
§ 371 (c)(1),
(2) Date: Sep. 21, 2018

(87) PCT Pub. No.: WO2017/165473
PCT Pub. Date: Sep. 28, 2017

(65) Prior Publication Data
US 2020/0155713 A1    May 21, 2020

Related U.S. Application Data

(60) Provisional application No. 62/311,697, filed on Mar. 22, 2016.

(51) Int. Cl.
*A61K 51/04* (2006.01)
*A61P 35/00* (2006.01)
*C07D 257/02* (2006.01)
*C07D 401/12* (2006.01)

(52) U.S. Cl.
CPC .......... *A61K 51/0482* (2013.01); *A61P 35/00* (2018.01); *C07D 257/02* (2013.01); *C07D 401/12* (2013.01)

(58) Field of Classification Search
CPC ............ A61K 51/0497; A61K 51/0482; A61K 51/0402; C07D 401/12; C07D 257/02; C07B 59/004; A61P 13/08; A61P 35/00
See application file for complete search history.

(56) References Cited

U.S. PATENT DOCUMENTS

| 8,211,401 | B2 | 7/2012 | Babich et al. | |
| 9,044,468 | B2* | 6/2015 | Pomper | A61K 31/145 |
| 9,056,841 | B2* | 6/2015 | Pomper | C07D 209/12 |
| 9,371,360 | B2* | 6/2016 | Pomper | C07K 5/0815 |
| 9,694,091 | B2* | 7/2017 | Pomper | A61K 51/0406 |
| 9,884,132 | B2* | 2/2018 | Pomper | A61K 38/06 |
| 2013/0034494 | A1 | 2/2013 | Babich et al. | |
| 2014/0255306 | A1 | 9/2014 | Babich et al. | |
| 2018/0273441 | A1* | 9/2018 | Musthakahmed | C07B 59/008 |

FOREIGN PATENT DOCUMENTS

| EP | 2862857 | 4/2015 |
| RU | 2532912 | 11/2014 |
| WO | 2009-002529 A2 | 12/2008 |
| WO | WO 2009/002529 | 12/2008 |
| WO | 2009-070302 A1 | 6/2009 |
| WO | WO 2009/070302 | 6/2009 |
| WO | 2010-108125 A2 | 9/2010 |
| WO | WO 2010/108125 | 9/2010 |
| WO | 2015-055318 A1 | 4/2015 |
| WO | WO 2015/055318 | 4/2015 |
| WO | 2015-171792 A1 | 11/2015 |
| WO | WO 2015/171792 | 11/2015 |
| WO | WO 2017/116994 | 7/2017 |

OTHER PUBLICATIONS

International Search Report and Written Opinion dated Jul. 4, 2017, from related PCT Patent Application No. PCT/US2017/023508.
Banerjee S. R., et al., "Preclinical evaluation of 86Y-labeled inhibitors of prostate-specific membrane antigen for dosimetry estimates," Journal of Nuclear Medicine, 2015, 56, 628-34.
Benesova, M., et al., "Preclinical Evaluation of a Tailor-Made DOTA-Conjugated PSMA Inhibitor with Optimized Linker Moiety for Imaging and Endoradiotherapy of Prostate Cancer," Journal of Nuclear Medicine, 2015, 56, 914-20.
Weineisen, M., et al., "Synthesis and preclinical evaluation of DOTAGA-conjugated PSMA ligands for functional imaging and endoradiotherapy of prostate cancer," EJNMMI Res, 2014, 4, 1-15.
Banerjee et al., Preclinical evaluation of 86Y-labeled inhibitors of prostate-specific membrane antigen for dosimetry estimates. J Nucl Med. Apr. 2015;56(4):628-34.
Benesova et al., Preclinical Evaluation of a Tailor-Made DOTA-Conjugated PSMA Inhibitor with Optimized Linker Moiety for Imaging and Endoradiotherapy of Prostate Cancer. J Nucl Med. Jun. 2015;56(6):914-20.
Benesova et al., Linker Modification Strategies to Control the Prostate-Specific Membrane Antigen (PSMA)-Targeting and Pharmacokinetic Properties of DOTA-Conjugated PSMA Inhibitors. J Med Chem. Mar. 10, 2016;59(5):1761-75.
Eder et al., 68Ga-complex lipophilicity and the targeting property of a urea-based PSMA inhibitor for PET imaging. Bioconjug Chem. Apr. 18, 2012;23(4):688-97.
Sacha et al., iBodies: Modular Synthetic Antibody Mimetics Based on Hydrophilic Polymers Decorated with Functional Moieties. Angew Chem Int Ed Engl. Feb. 12, 2016;55(7):2356-60.
Tykvart et al., Rational design of urea-based glutamate carboxypeptidase II (GCPII) inhibitors as versatile tools for specific drug targeting and delivery. Bioorg Med Chem. Aug. 1, 2014;22(15):4099-108.
Tykvart et al., Design of Highly Potent Urea-Based, Exosite-Binding Inhibitors Selective for Glutamate Carboxypeptidase II. J Med Chem. May 28, 2015;58(10):4357-63.

(Continued)

*Primary Examiner* — Michael G. Hartley
*Assistant Examiner* — Leah H Schlientz
(74) *Attorney, Agent, or Firm* — Casimir Jones, S.C.; Jeffrey W. Childers

(57) ABSTRACT

Prostate-specific membrane antigen targeted high-affinity agents for endoradiotherapy of prostate cancer are disclosed.

14 Claims, 6 Drawing Sheets
(5 of 6 Drawing Sheet(s) Filed in Color)

(56) References Cited

OTHER PUBLICATIONS

Weineisen et al., (2014) Synthesis and preclinical evaluation of DOTAGA-conjugated PSMA ligands for functional imaging and endoradiotherapy of prostate cancer. EJNMMI Res. Dec. 2014;4(1):63.
International Search Report and Written Opinion for PCT/US2017/023508, dated Jul. 4, 2017, 16 pages.
Extended EP Search Report for EP 17771028.2, dated Aug. 14, 2019, 11 pages.

* cited by examiner

PROSTATE-SPECIFIC MEMBRANE ANTIGEN TARGETED HIGH-AFFINITY AGENTS FOR ENDORADIOTHERAPY OF PROSTATE CANCER

CROSS-REFERENCE TO RELATED APPLICATIONS

This application is a 35 U.S.C. § 371 National Stage Entry of International Application No. PCT/US2017/023508 having an international filing date of Mar. 22, 2017, which claims the benefit of U.S. Provisional Application No. 62/311,697, filed Mar. 22, 2016, the contents of which are incorporated herein by reference in their entirety.

FEDERALLY SPONSORED RESEARCH OR DEVELOPMENT

This invention was made with government support under CA148901 and CA134675 awarded by the National Institutes of Health. The government has certain rights in the invention.

BACKGROUND

Prostate cancer is the leading cancer in the U.S. population and the second leading cause of cancer death in men. Therapy for locally advanced disease remains contentious and an increasing number of disparate options are available. New, high-affinity, radiotherapeutic agents for prostate cancer have been developed using the prostate-specific membrane antigen (PSMA) as a target. PSMA is a marker for androgen-independent disease that also is expressed on solid (nonprostate) tumor neovasculature.

SUMMARY

In some aspects, the presently disclosed subject matter provides a compound of Formula (I):

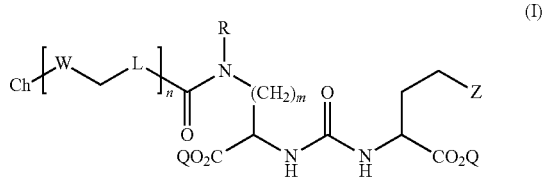

(I)

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ is selected from the group consisting of substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1, 2, and 3; Ch is a chelating agent that can comprise a metal or a radiometal; and pharmaceutically acceptable salts thereof.

In particular aspects of the compound of the Formula (I), $R^1$ is selected from the group consisting of:

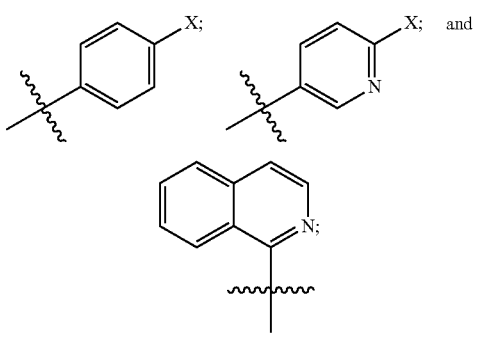

wherein X is independently Br or I.

In yet more particular aspects of the compound of the Formula (I), the chelating agent is selected from the group consisting of:

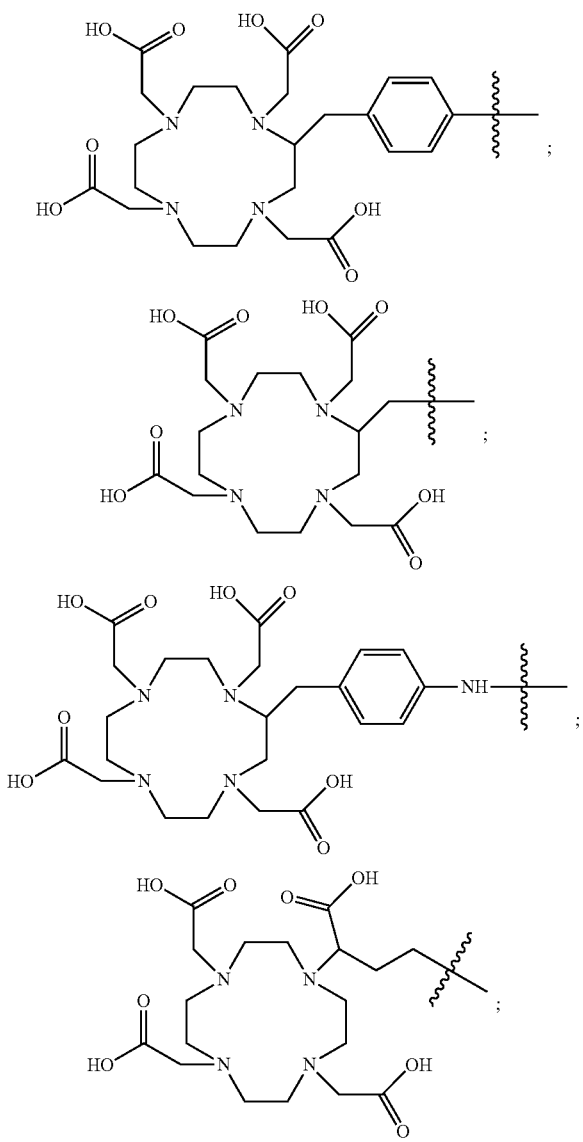

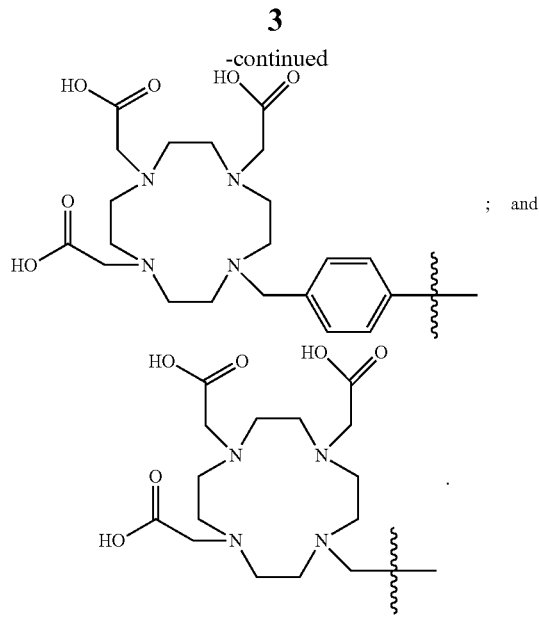

In other aspects, the presently disclosed subject matter provides a method for treating one or more PSMA expressing tumors or cells, the method comprising contacting the one or more PSMA expressing tumors or cells with an effective amount of a compound of formula (I), the compound of formula (I) comprising:

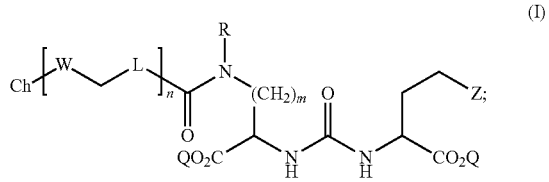

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1, 2, and 3; Ch is a chelating agent that comprises a radiometal suitable for radiotherapy; and pharmaceutically acceptable salts thereof.

In other aspects, the presently disclosed subject matter provides a method for imaging one or more prostate-specific membrane antigen (PSMA) tumors or cells, the method comprising contacting the one or more tumor or cells, with an effective amount of a compound of Formula (I) and making an image.

In yet other aspects, the presently disclosed subject matter provides a kit comprising a compound of Formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1:
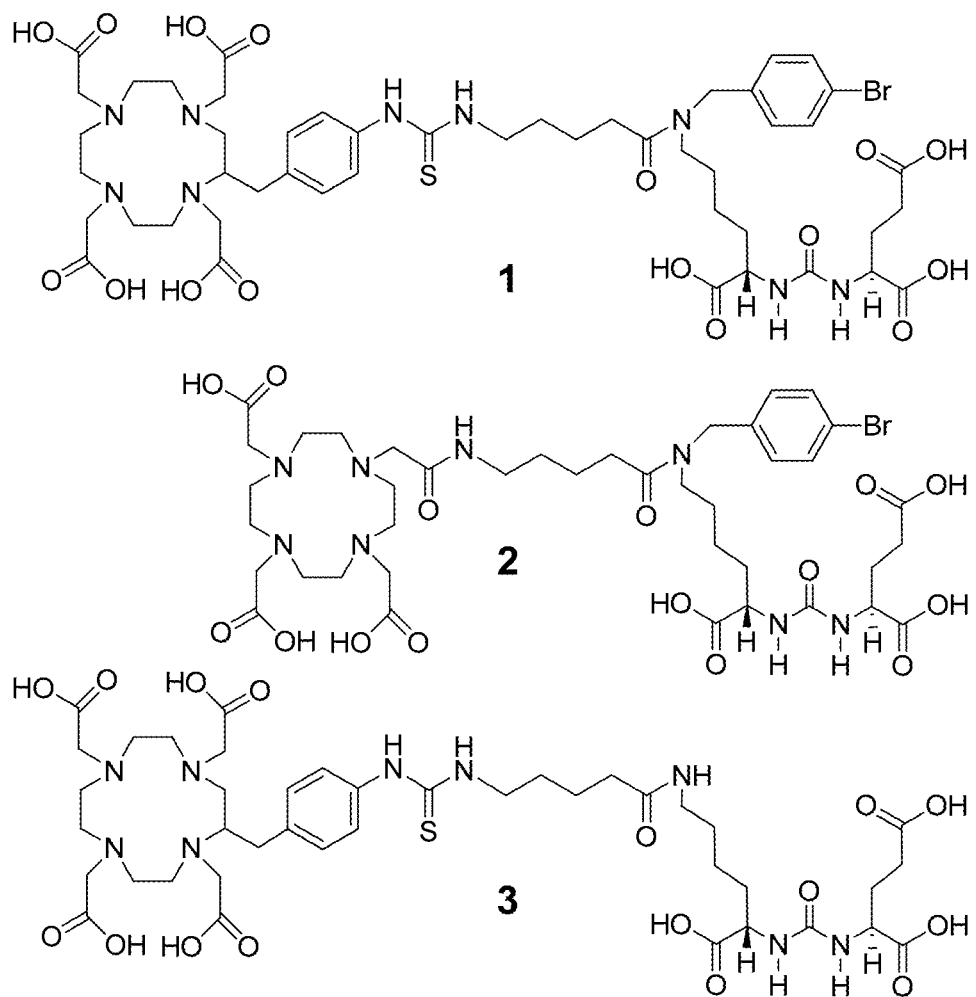
Figure 2:
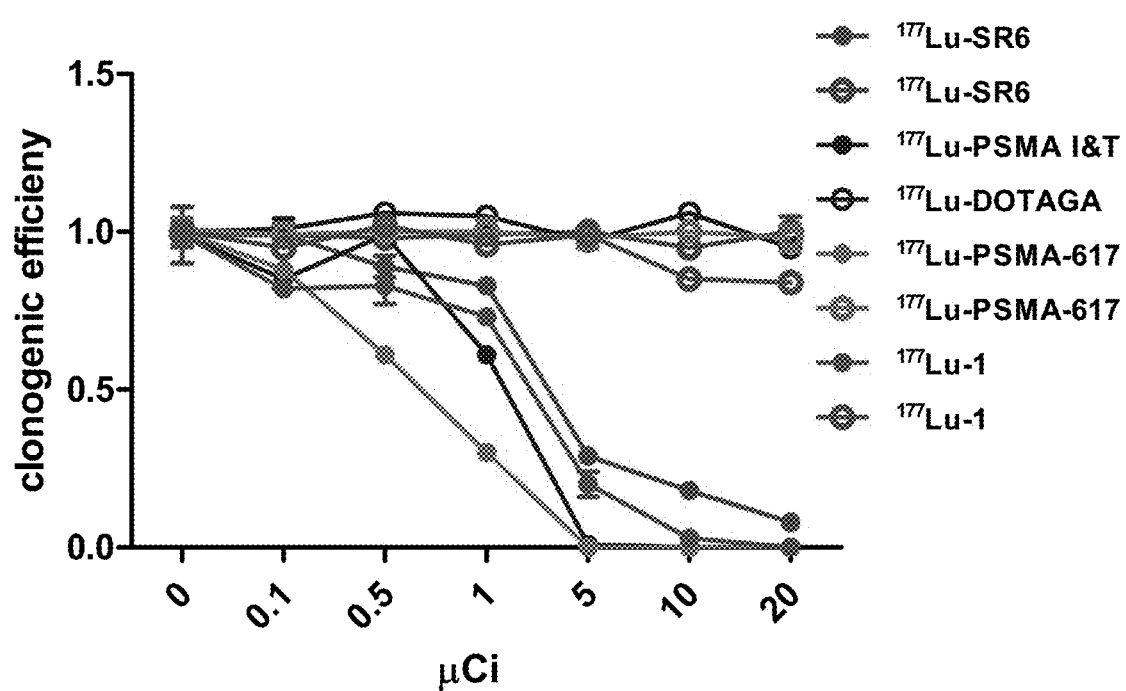
Figure 3:
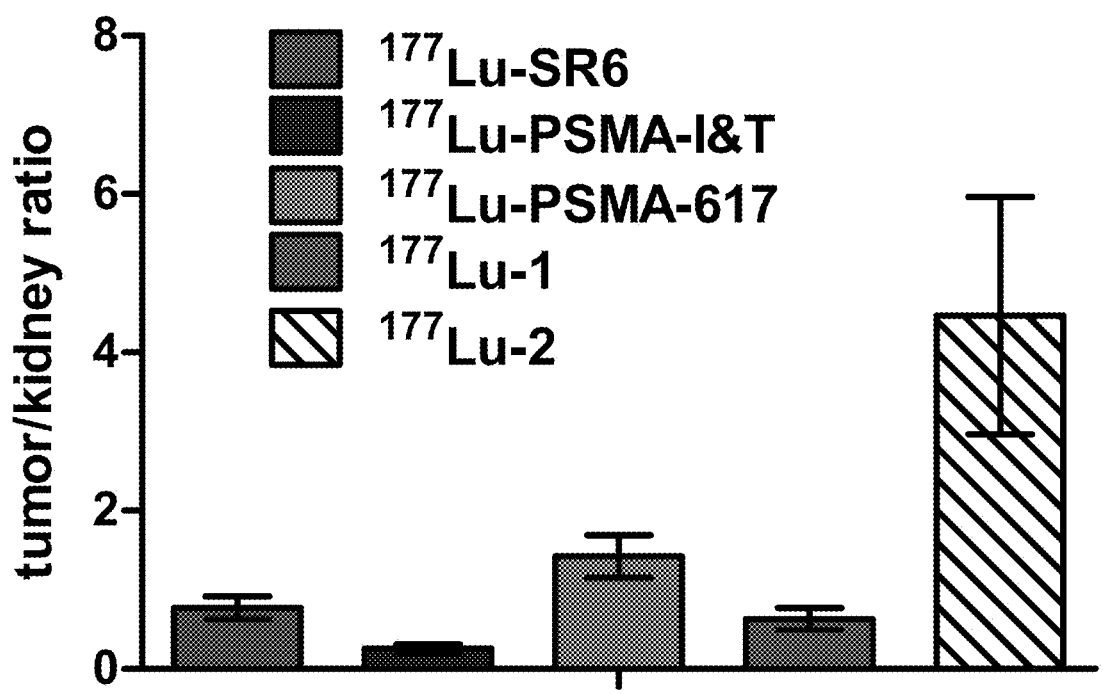
Figure 4:
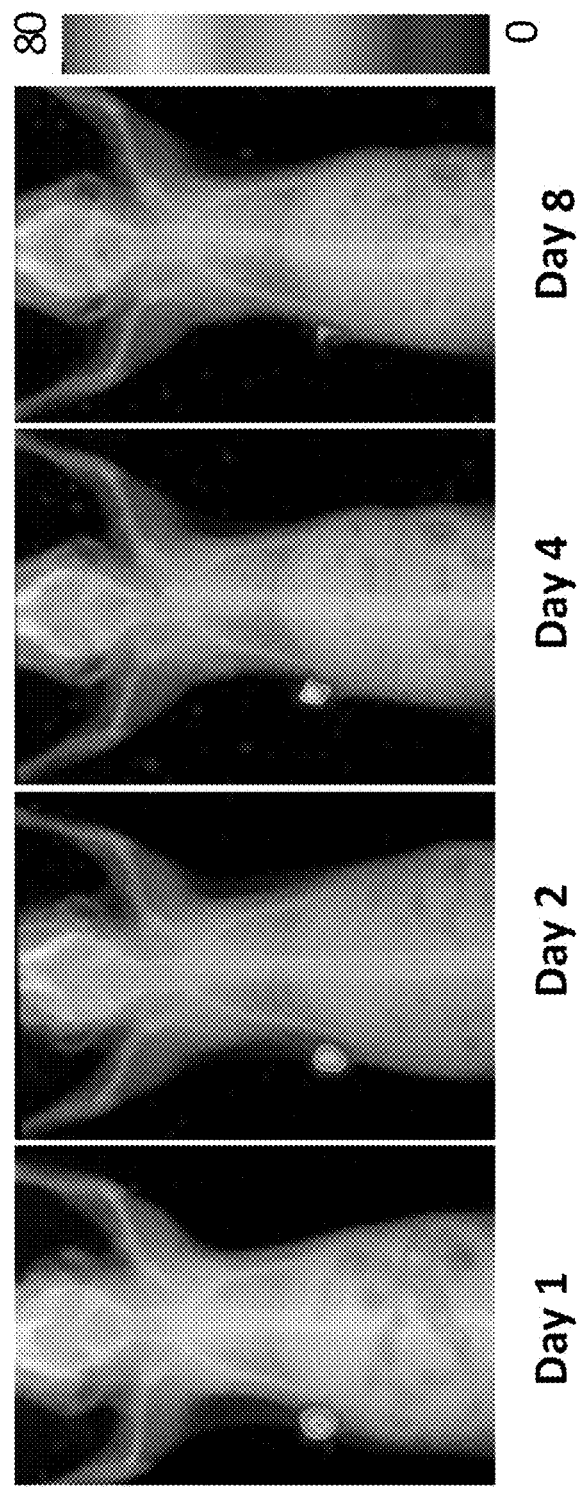
Figure 5:
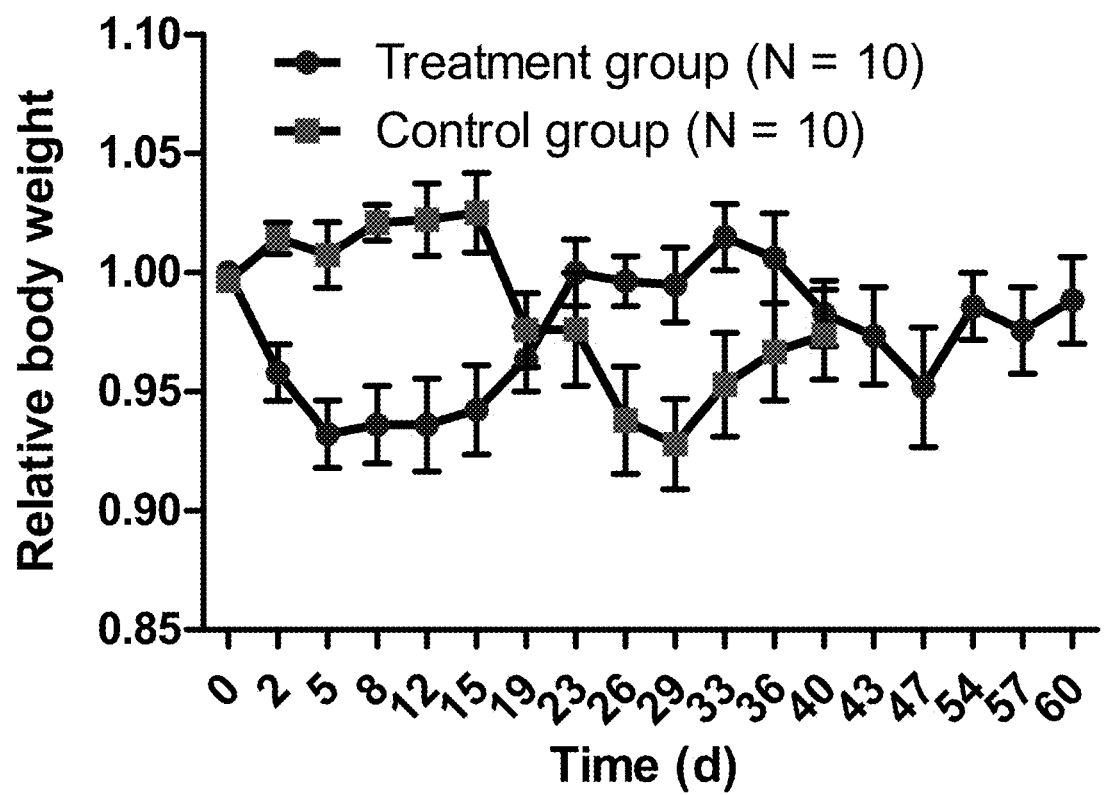
Figure 6A:
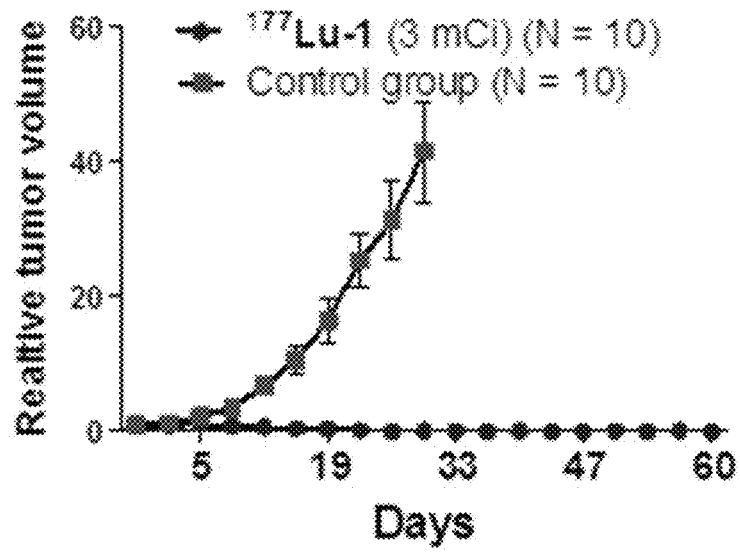
Figure 6B:
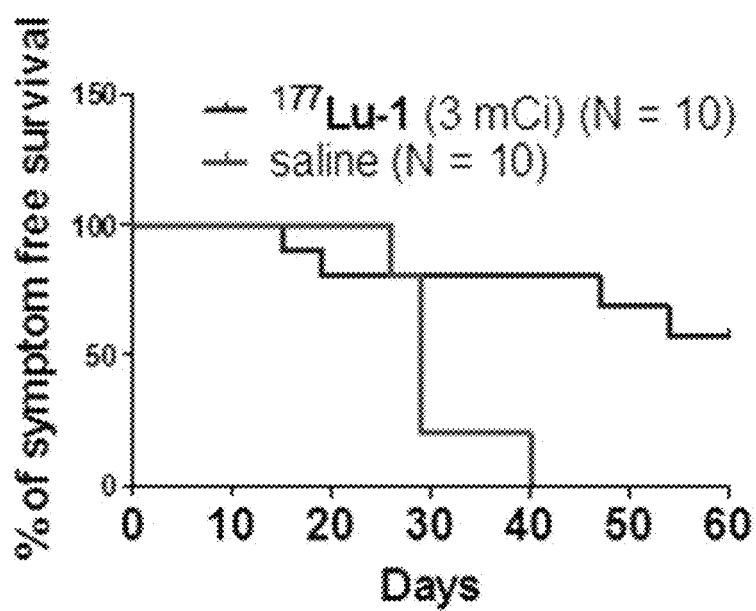

Having thus described the presently disclosed subject matter in general terms, reference will now be made to the accompanying Figures, which are not necessarily drawn to scale, and wherein:

FIG. 1 shows chemical structures of representative radiotherapeutic agents;

FIG. 2 shows a comparative study of the clonogenic efficacy of $^{177}$Lu-1, and known agents SR6, PSMA-617 and PSMA-I&T;

FIG. 3 shows PSMA+ tumor-to-kidney ratios of $^{177}$Lu-1, $^{177}$Lu-2, $^{177}$Lu-SR6, $^{177}$Lu-PSMA-617 and $^{177}$Lu-PSMA-I&T;

FIG. 4 shows SPECT-CT imaging of $^{177}$Lu-1 during treatment studies using of a single dose of 3 mCi;

FIG. 5 shows the relative body weight of the mice during the treatment studies; and FIG. 6A and FIG. 6B show the relative tumor volume of the mice (FIG. 6A) during the treatment studies and the Kaplan-Meier survival curve (FIG. 6B) up to 60 days post-treatment.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Prostate-Specific Membrane Antigen Targeted High-Affinity Agents for Endoradiotherapy of Prostate Cancer A. Compounds of Formula (I)

Accordingly, in some embodiments, the presently disclosed subject matter provides a compound of Formula (I):

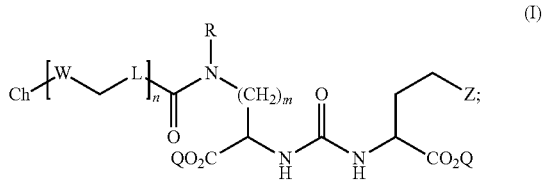

wherein: Z is tetrazole or CO$_2$Q; Q is H or a protecting group; m is an integer selected from the group consisting of 1, 2, 3, 4, and 5; R is independently H or —CH$_2$—R$^1$; R$^1$ is selected from the group consisting of substituted aryl, substituted pyridine, and unsubstituted isoquinoline; L is a linker selected from the group consisting of C$_1$-C$_6$ alkylene and C$_3$-C$_6$ cycloalkylene, and arylene; W is selected from the group consisting of —NR$^2$—(C=O)—, —NR$^2$—(C=S)—, —(C=O)—NR$^2$—, and —(C=S)—NR$^2$—; wherein each occurrence of L and W can be the same or different; R$^2$ is H or a C$_1$-C$_4$ alkyl; n is an integer selected from the group consisting of 1, 2, and 3; Ch is a chelating agent that can comprise a metal or a radiometal; and pharmaceutically acceptable salts thereof.

The phrase "wherein each occurrence of L and W can be the same or different" means that when the variable "n" is 2 or 3, one "L" group can be C$_1$-C$_6$ alkylene, whereas the other "L" group or groups can be C$_3$-C$_6$ cycloalkylene or arylene, or, in other embodiments, each "L" group can be, for example, C$_1$-C$_6$ alkylene. Likewise, for example, when "n" is 2 or 3, one "W" group can be —(C=O)—NR$^2$— and the other "W" group or groups can be —(C=S)—NR$^2$—, or, in other embodiments, each "W" can be, for example, —(C=O)—NR$^2$—.

In particular embodiments of the compound of Formula (I), R$^1$ is selected from the group consisting of:

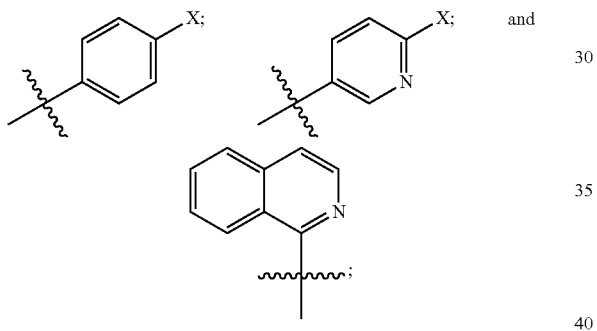

wherein X is independently Br or I.

In yet more particular embodiments of the compound of Formula (I), the chelating agent is selected from the group consisting of:

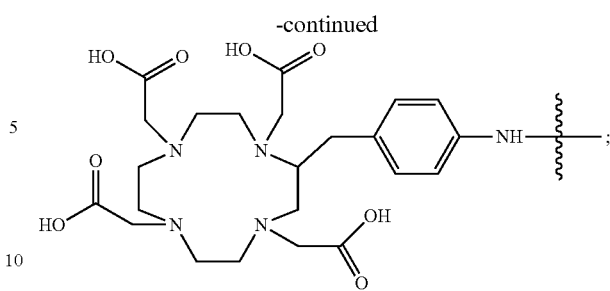

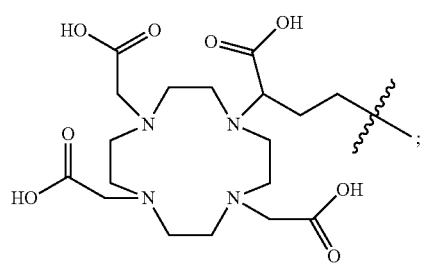

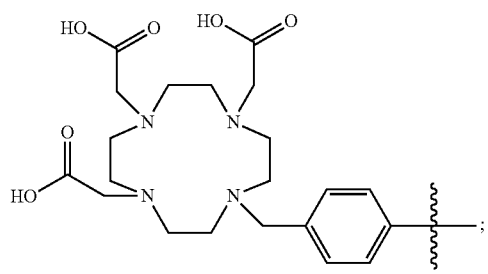

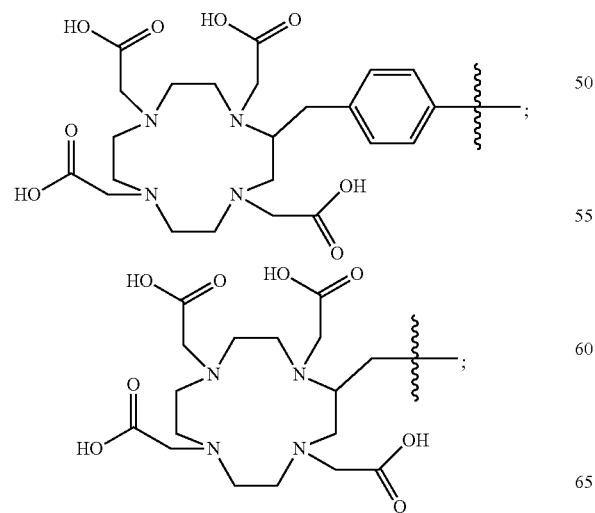

and

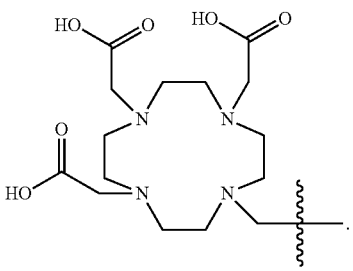

In still more particular embodiments of the compound of Formula (I), the chelating agent comprises a metal selected from the group consisting of: Y, Lu, Tc, Zr, In, Sm, Re, Cu, Pb, Ac, Bi, Al, Ga, Re, Ho and Sc. In further particular embodiments of the compound of Formula (I), the metal is a radiometal and is selected from the group consisting of: $^{68}$Ga, $^{64}$Cu, $^{86}$Y, $^{90}$Y, $^{89}$Zr, $^{111}$In, $^{99m}$Tc, $^{177}$Lu, $^{153}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

In particular embodiments, the compound of Formula (I) is selected from the group consisting of:

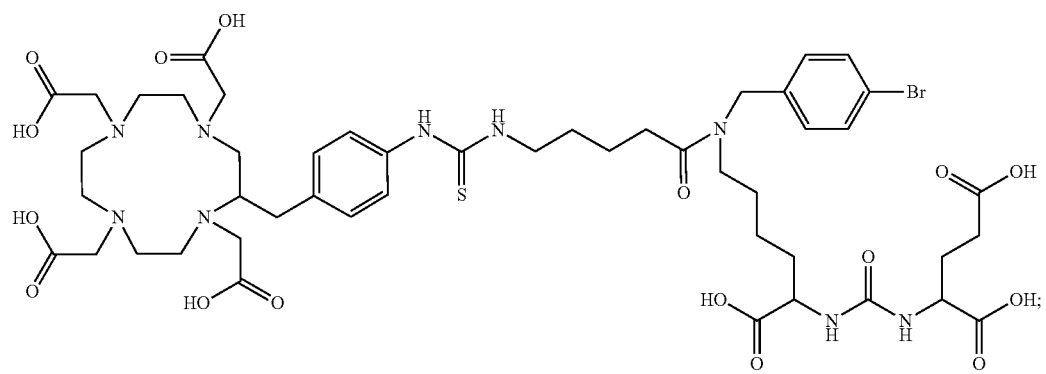
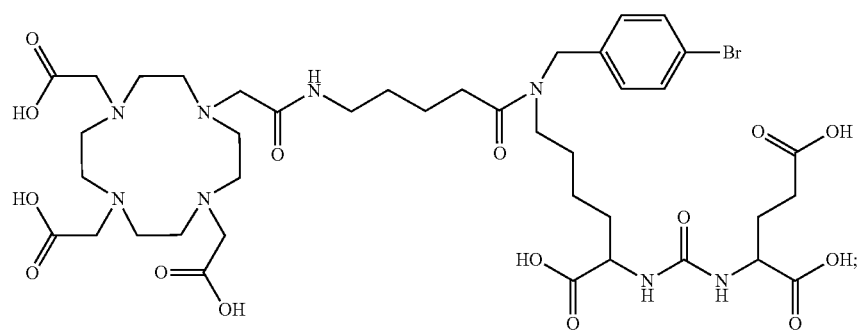
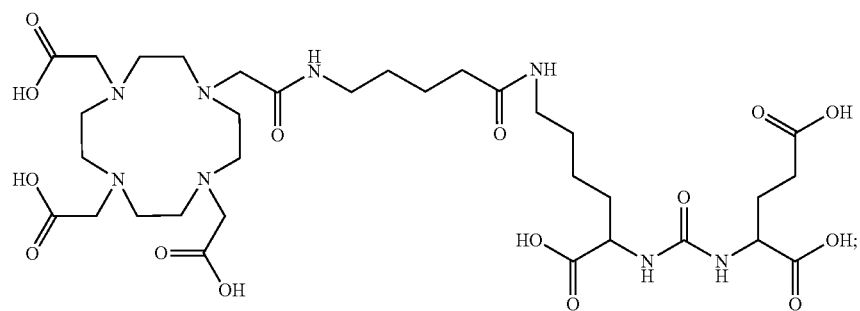
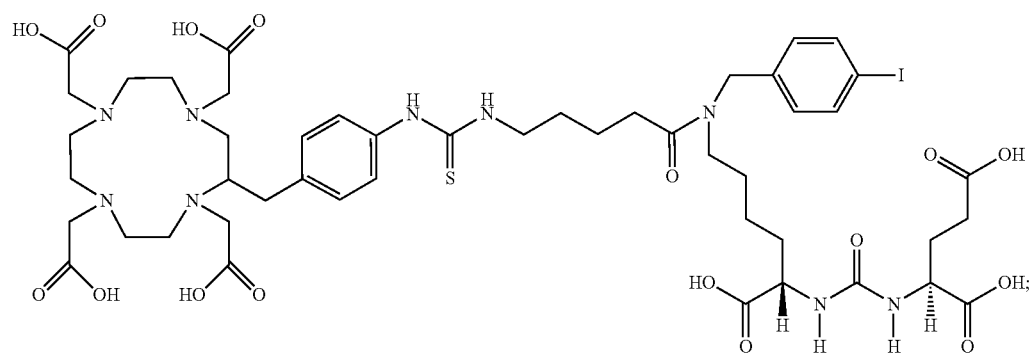

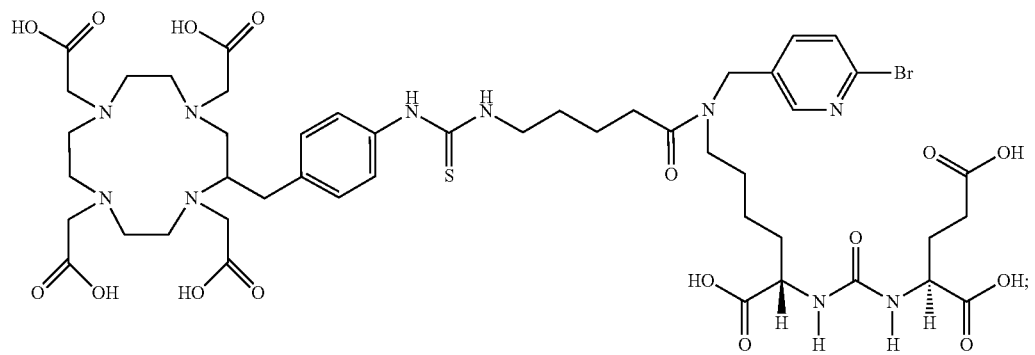
P1
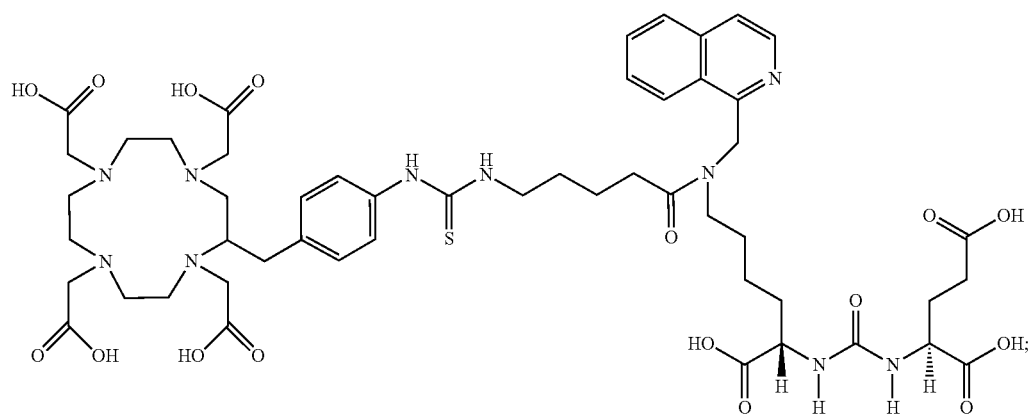
P1
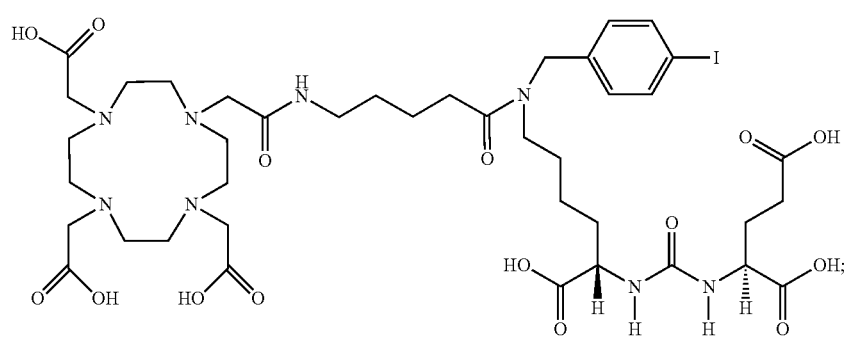
P2
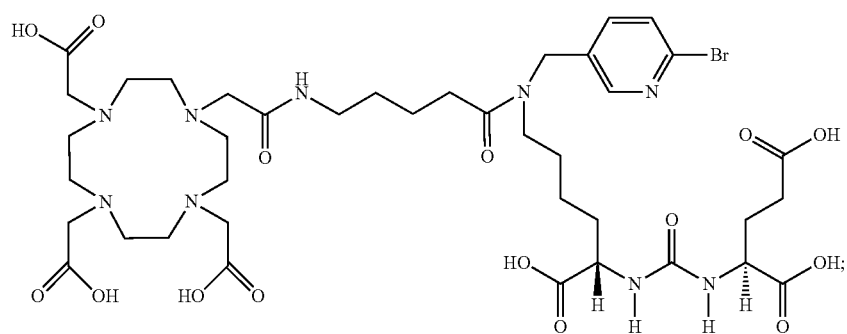
P2

-continued
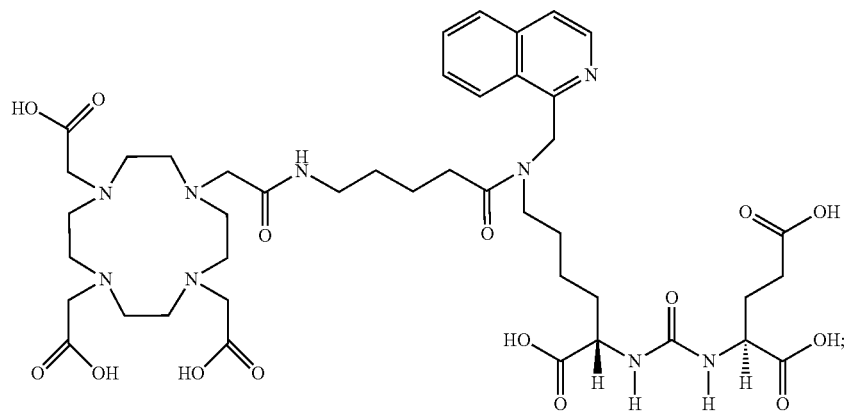
P2
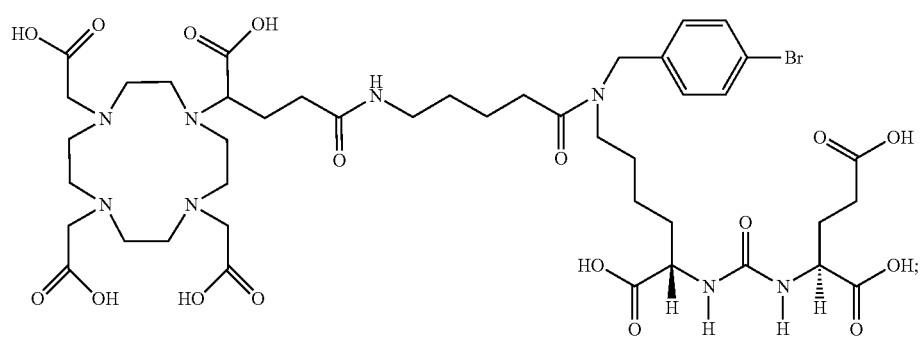
P3
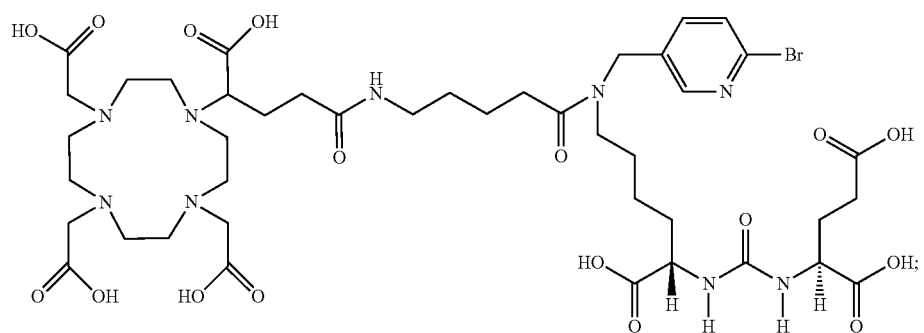
P3
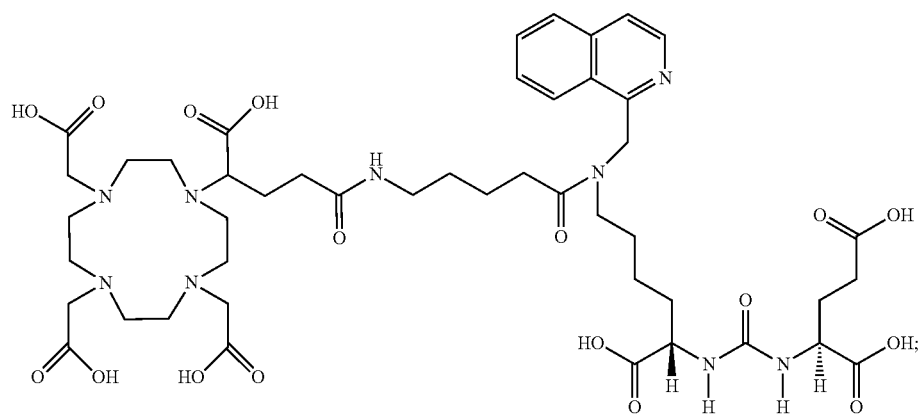
P3

P4
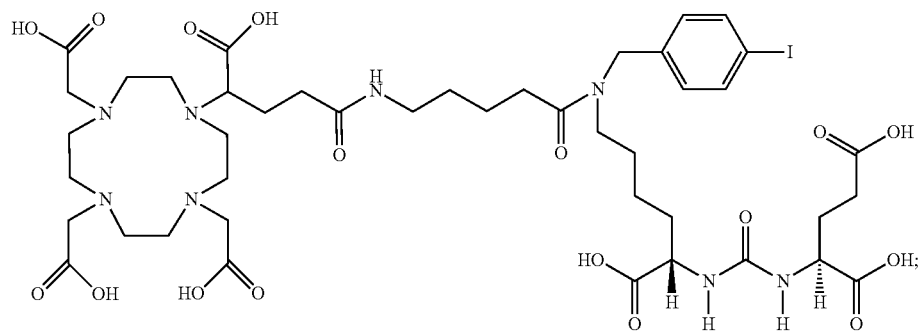
P5
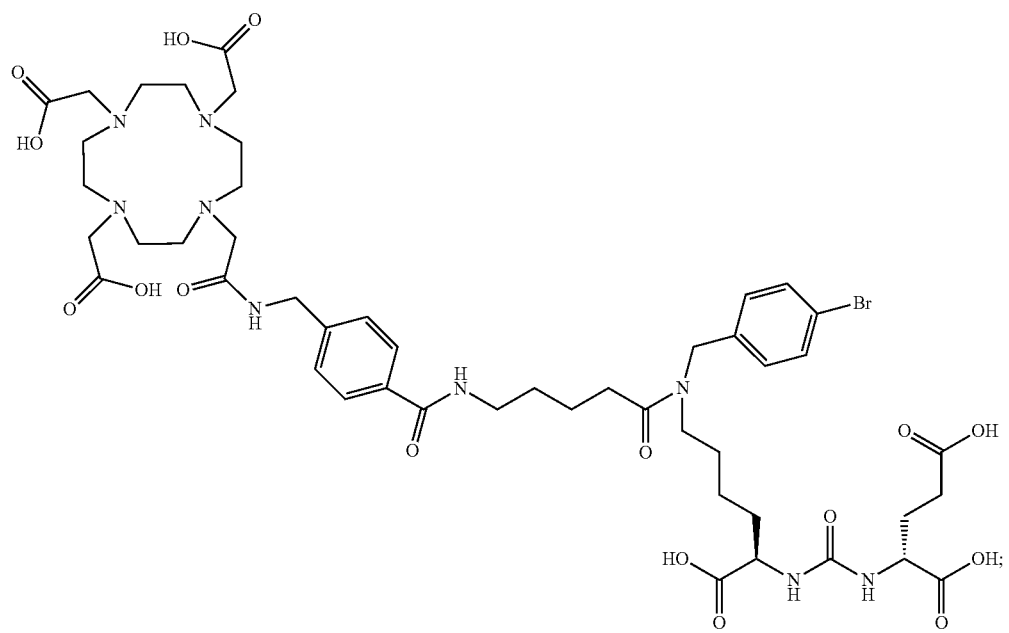
P5
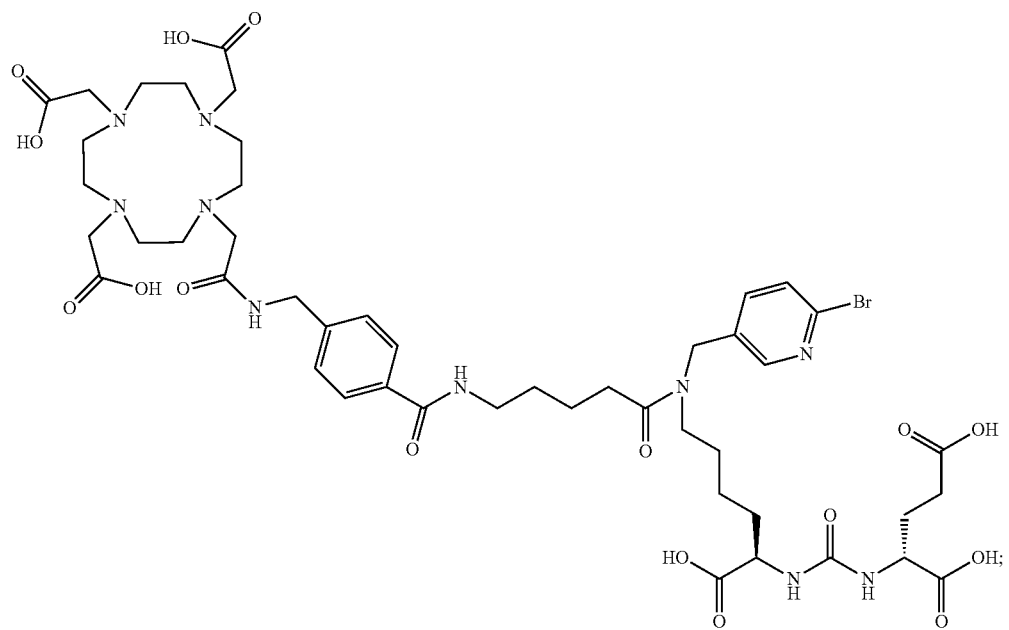

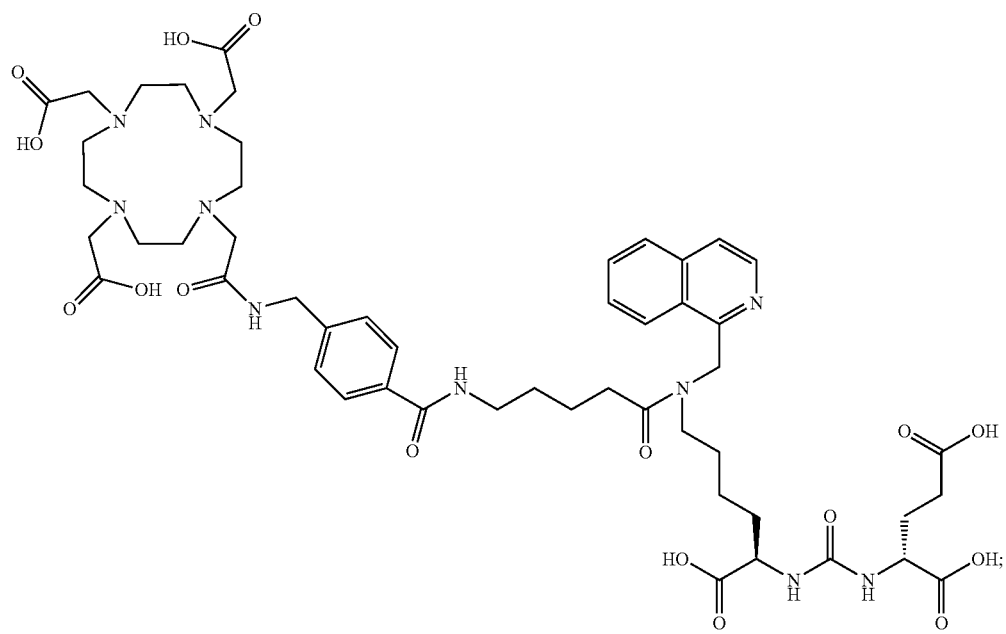
P5
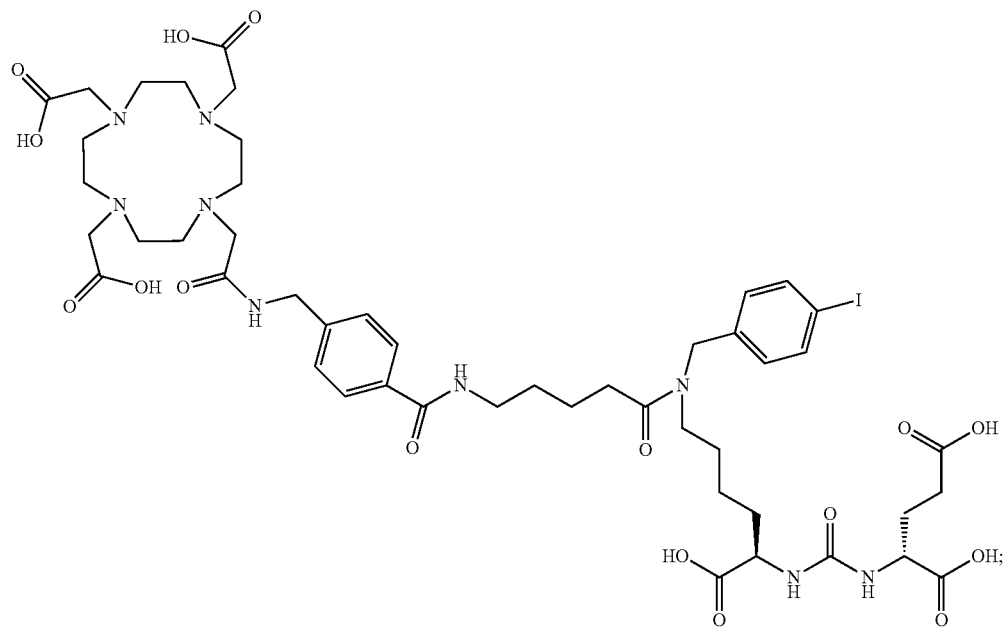
P6

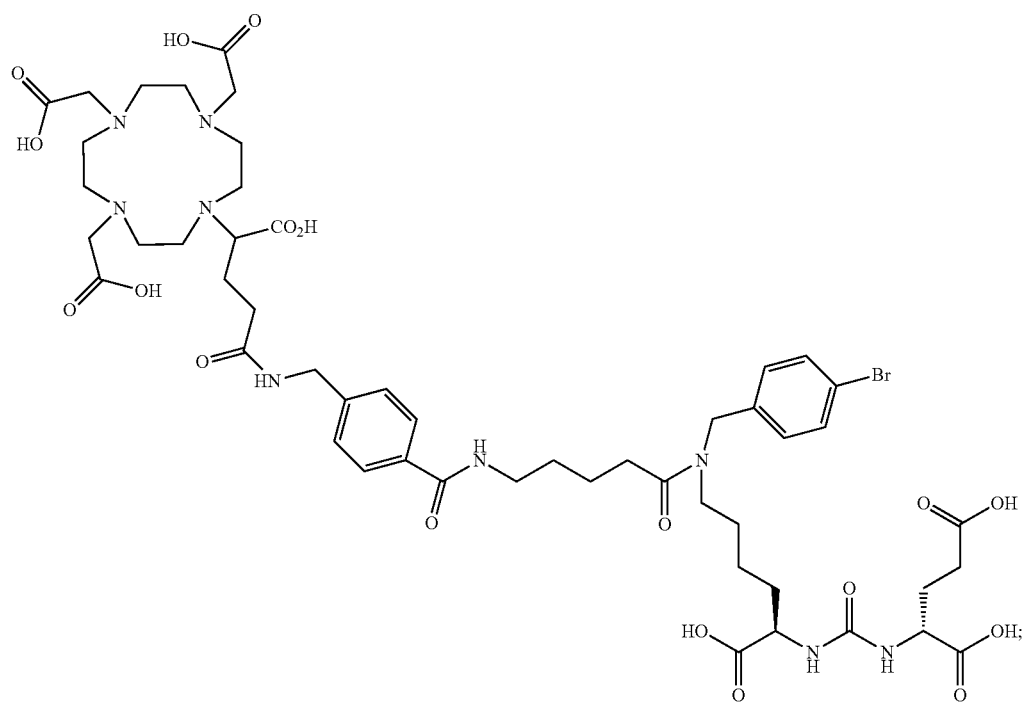
P7
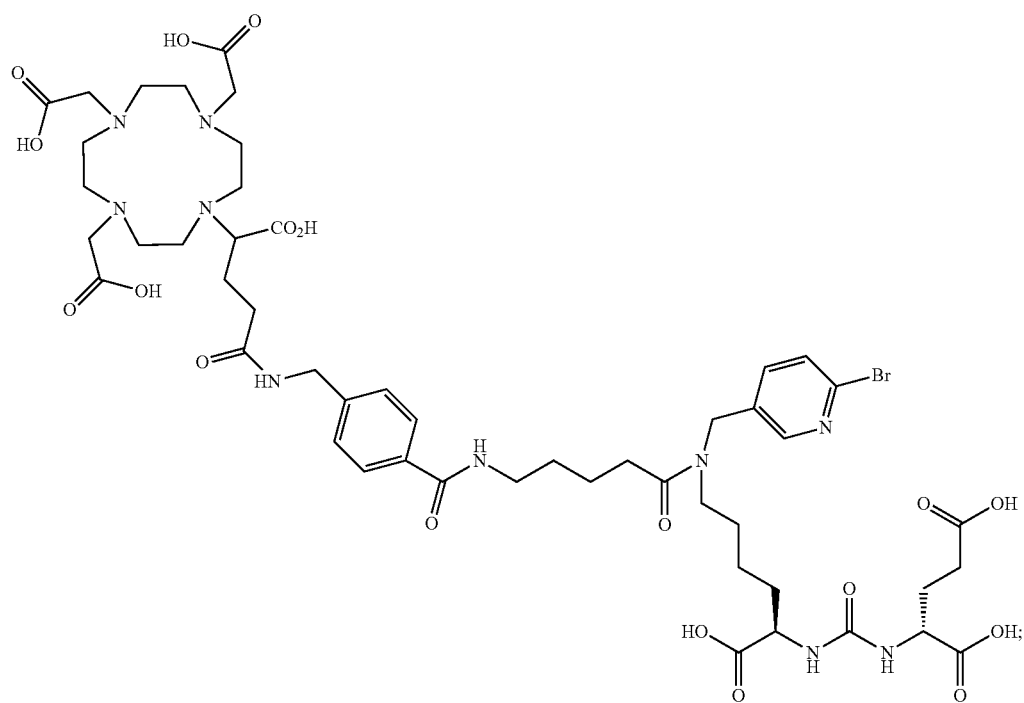
P7

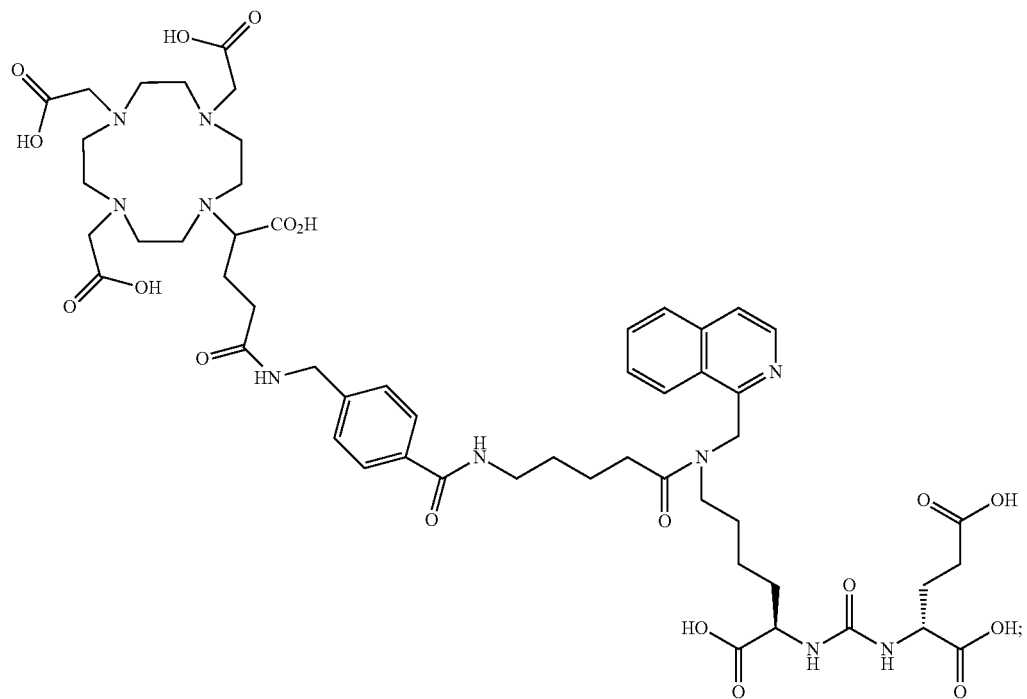
P7
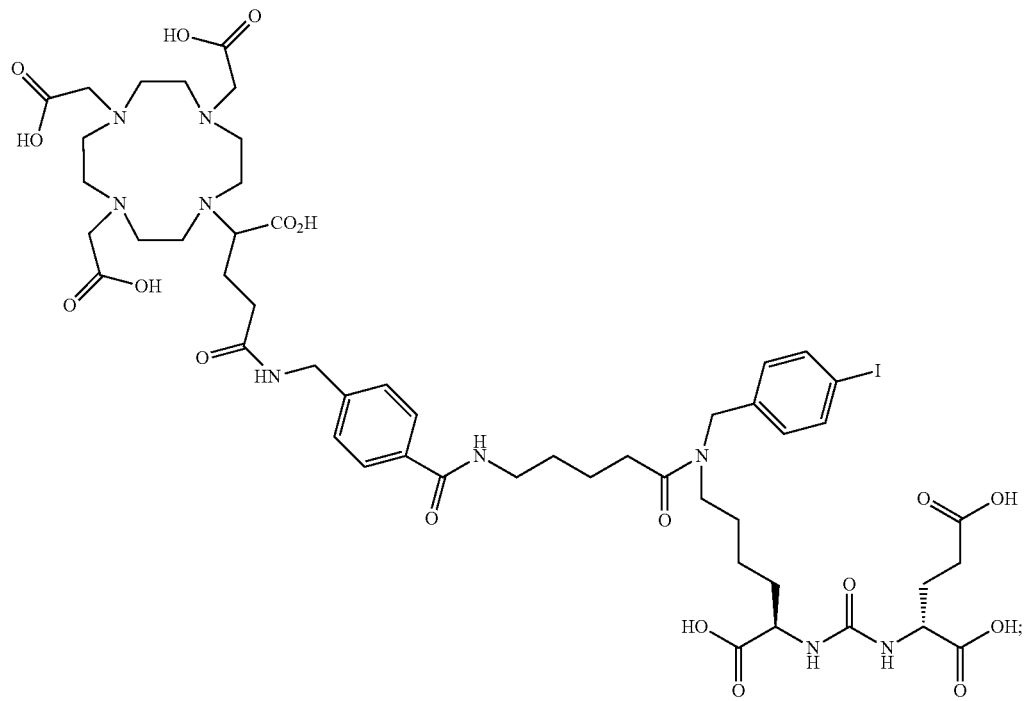
P8

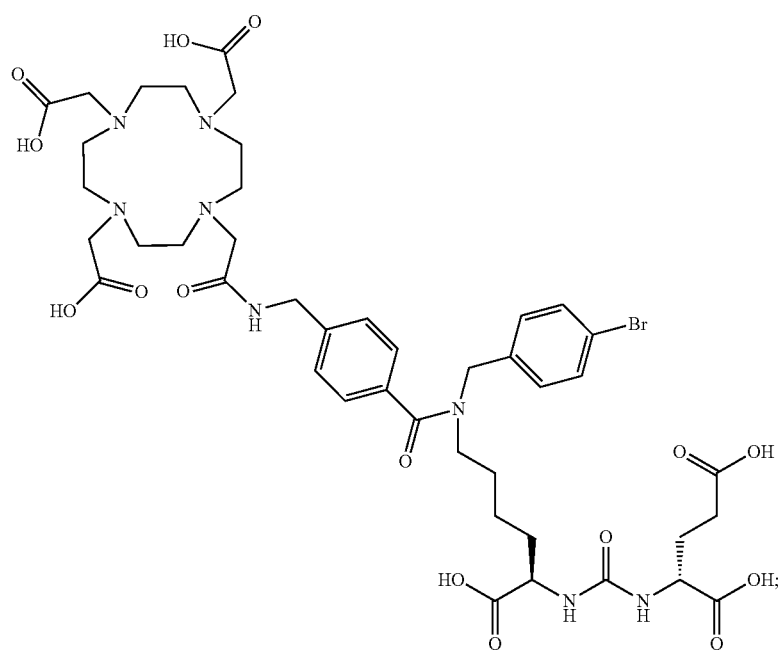
P9
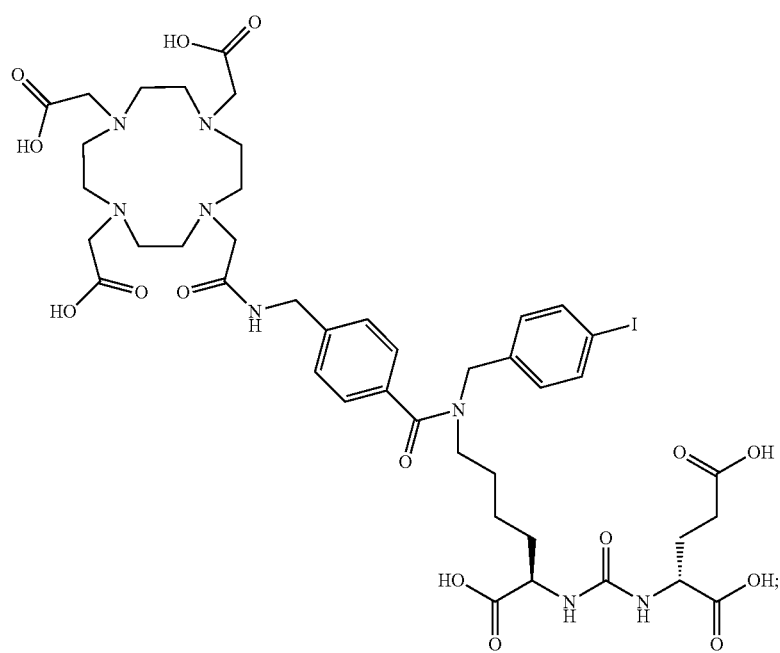
P10

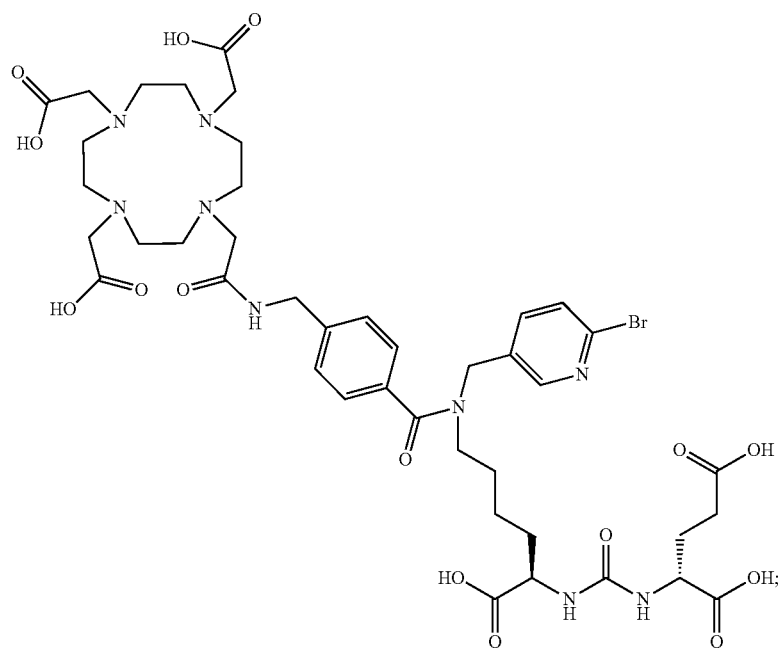
P9
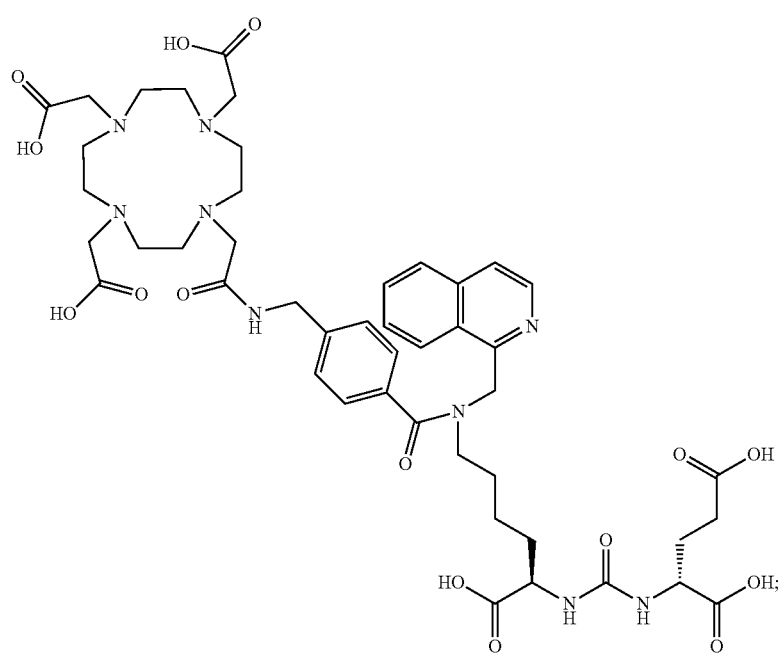
P9

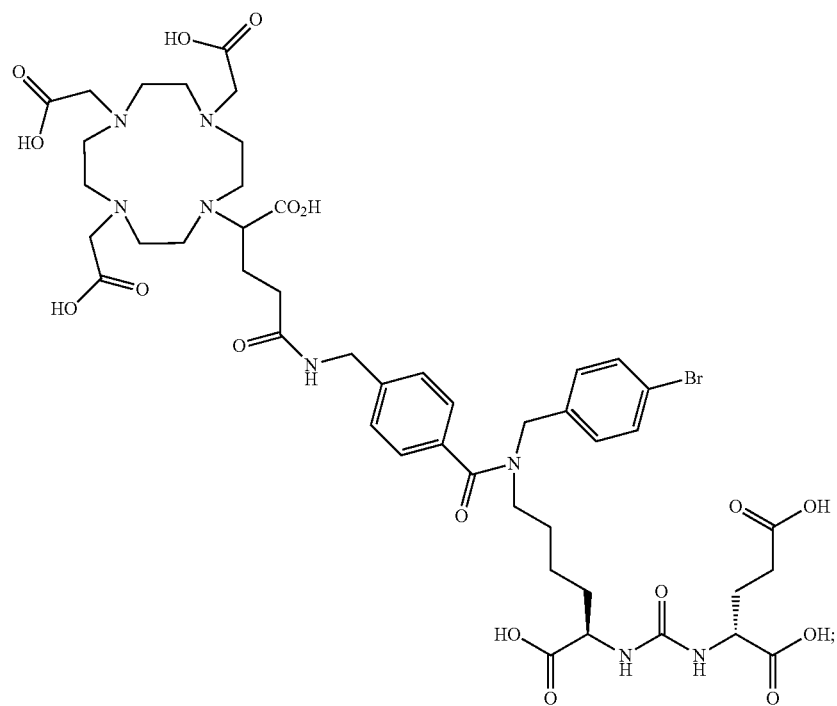
P11
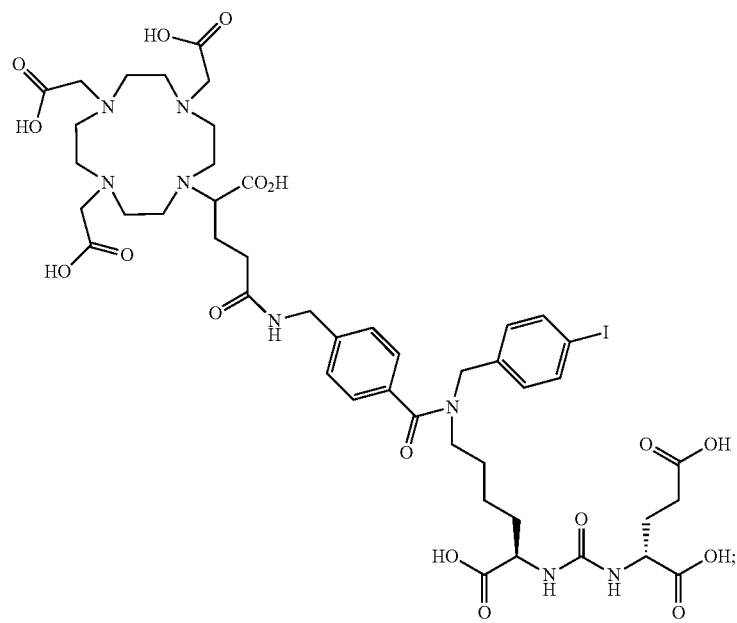
P12

P11
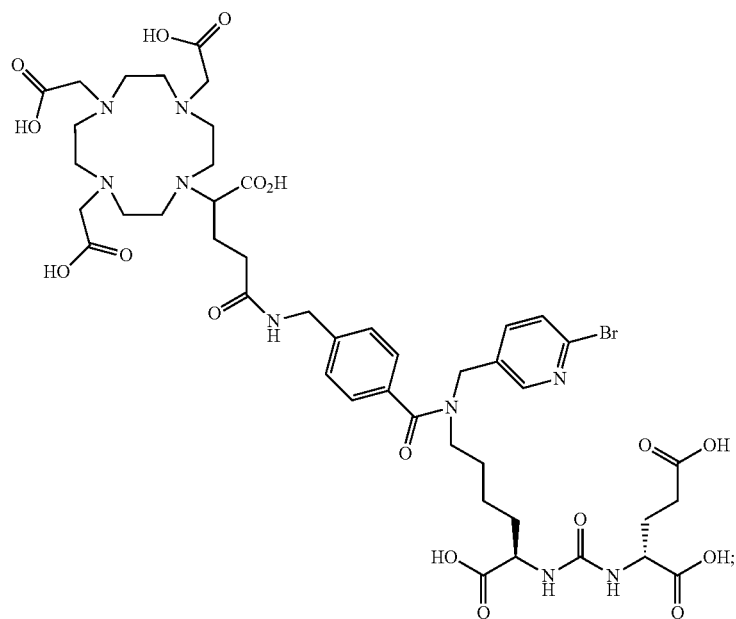
P11
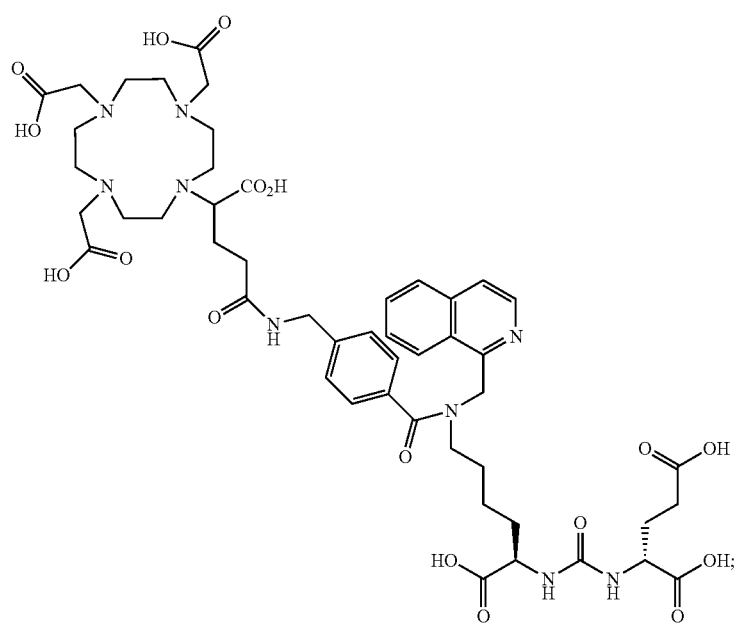

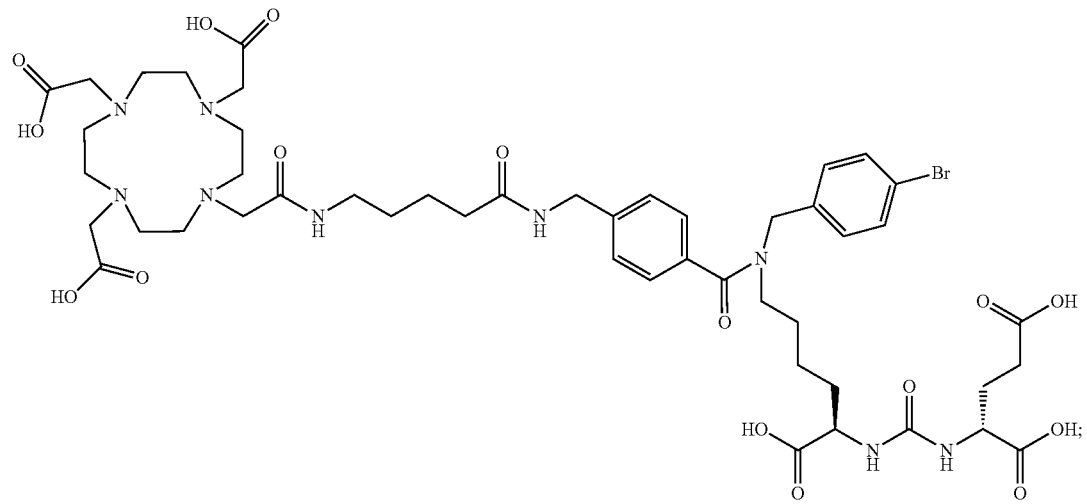
P13
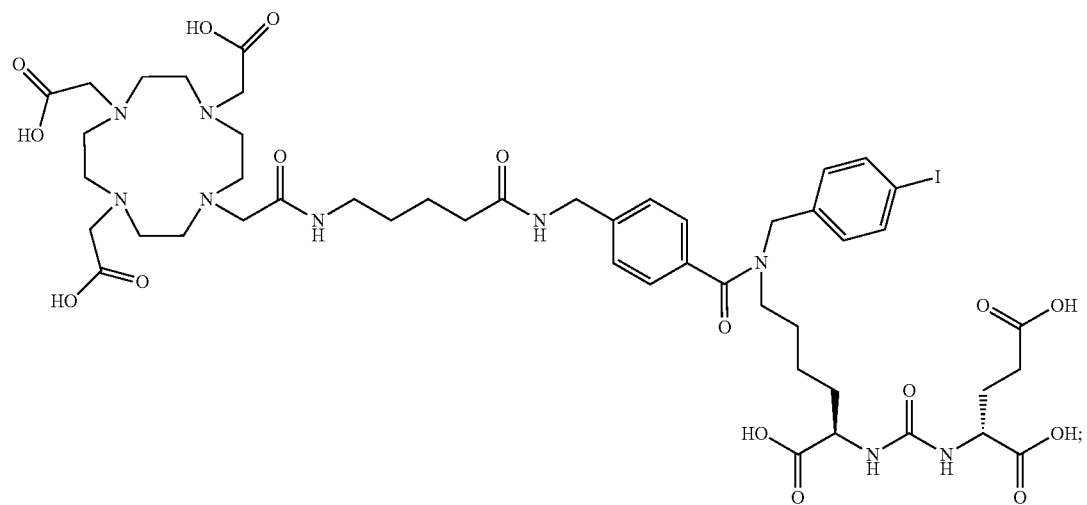
P14
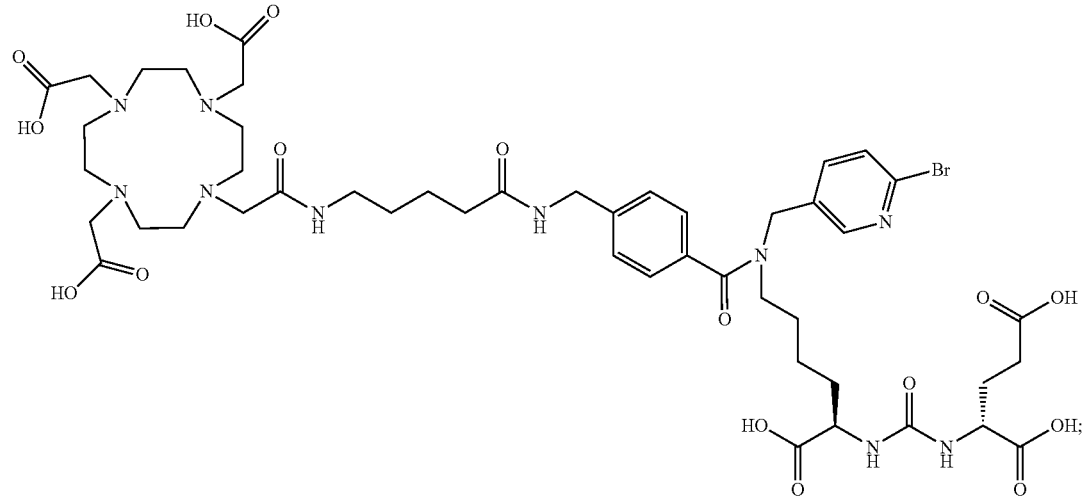
P13

-continued
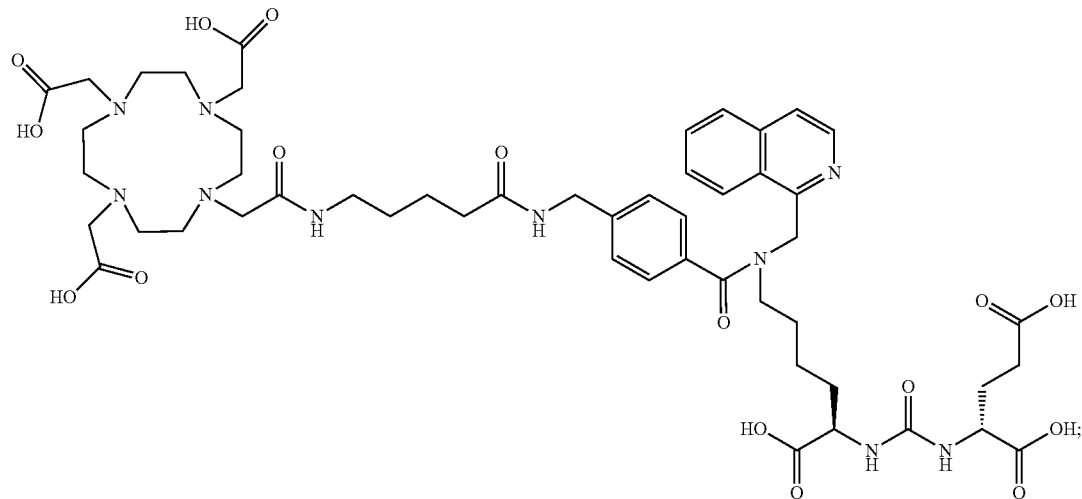
P13
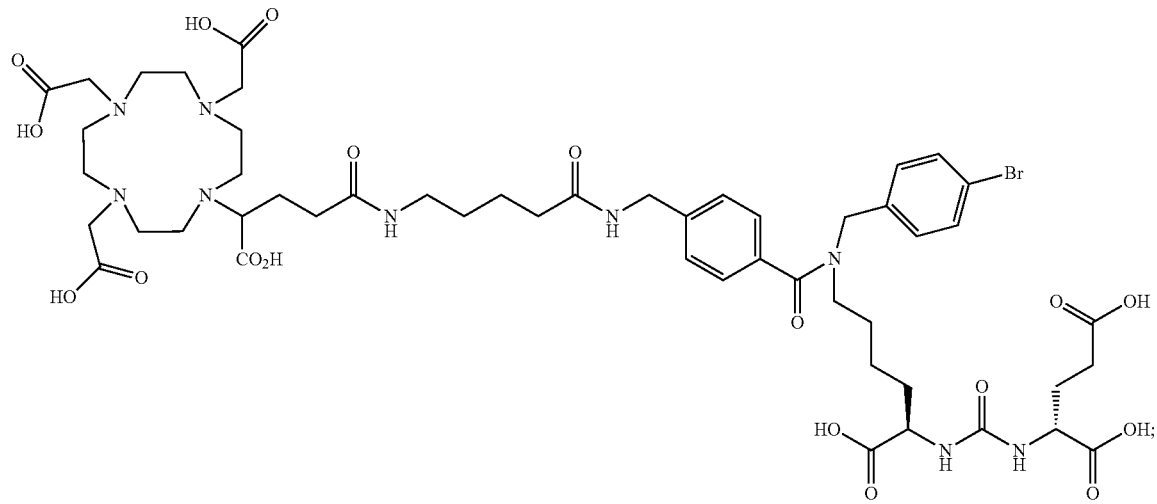
P15
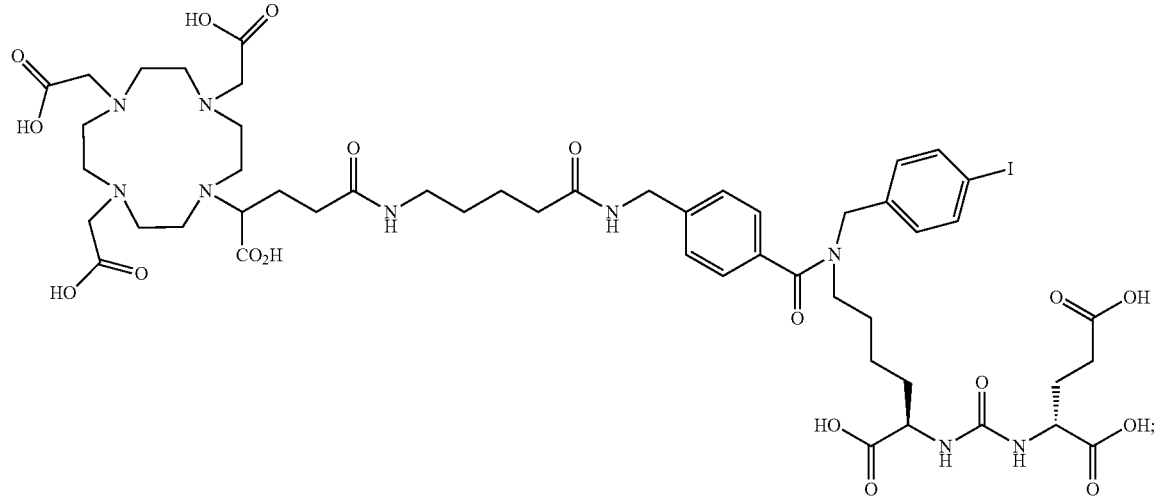
P16

-continued
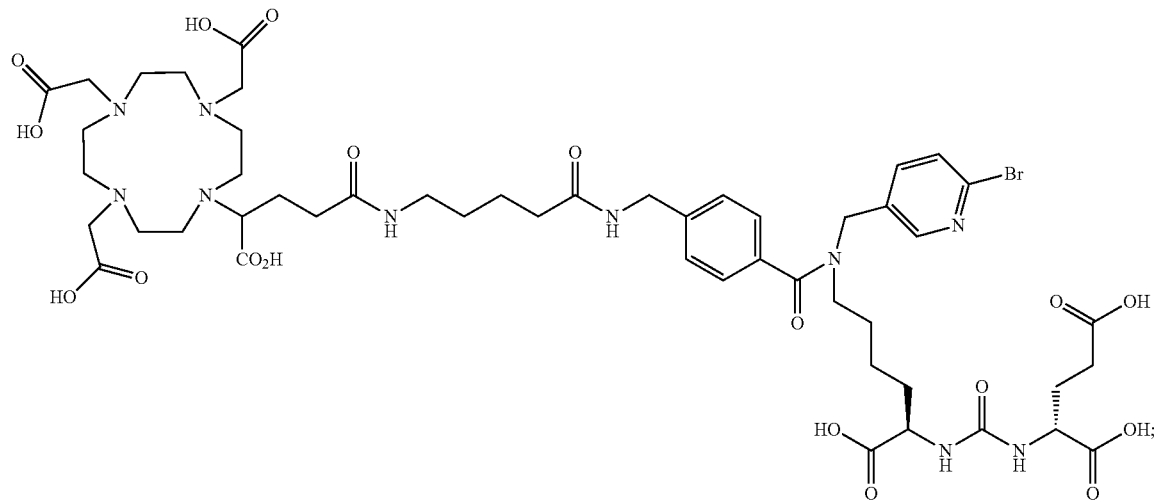
P15
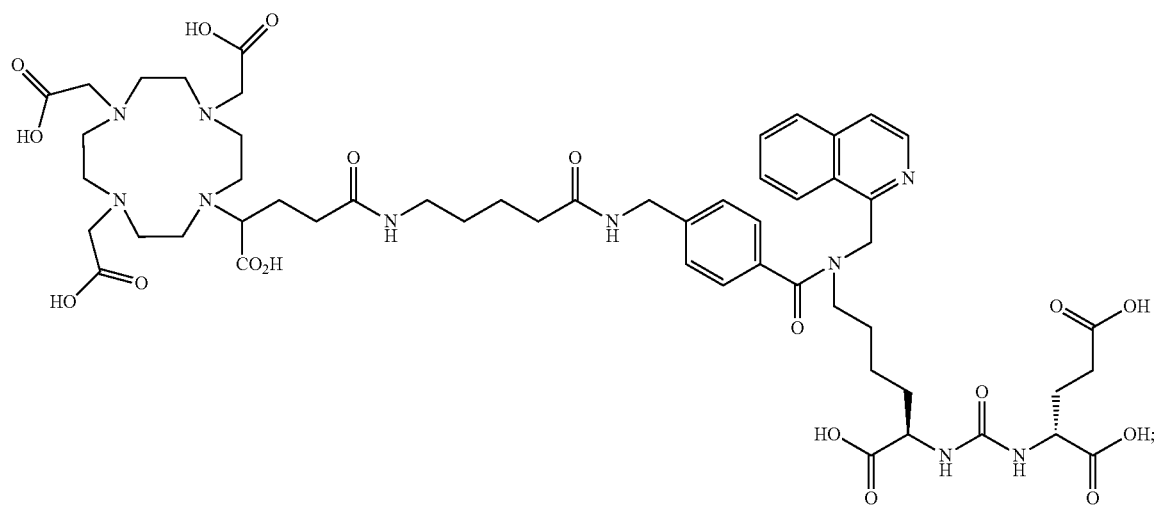
P15
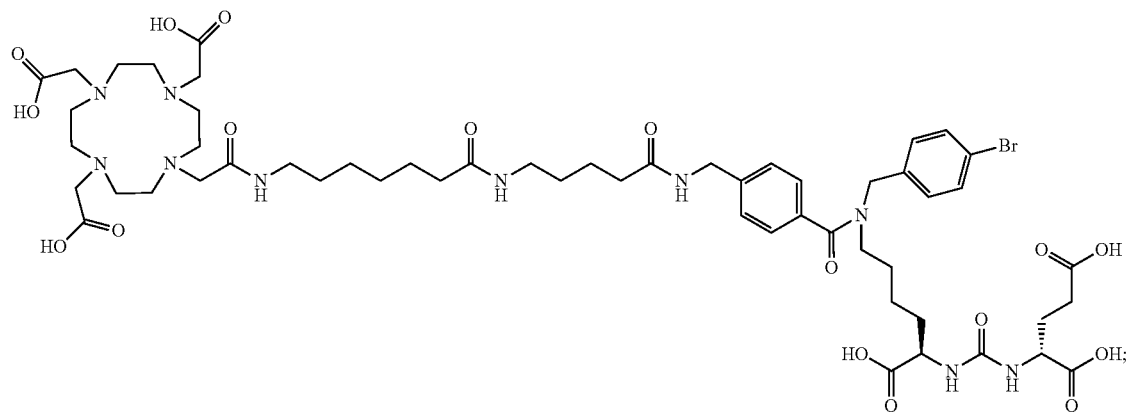
P17

-continued
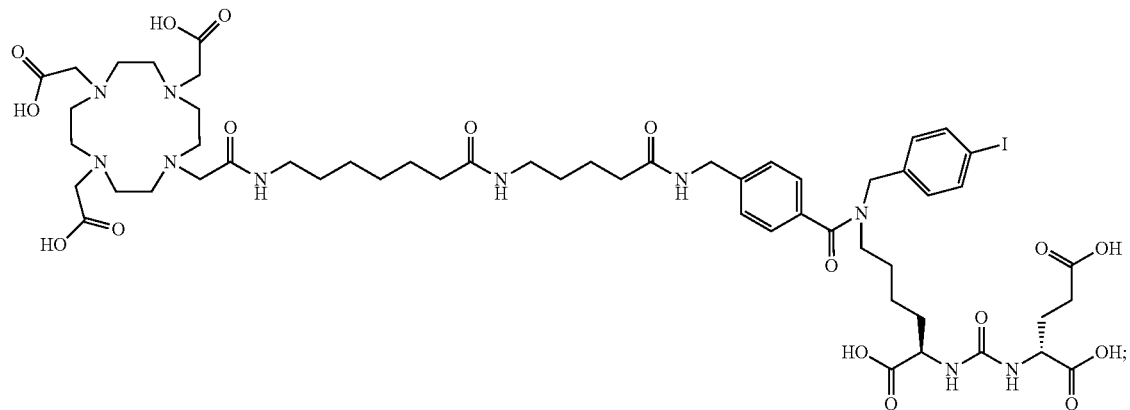
P18
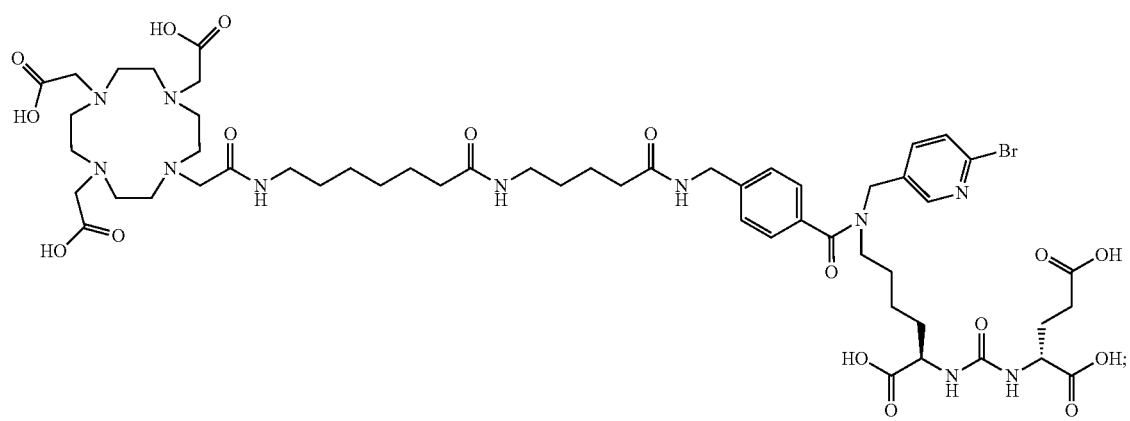
P17
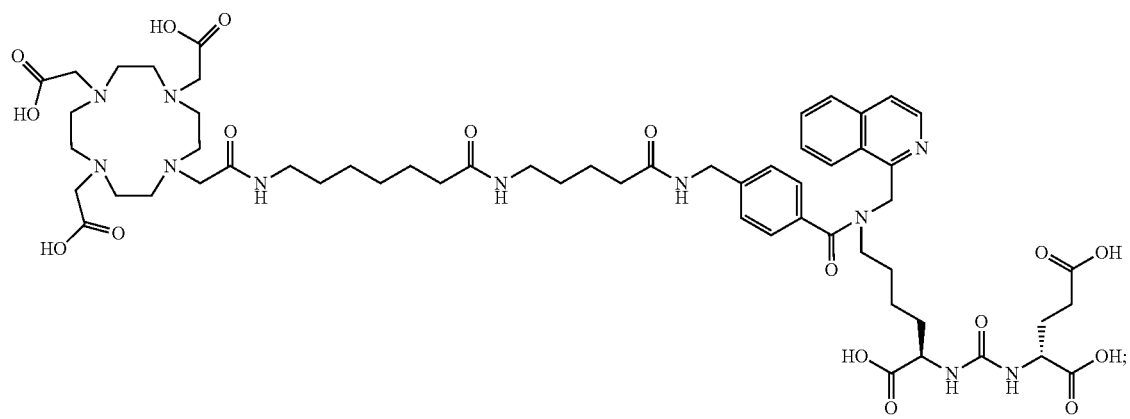
P17
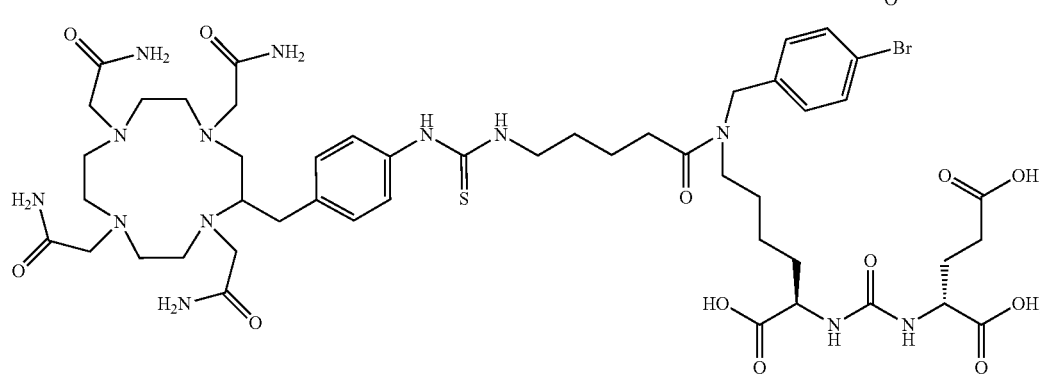

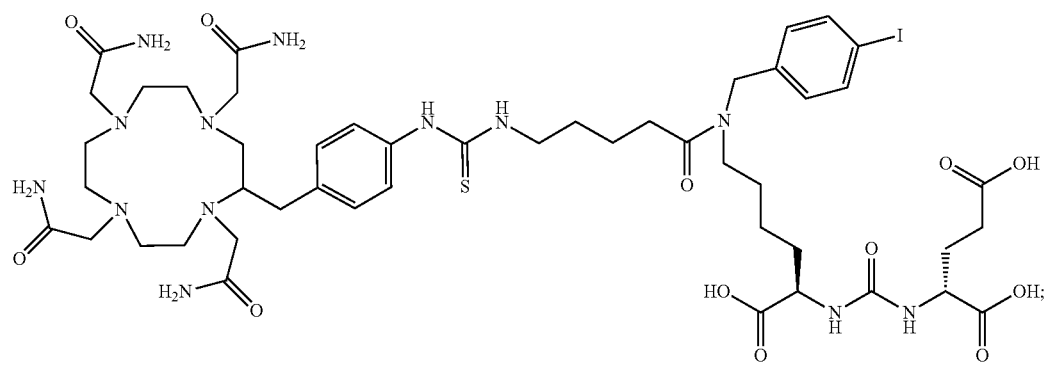
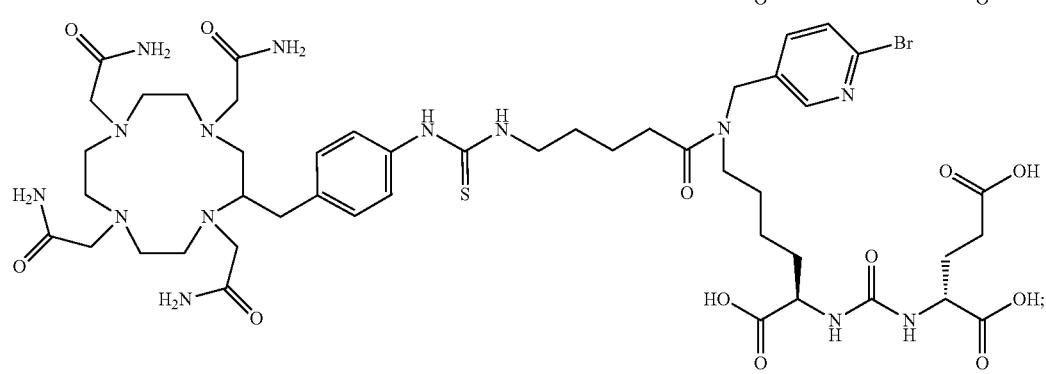
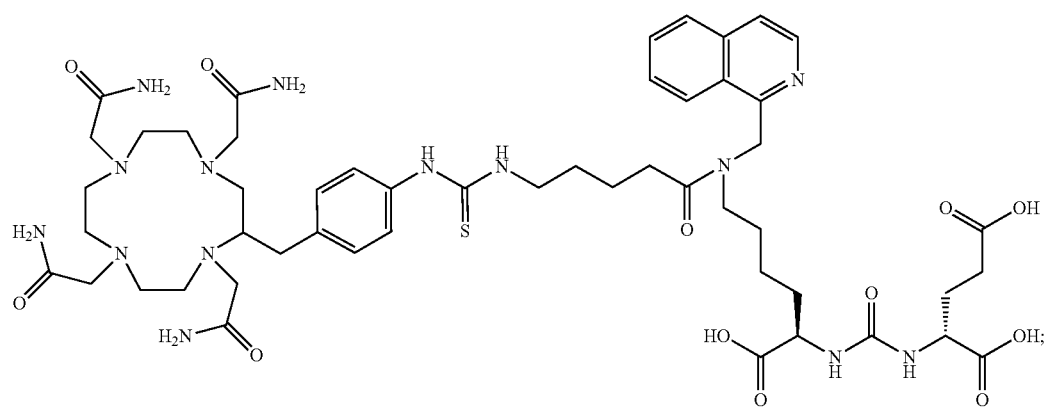
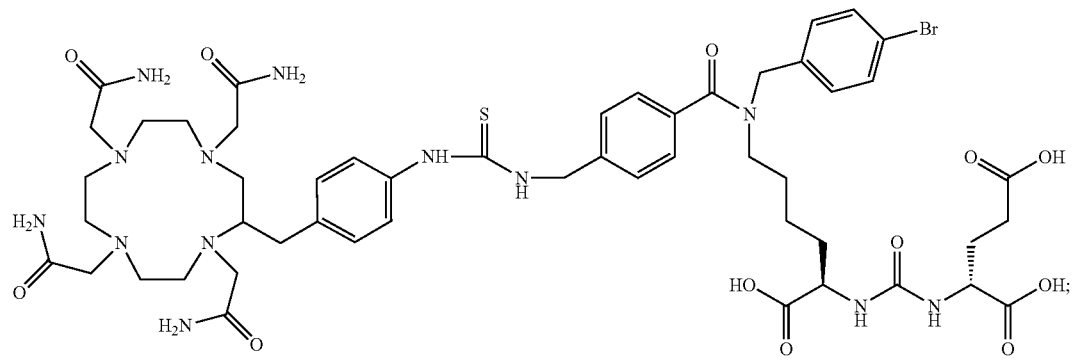

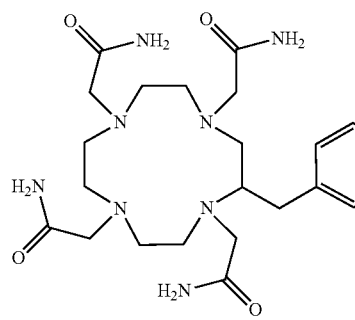 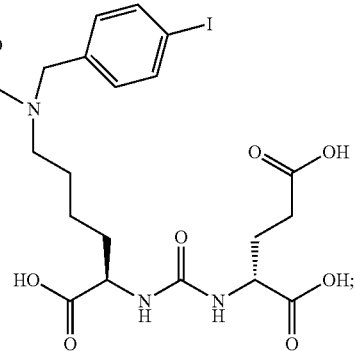
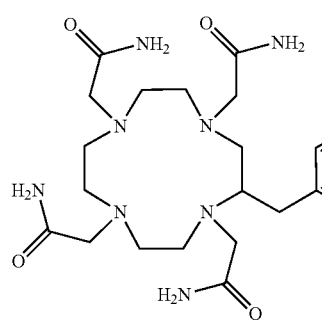 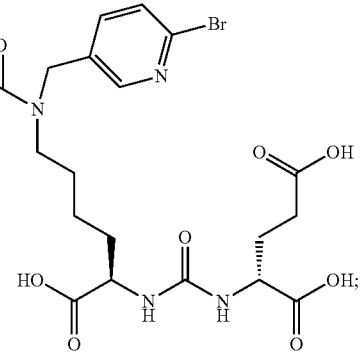
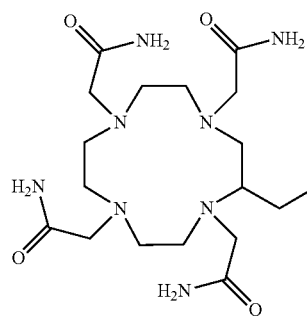 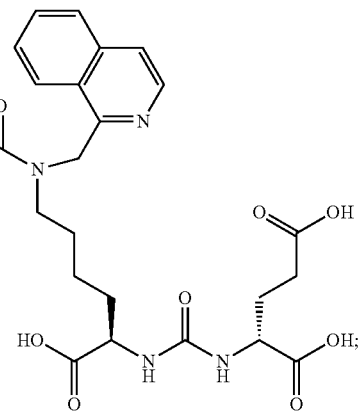
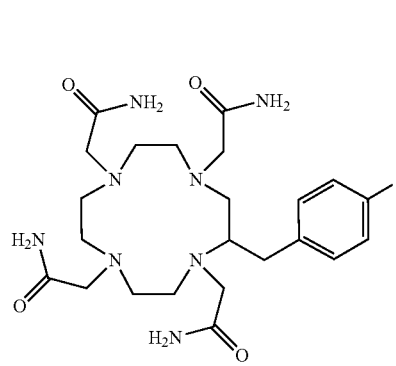 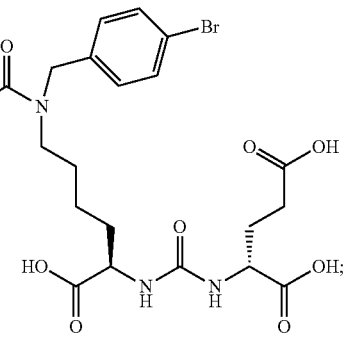

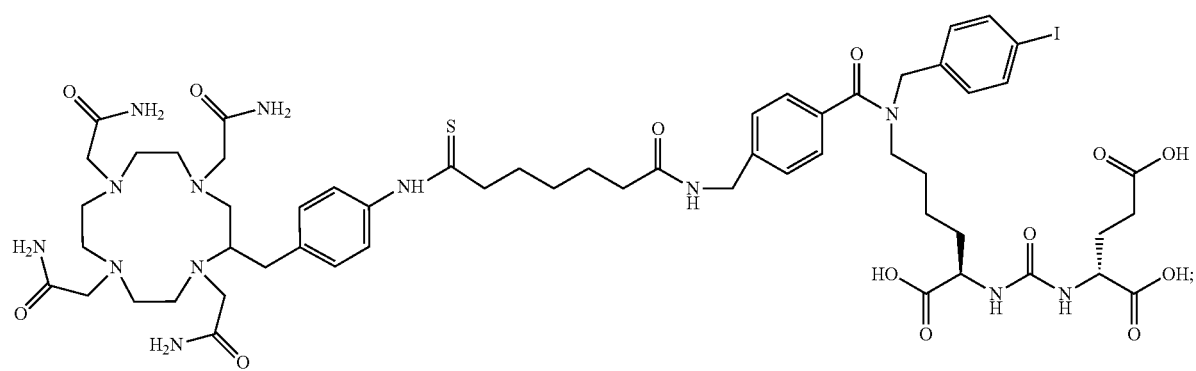
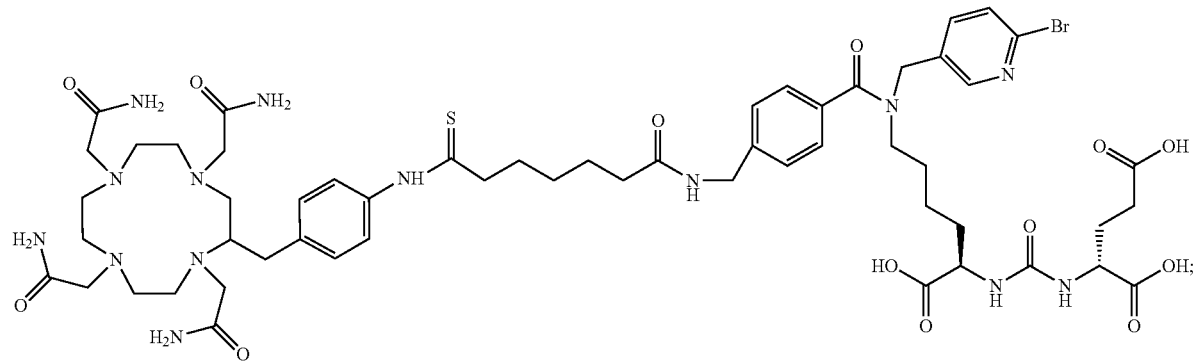
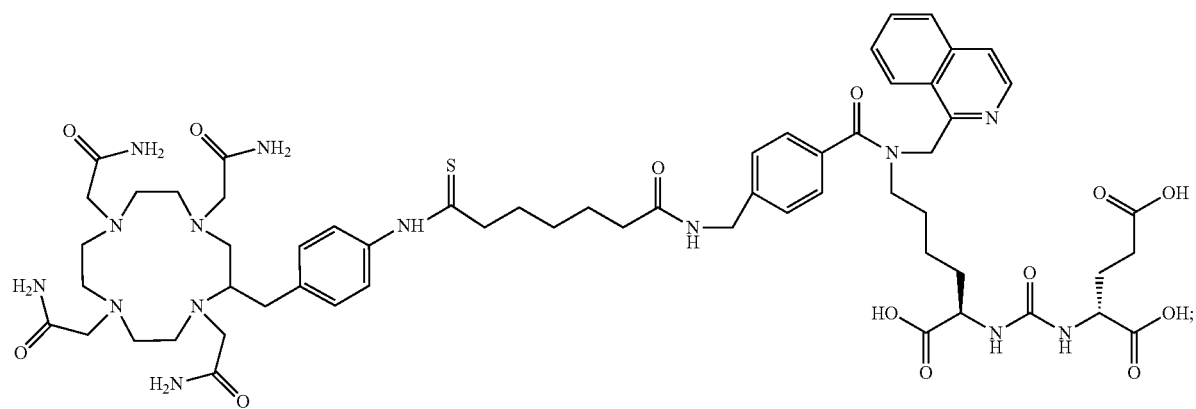
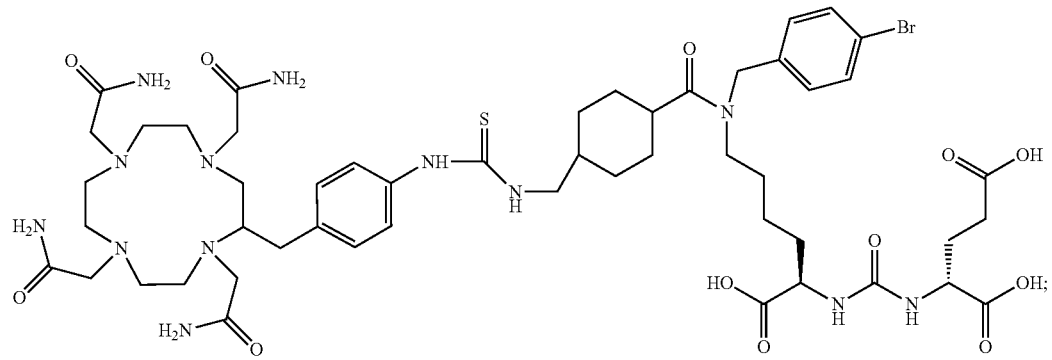

-continued

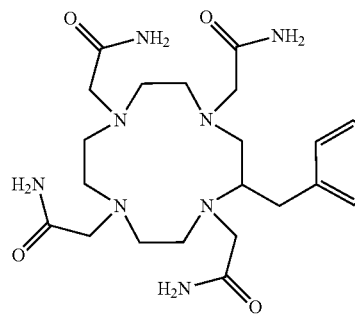
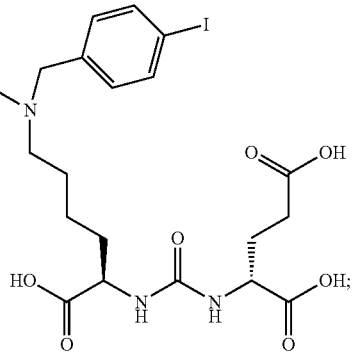

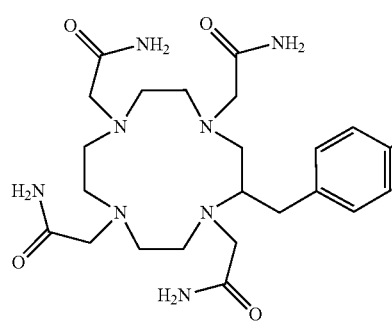
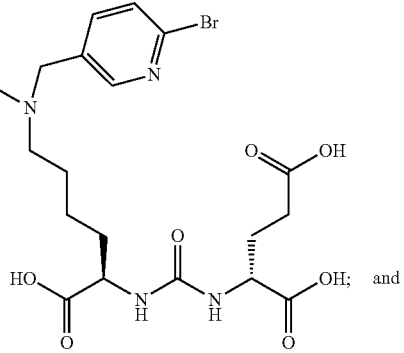

and

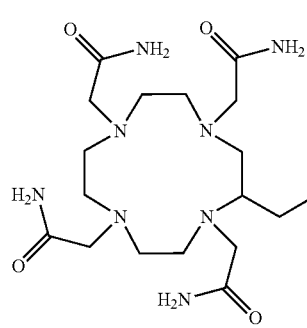
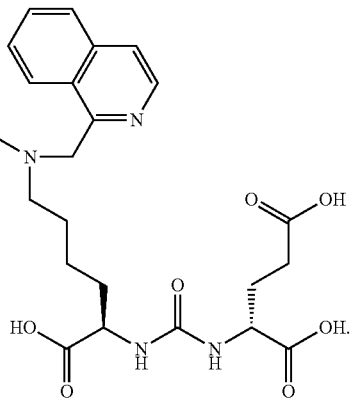

B. Methods of Using Compounds of Formula (I) for Treating One or More PSMA-Expressing Tumors or Cells In some embodiments, the presently disclosed subject matter provides a method for treating one or more PSMA expressing tumors or cells, the method comprising contacting the one or more PSMA expressing tumors or cells with an effective amount of a compound of formula (I), the compound of formula (I) comprising:

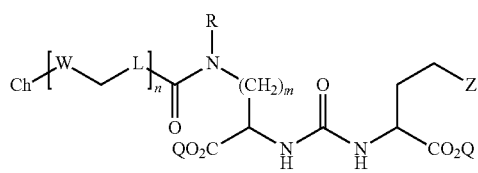

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ is selected from the group consisting of substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1, 2, and 3; Ch is a chelating agent that comprises a radiometal suitable for radiotherapy; and pharmaceutically acceptable salts thereof.

"Contacting" means any action which results in at least one compound comprising the therapeutic agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of Formula (I) and at least one other active agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

In particular embodiments, R$^1$ is selected from the group consisting of:

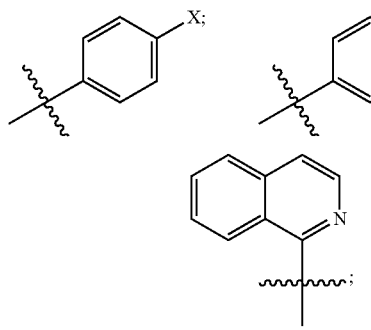

wherein X is independently Br or I.

In more particular embodiments, the chelating agent is selected from the group consisting of:

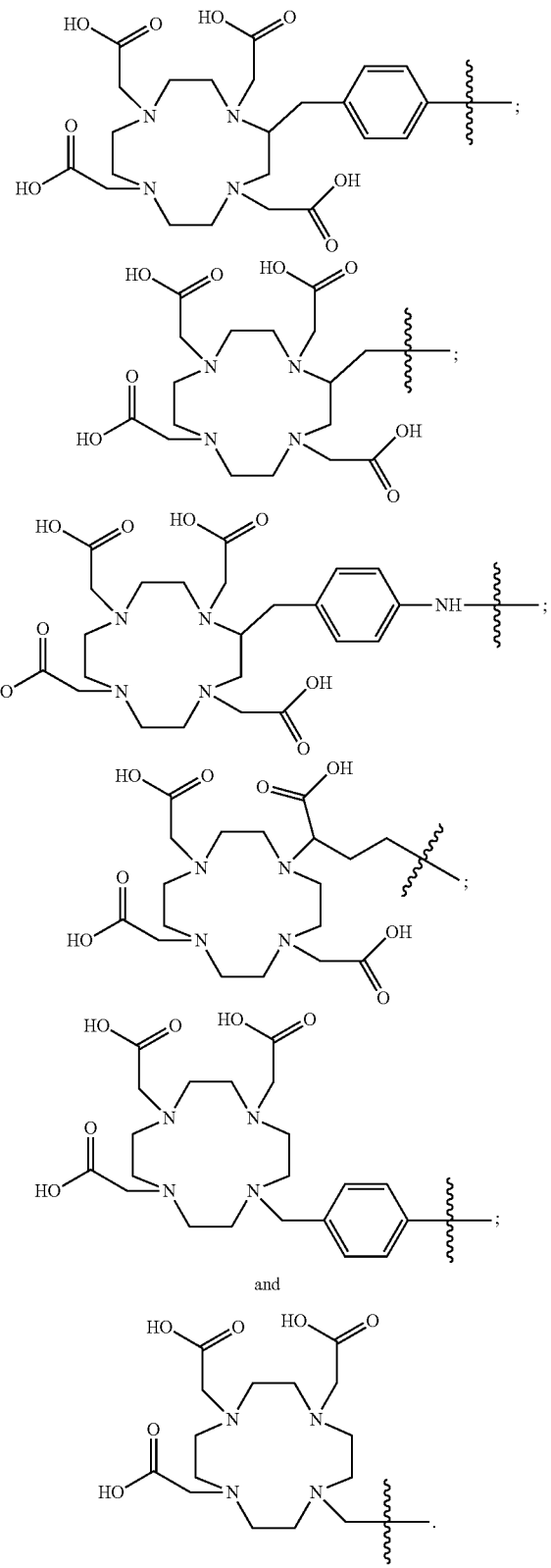

In yet more particular embodiments, the radiometal suitable for radiotherapy is selected from the group consisting of: $^{90}$Y, $^{177}$Lu, $^{211}$At, $^{111}$In, $^{153}$Sm, $^{186}$Re, $^{188}$Re, $^{67}$Cu, $^{212}$Pb, $^{225}$Ac, $^{213}$Bi, $^{212}$Bi, $^{212}$Pb, and $^{67}$Ga.

In still more particular embodiments, the compound of formula (I) is selected from the group consisting of:
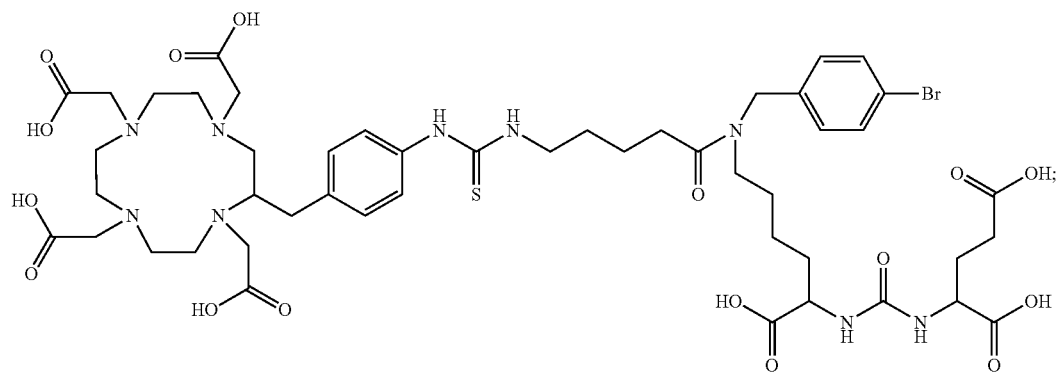
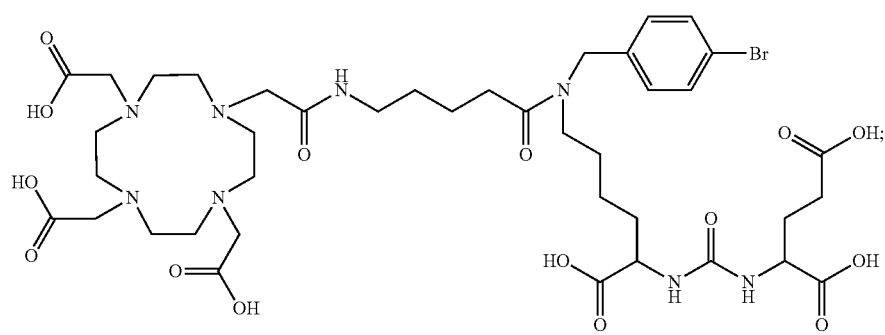
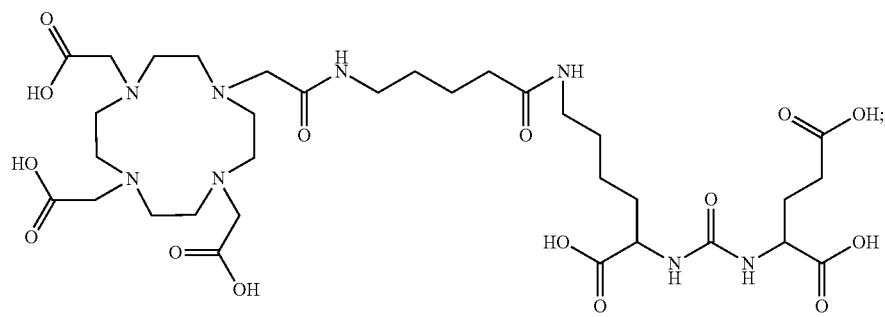
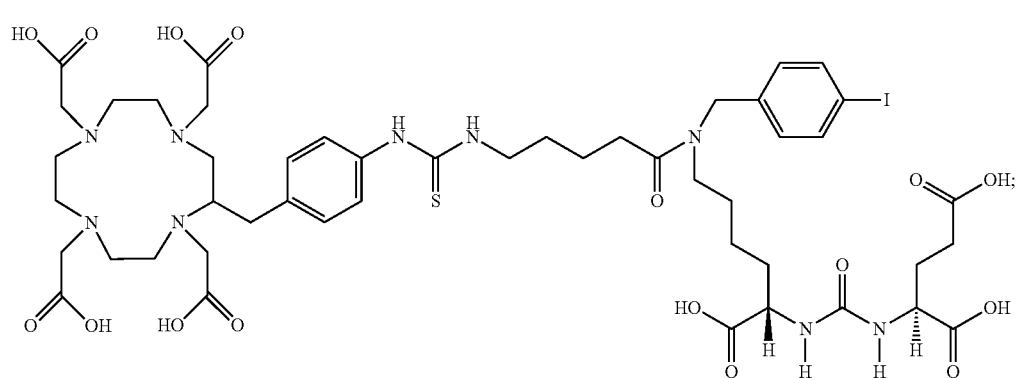
P1

-continued
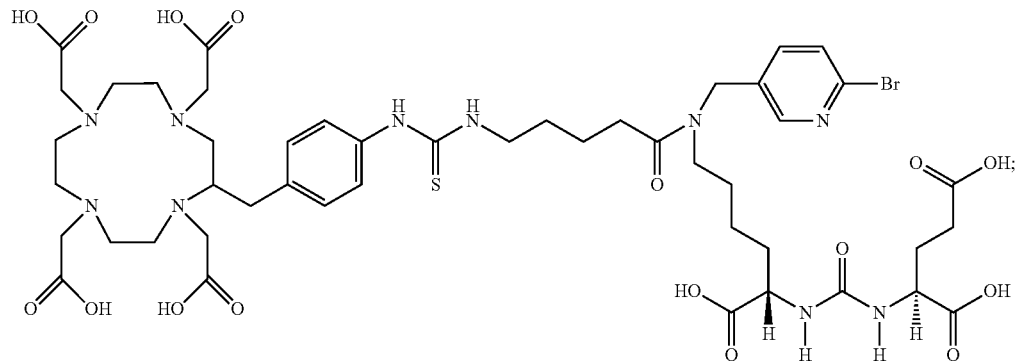
P1
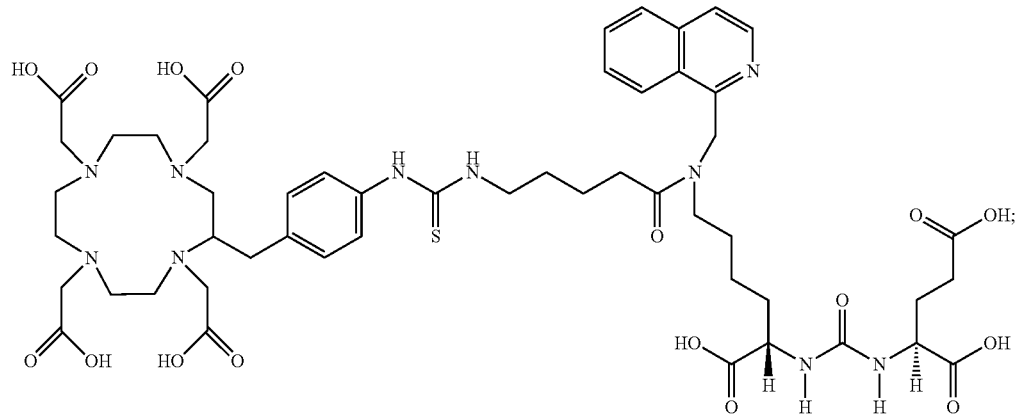
P1
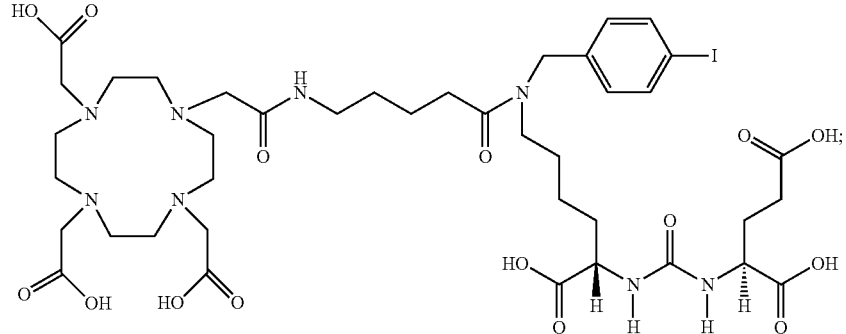
P2
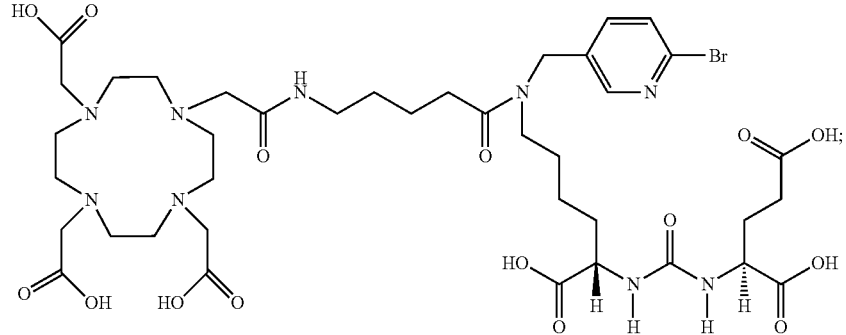
P2

-continued
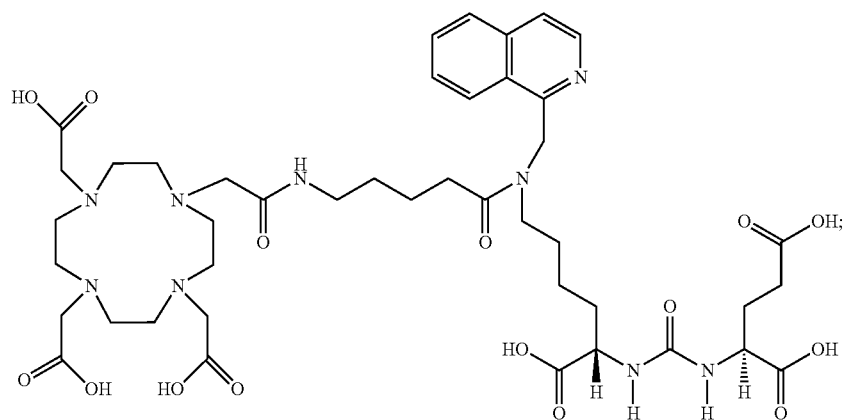
P2
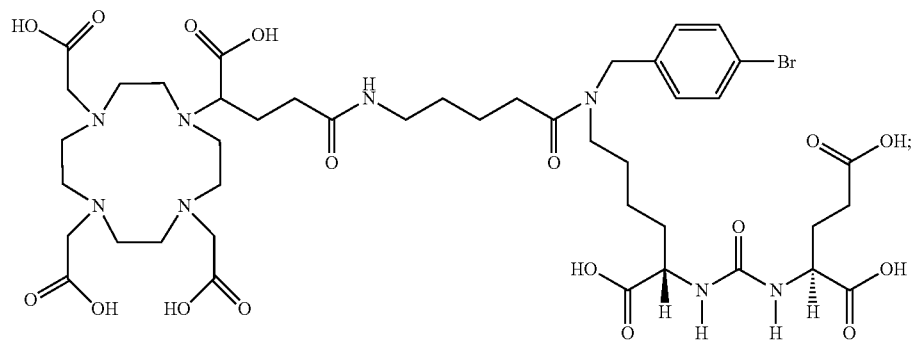
P3
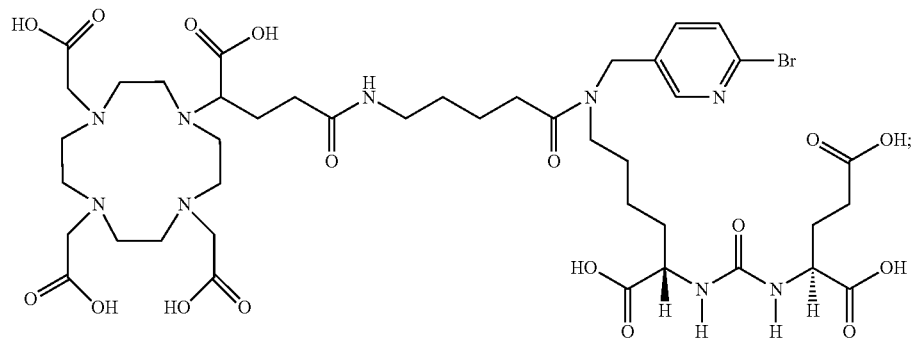
P3
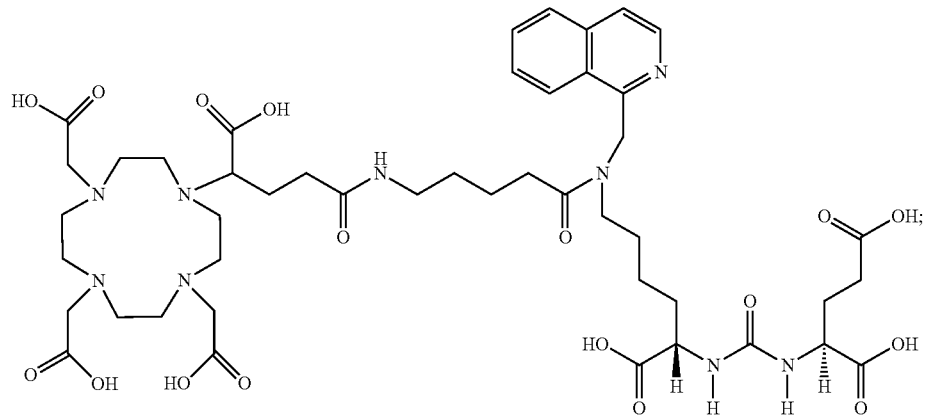
P3

-continued
P4
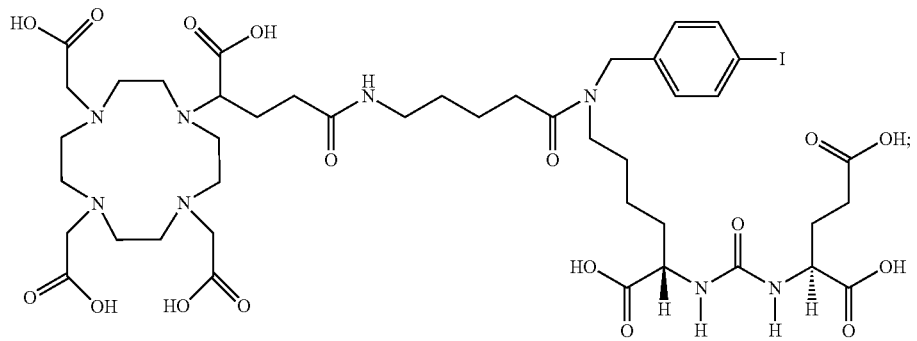
P5
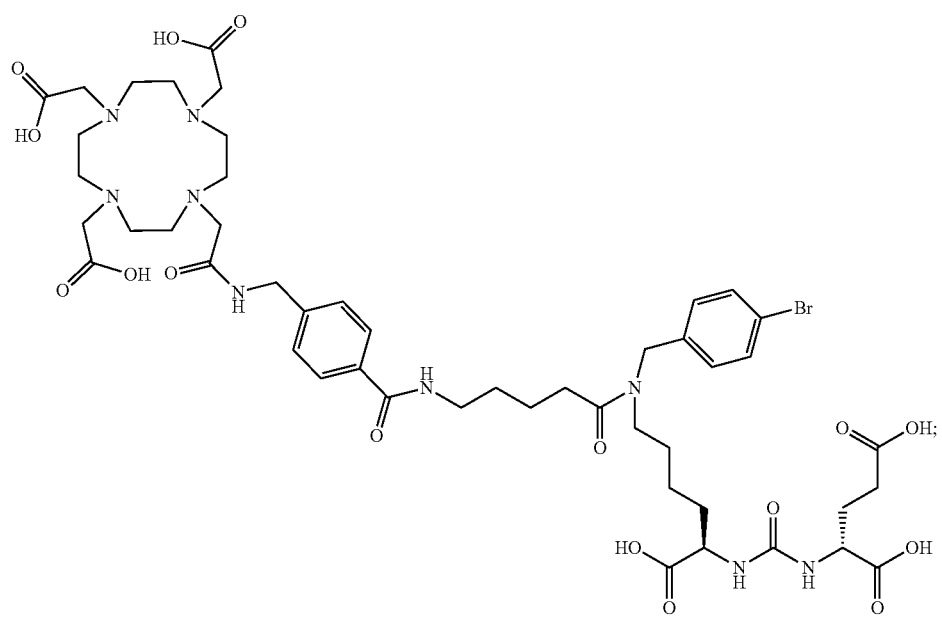
P5
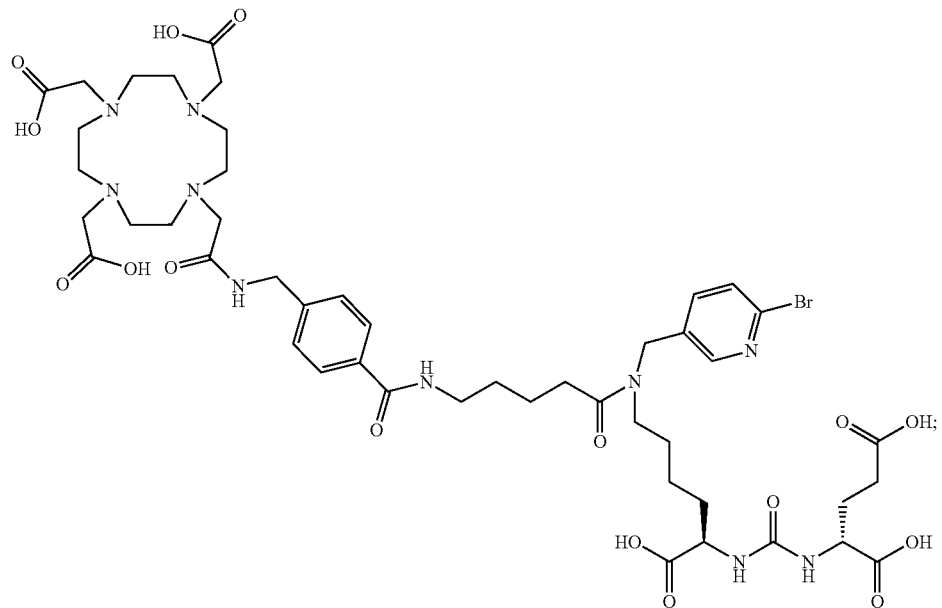

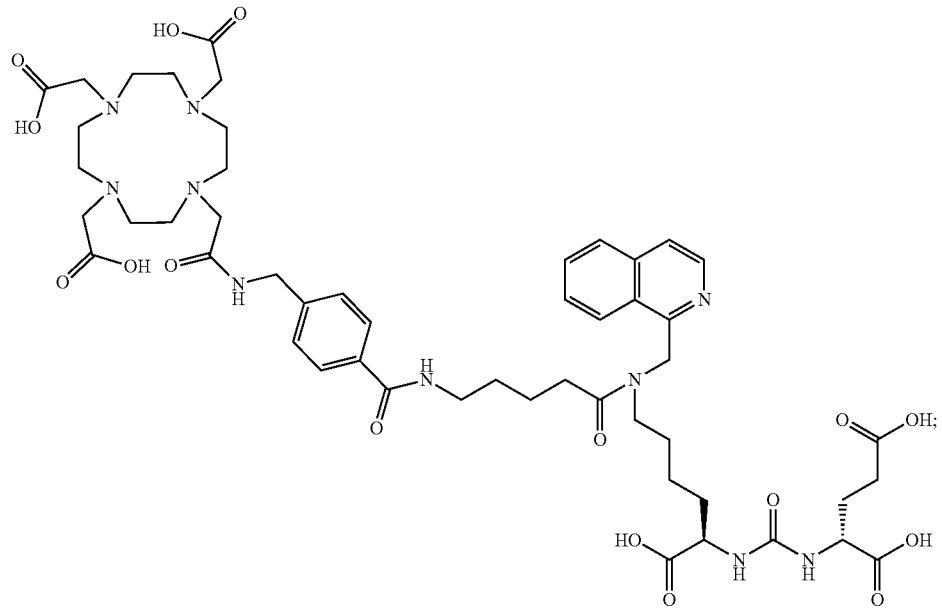
P5
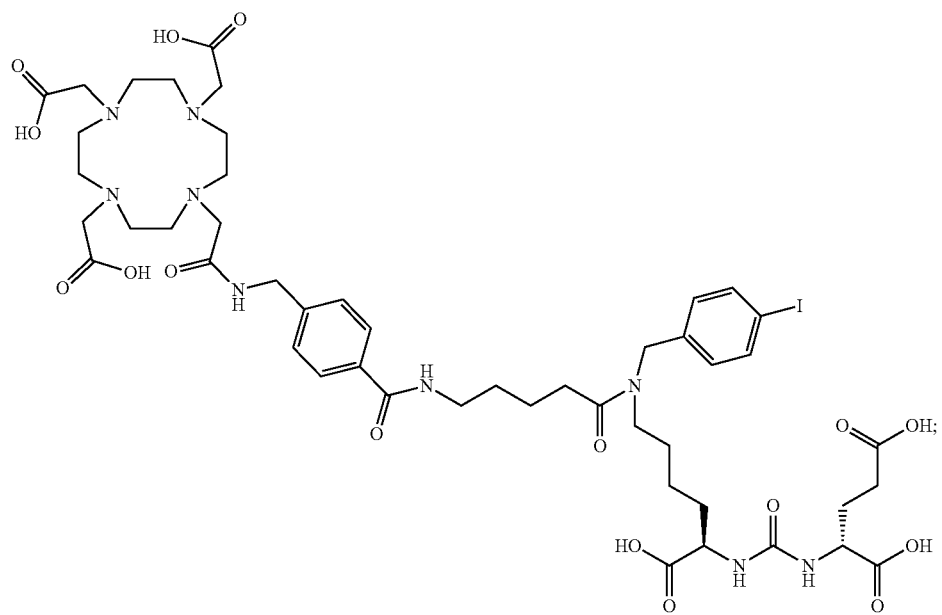
P6

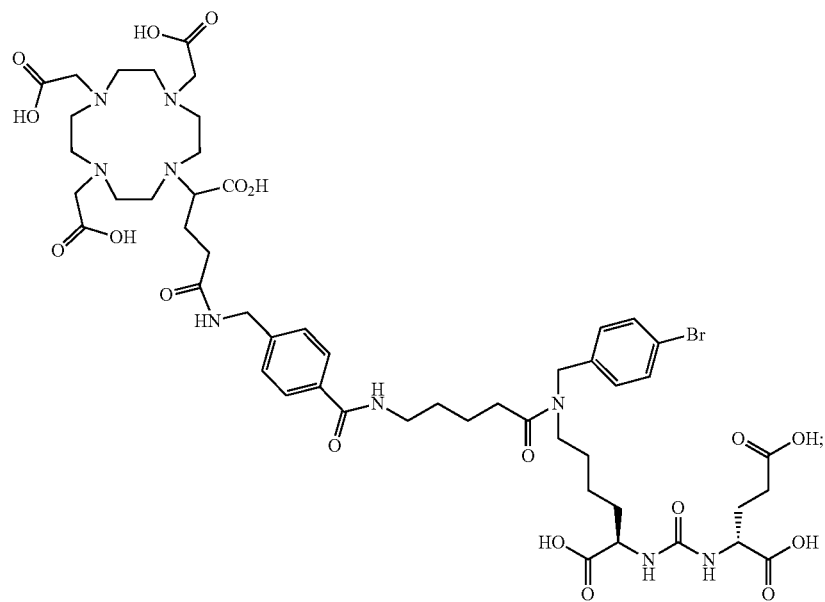
P7
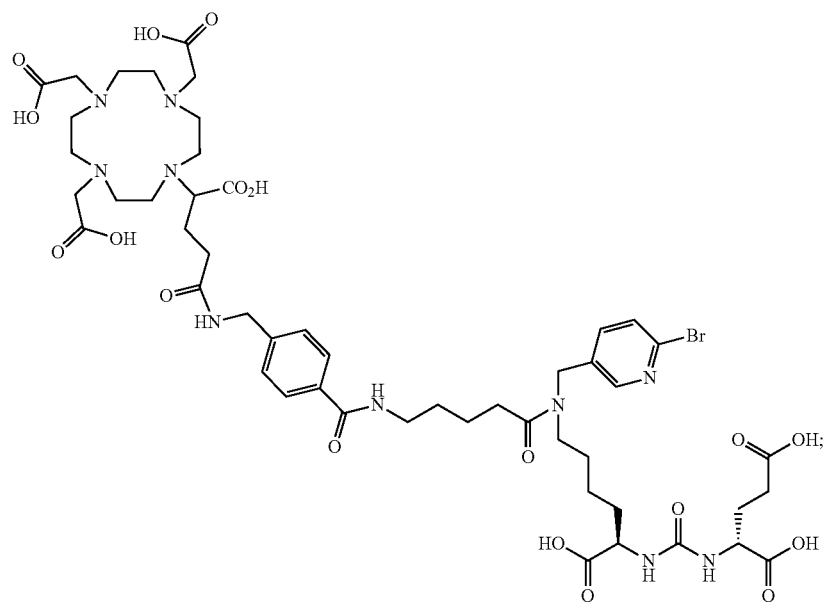
P7

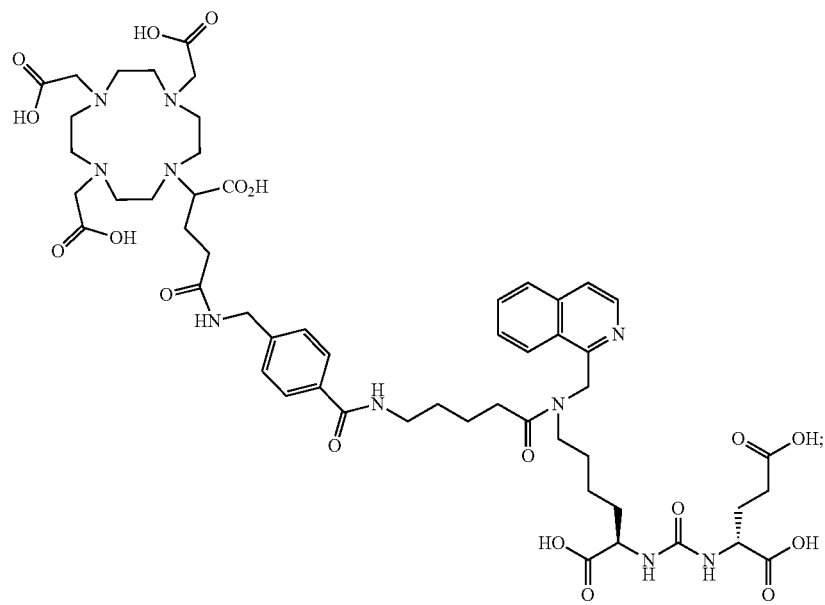
P7
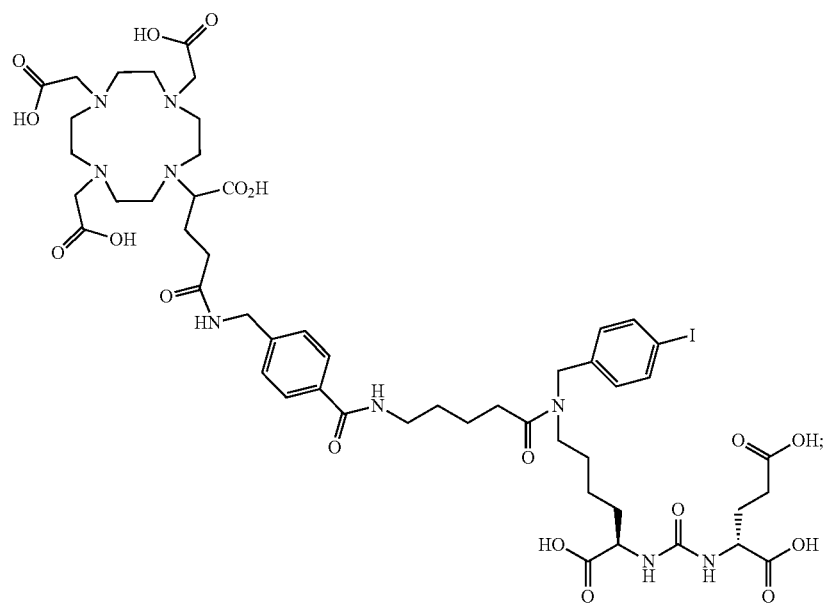
P8

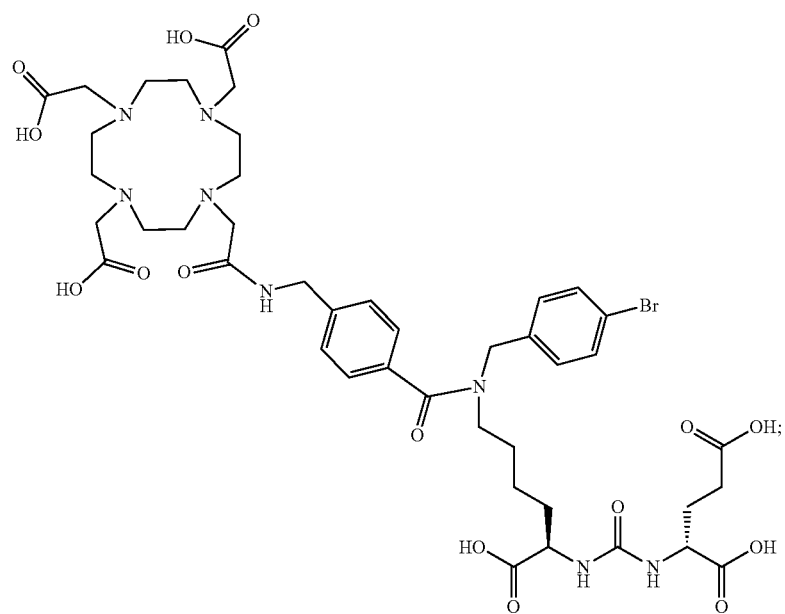
P9
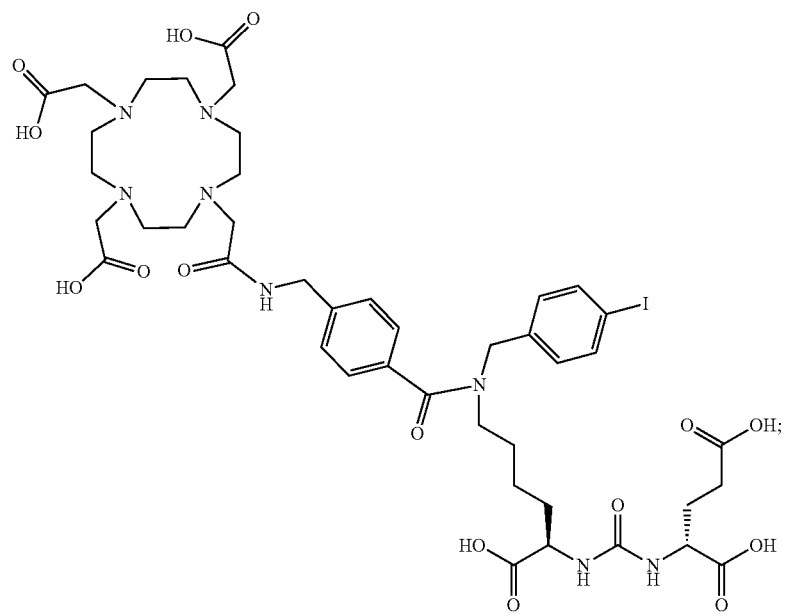
P10

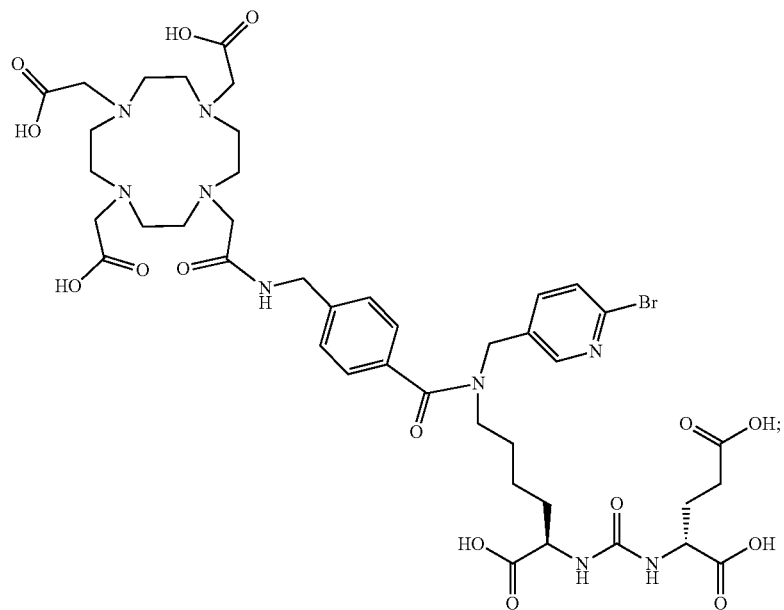
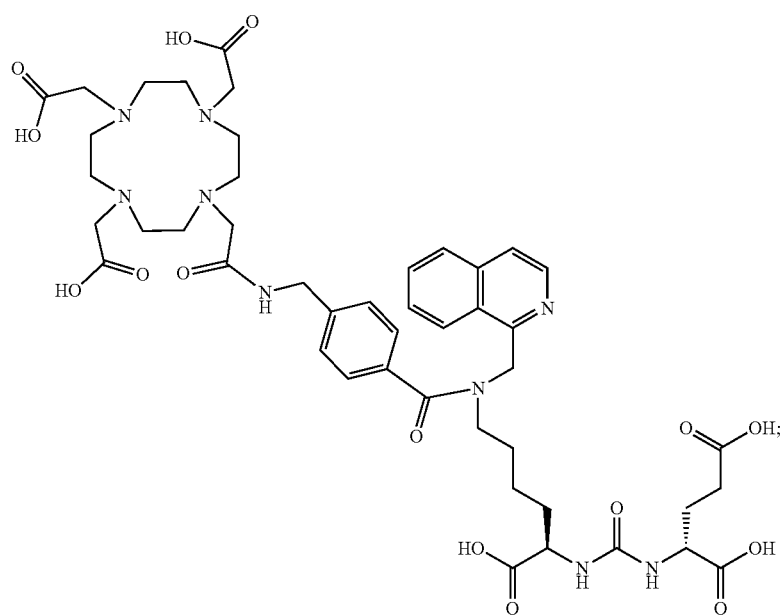

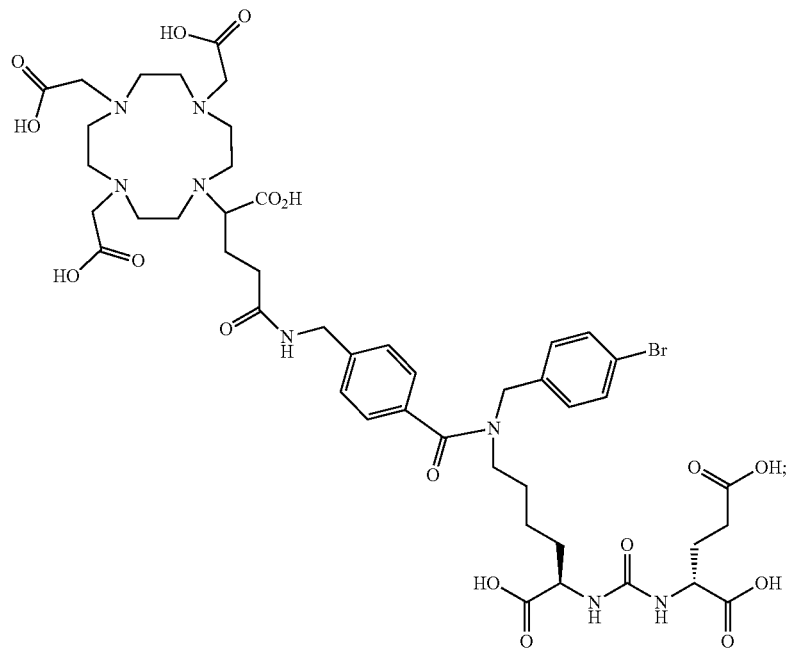
P11
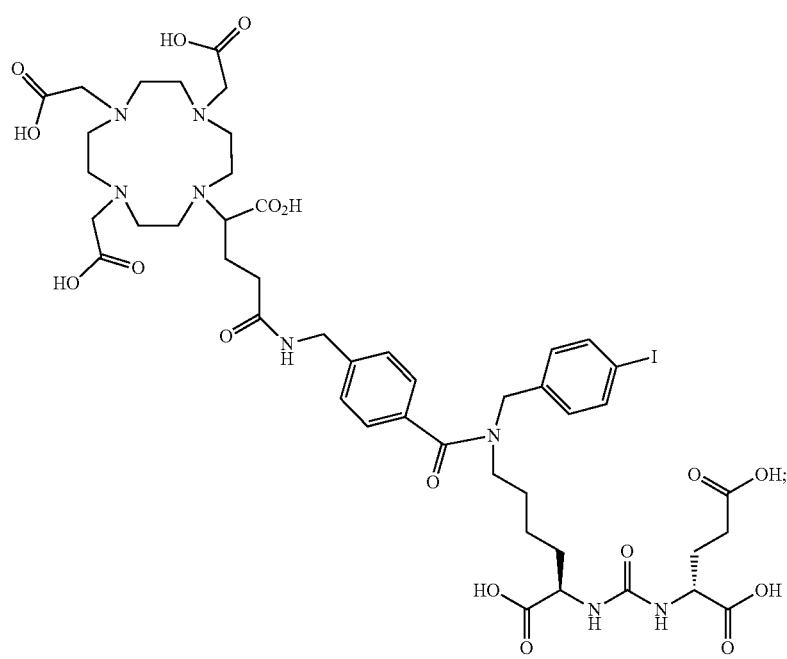
P12

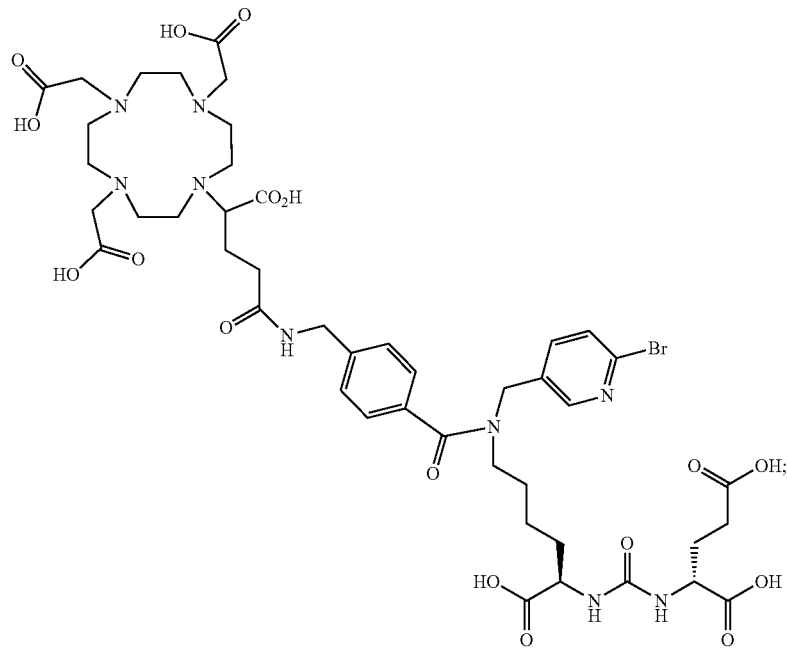
P11
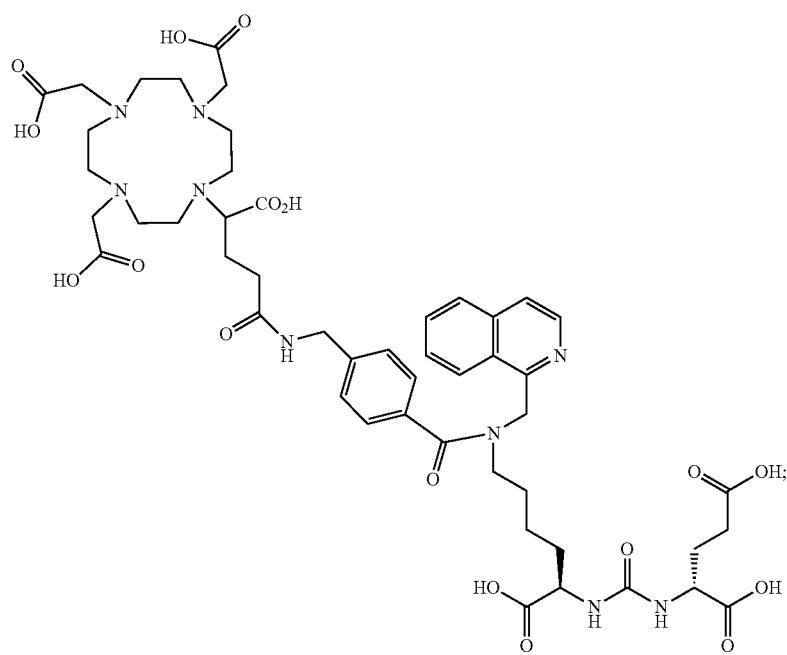
P11

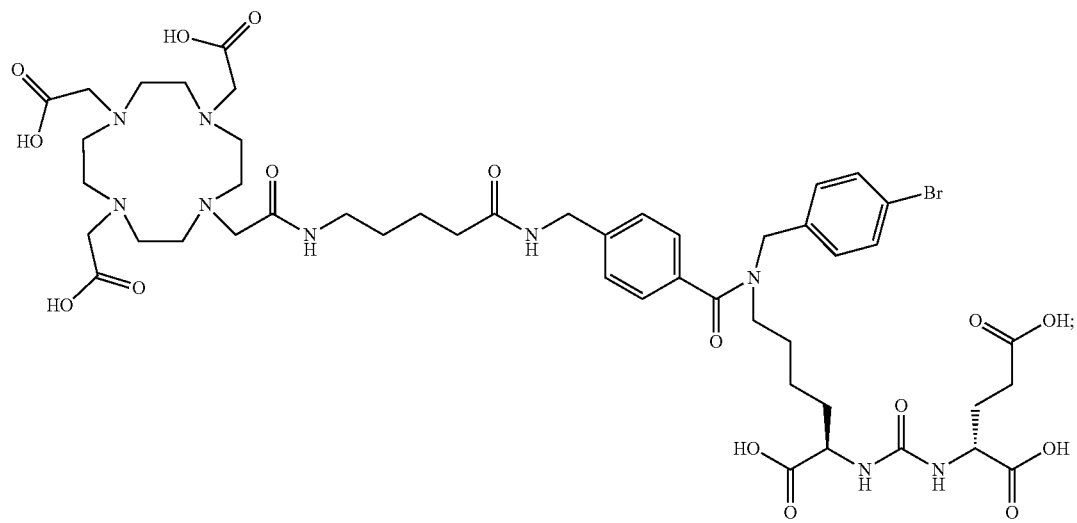
P13
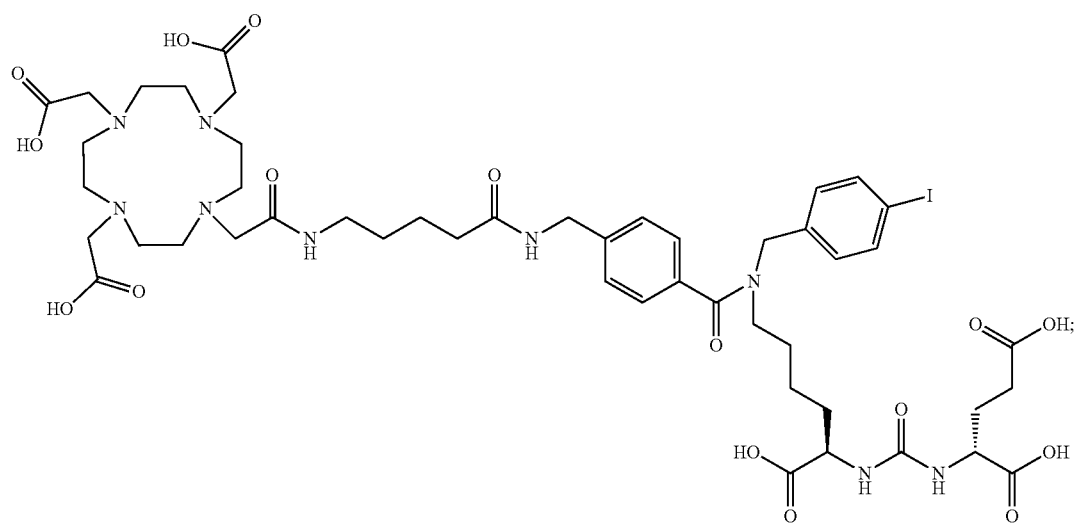
P14
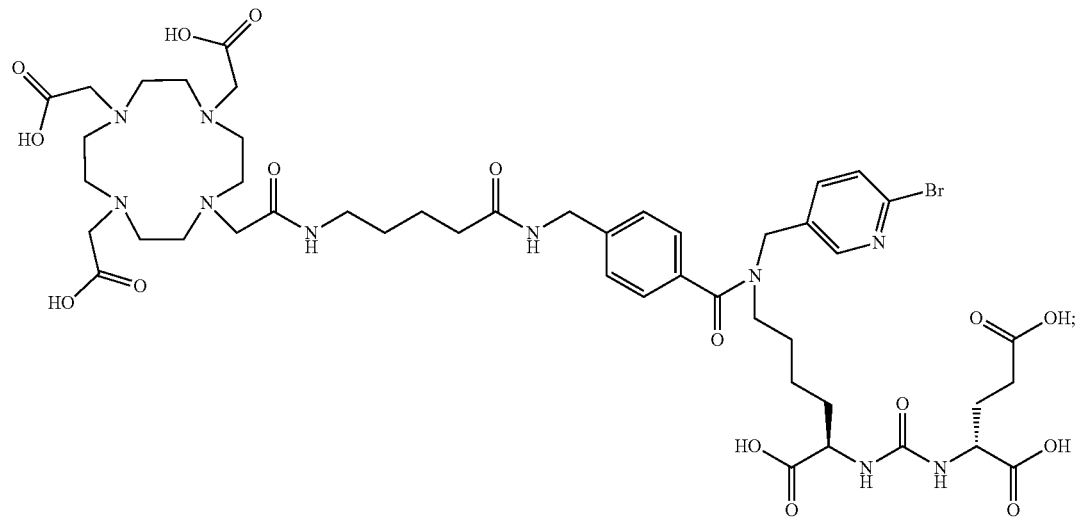
P13

P13
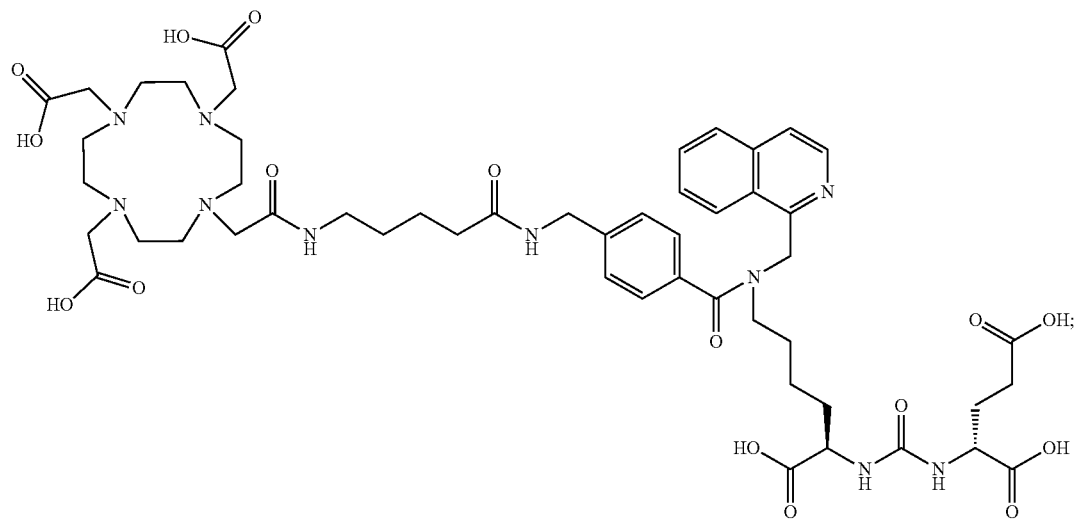
P15
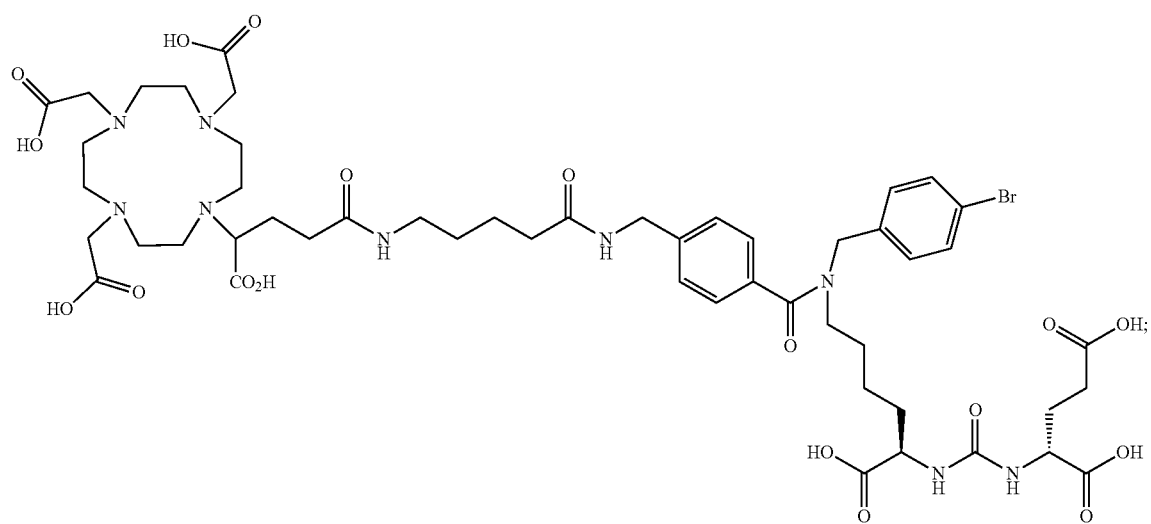
P16
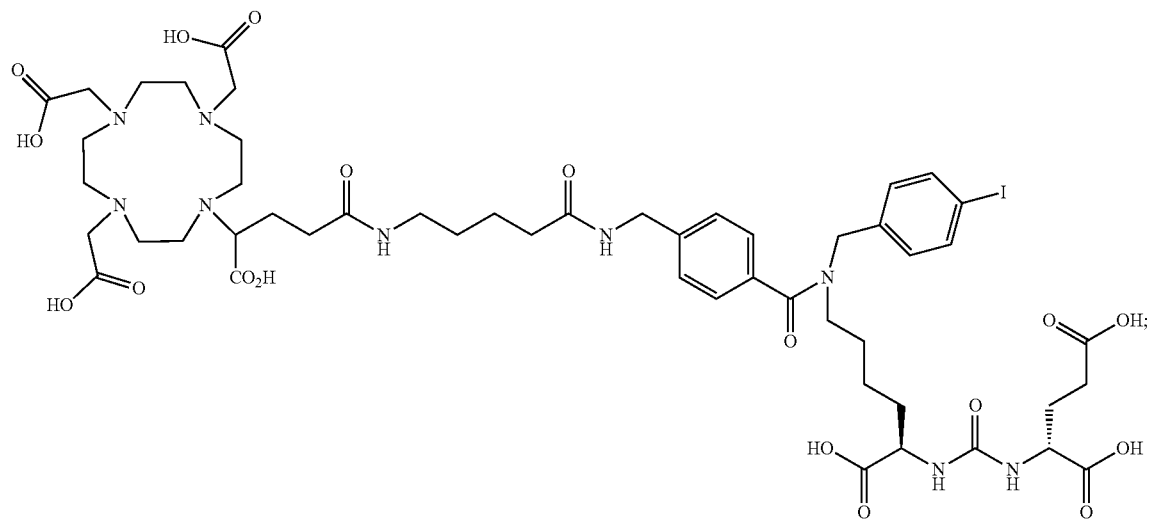

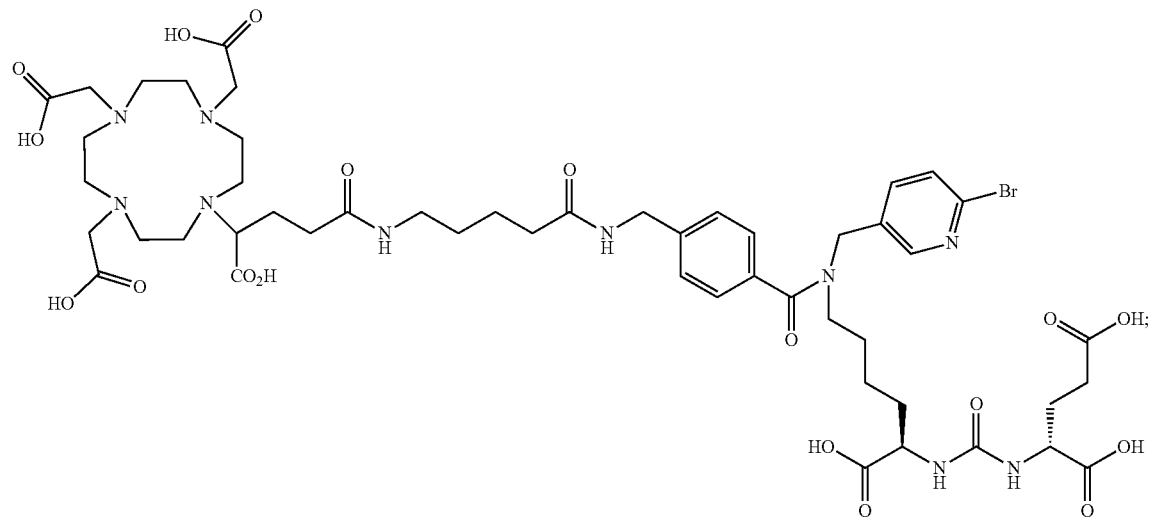
P15
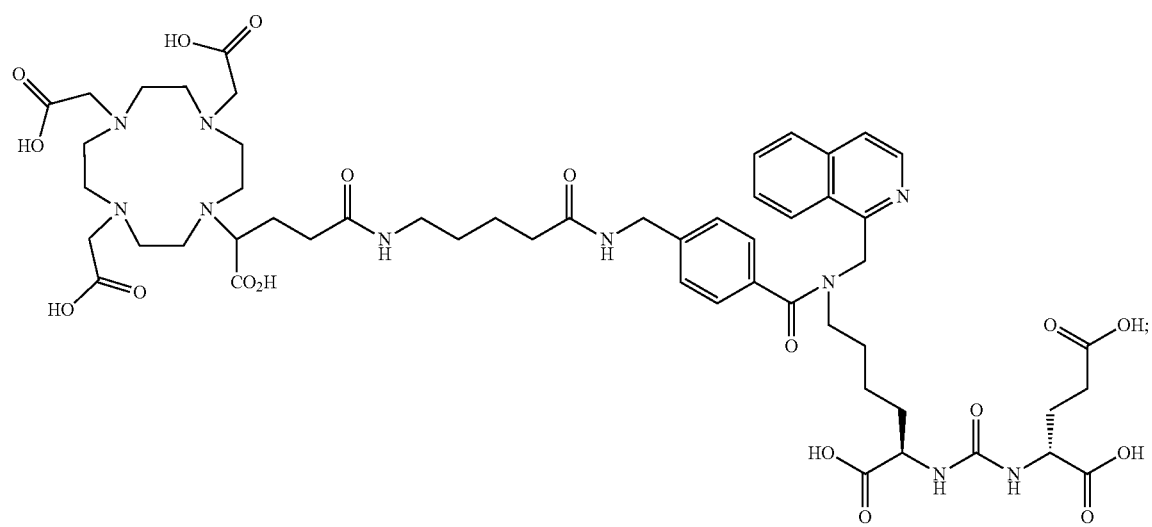
P15
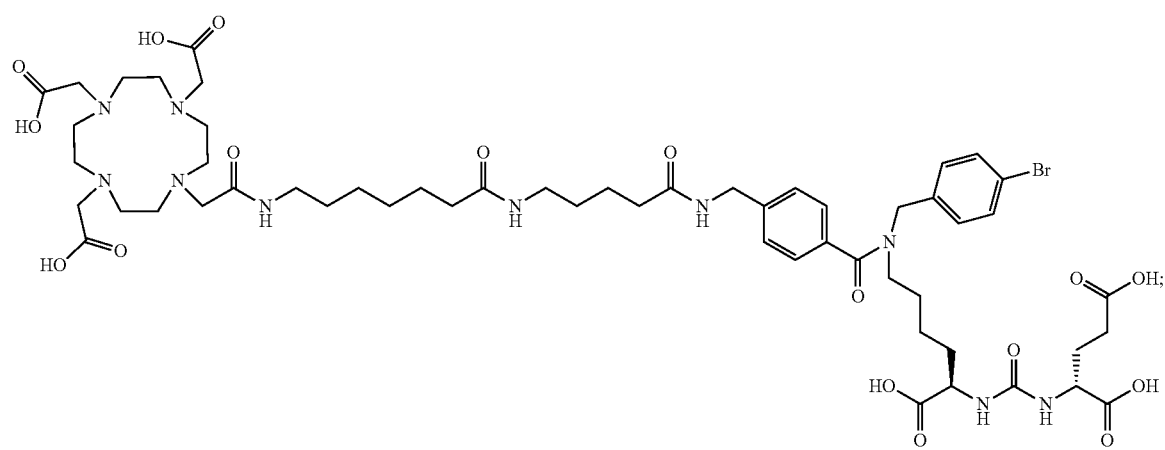
P17

-continued
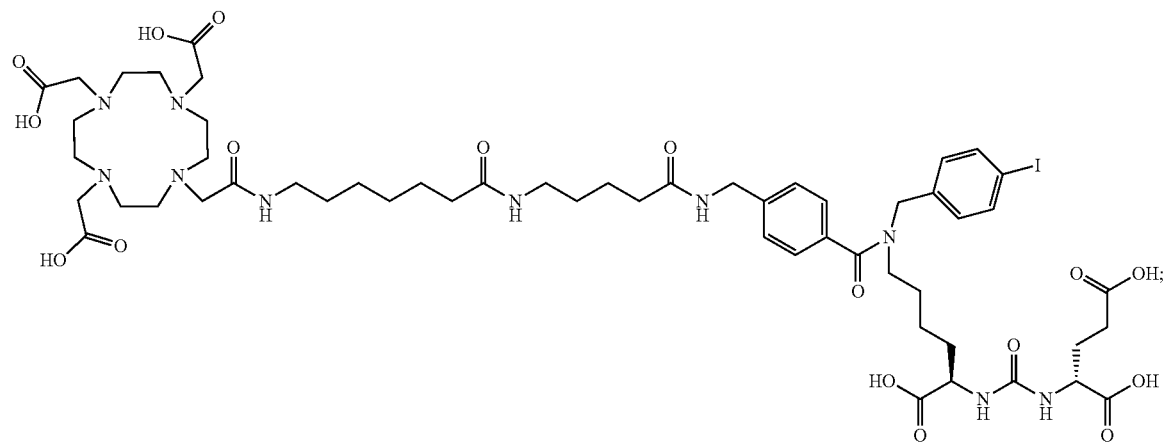
P18
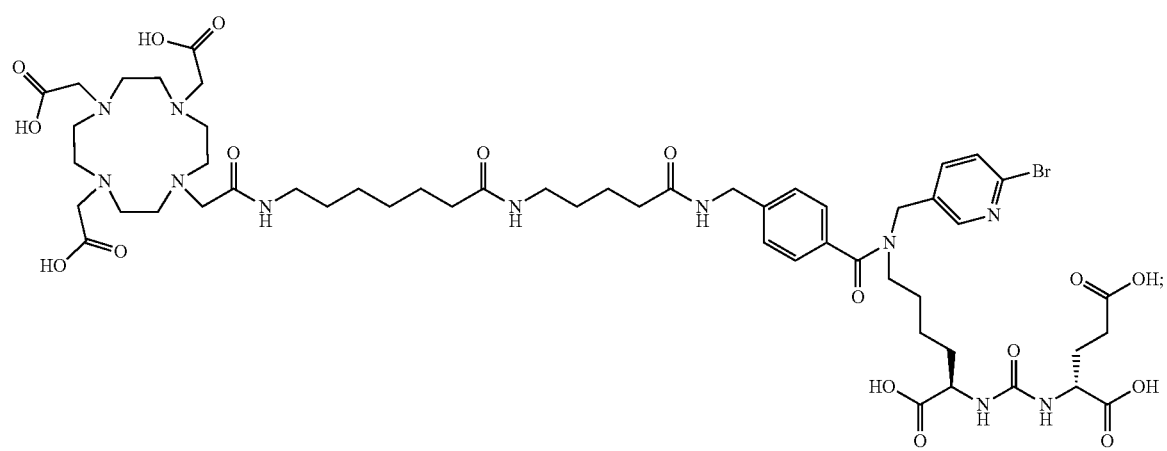
P17
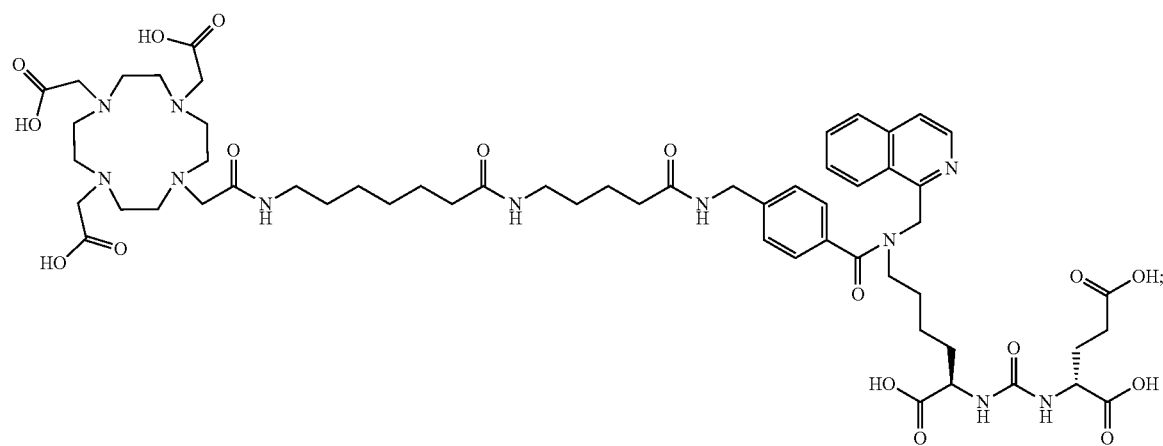
P17

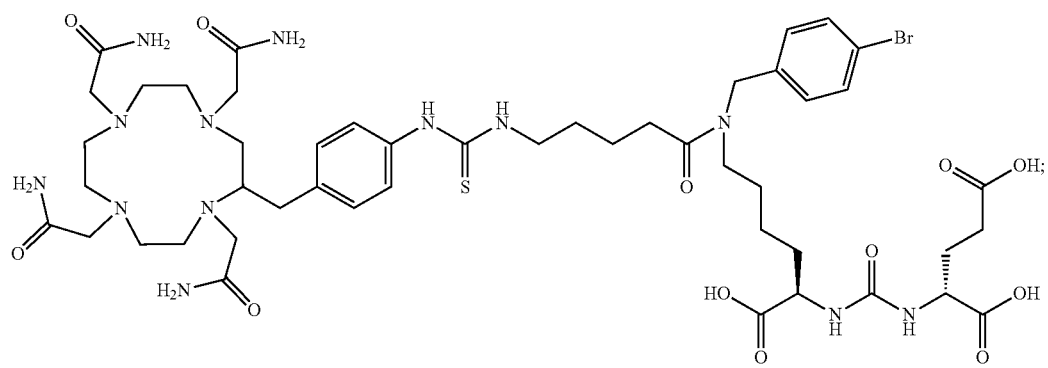
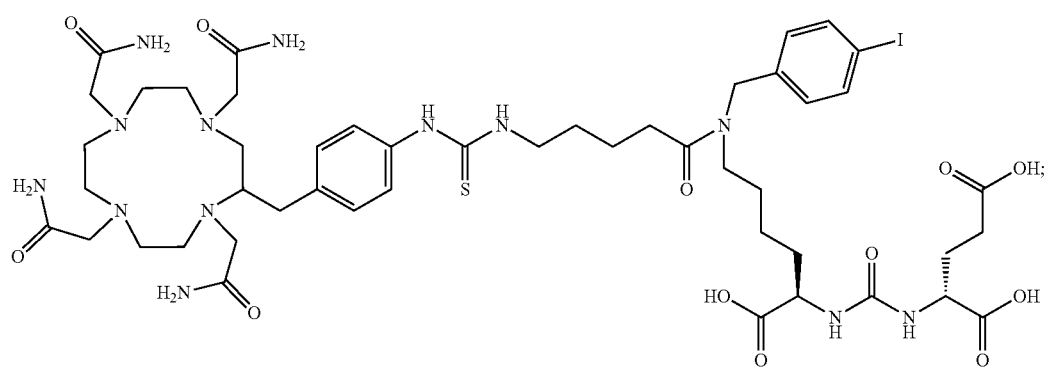
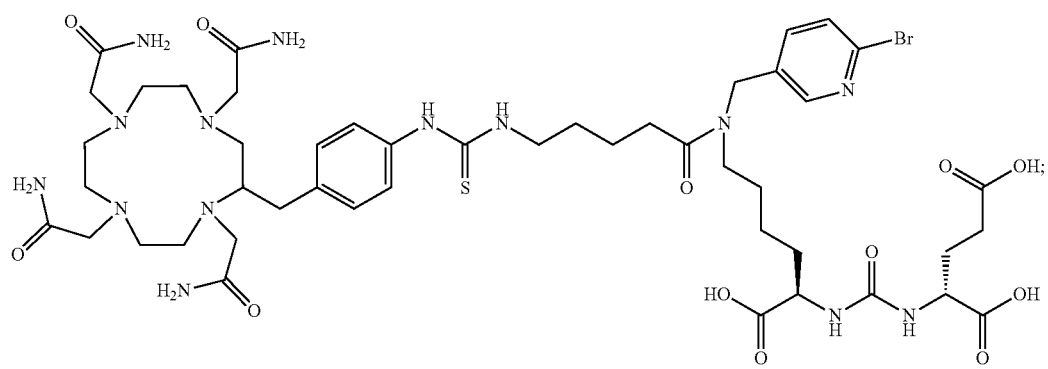
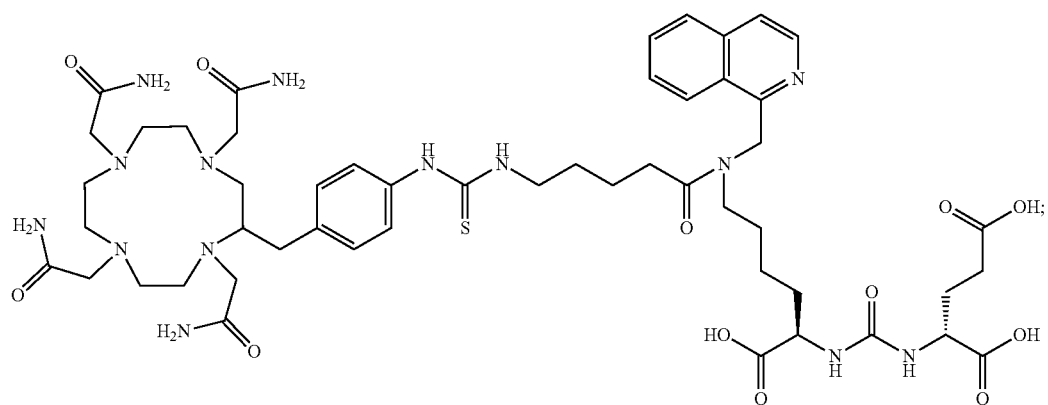

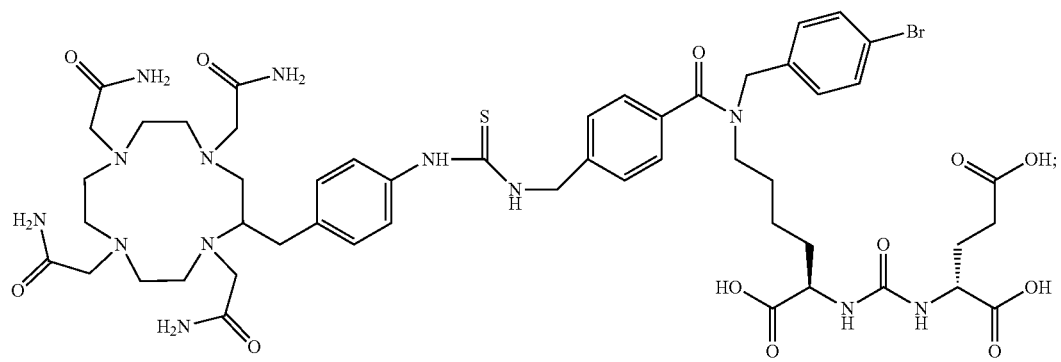
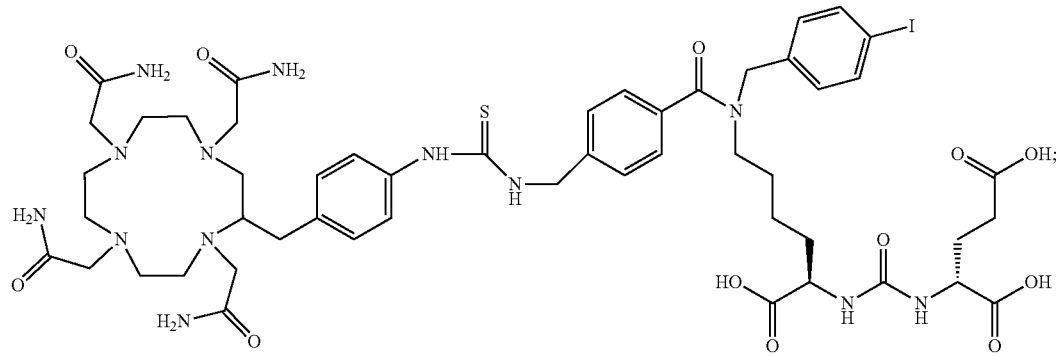
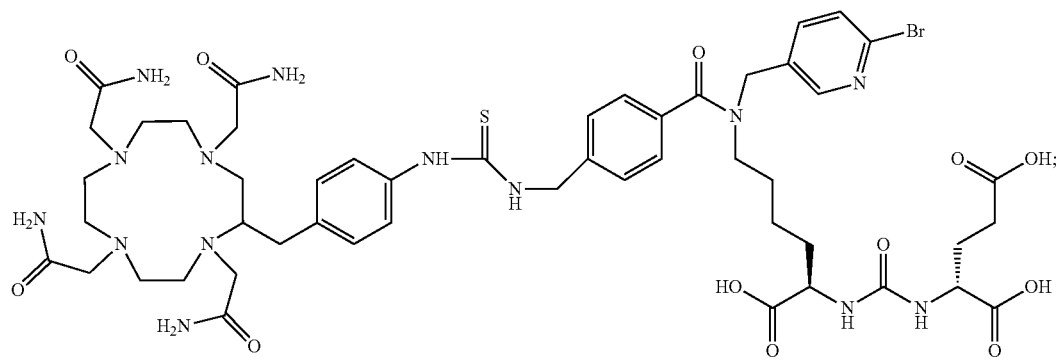
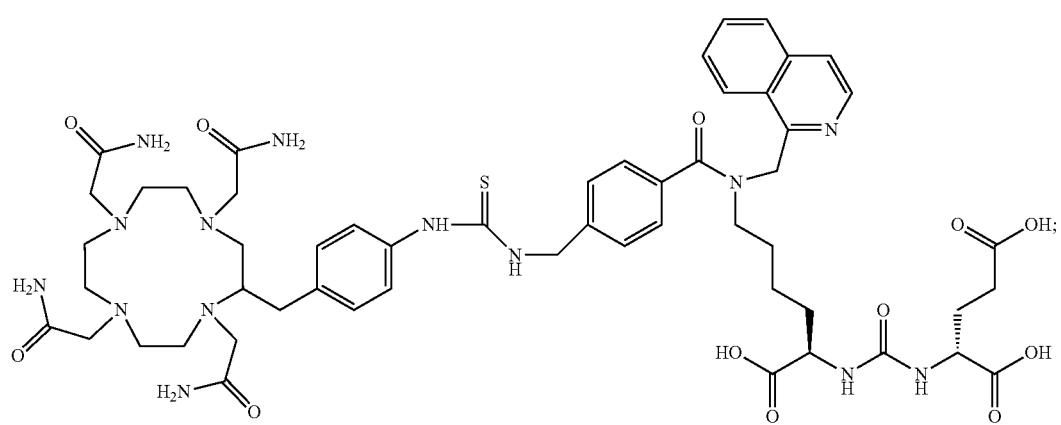

-continued
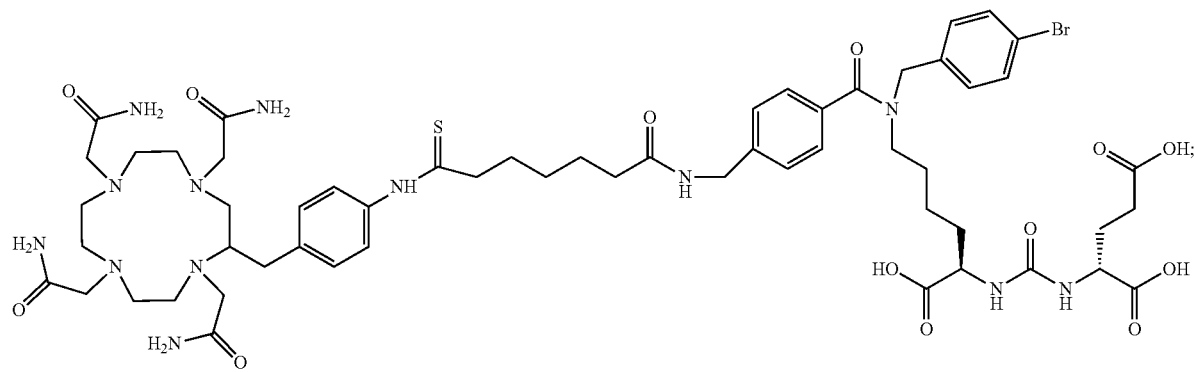
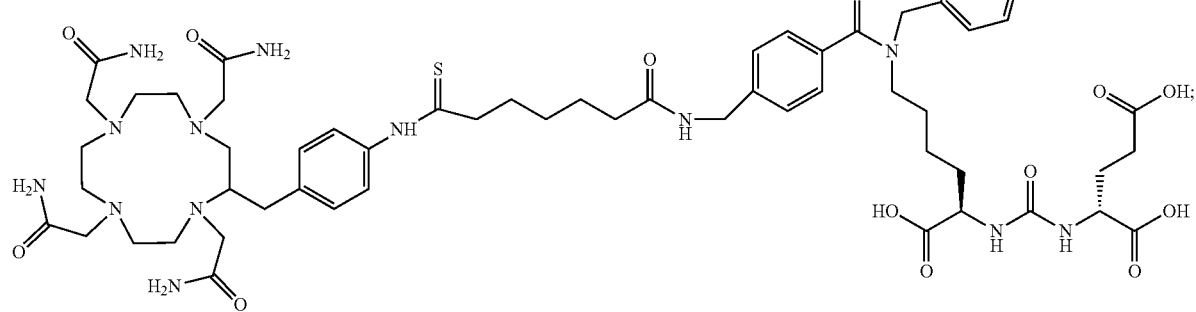
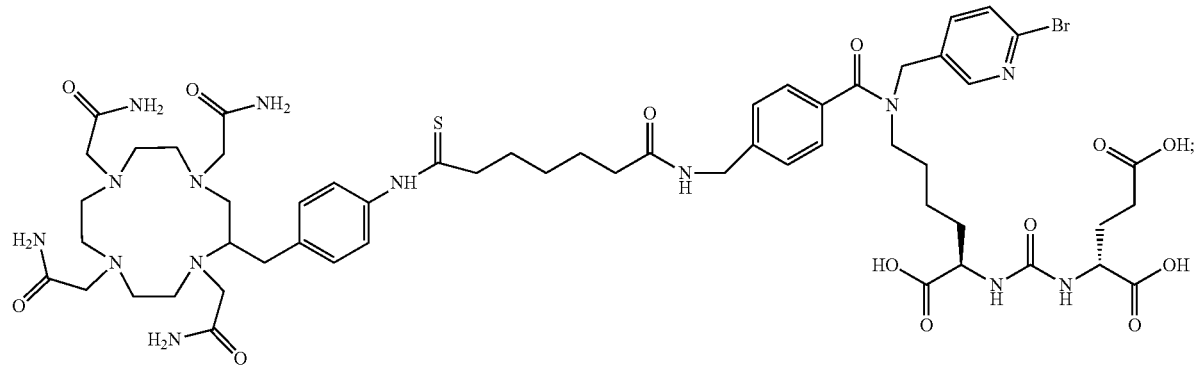
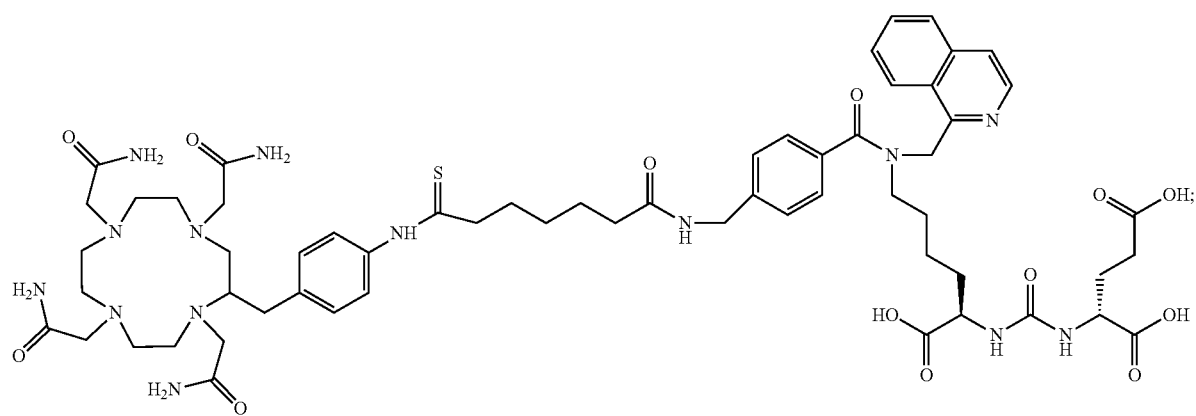

-continued

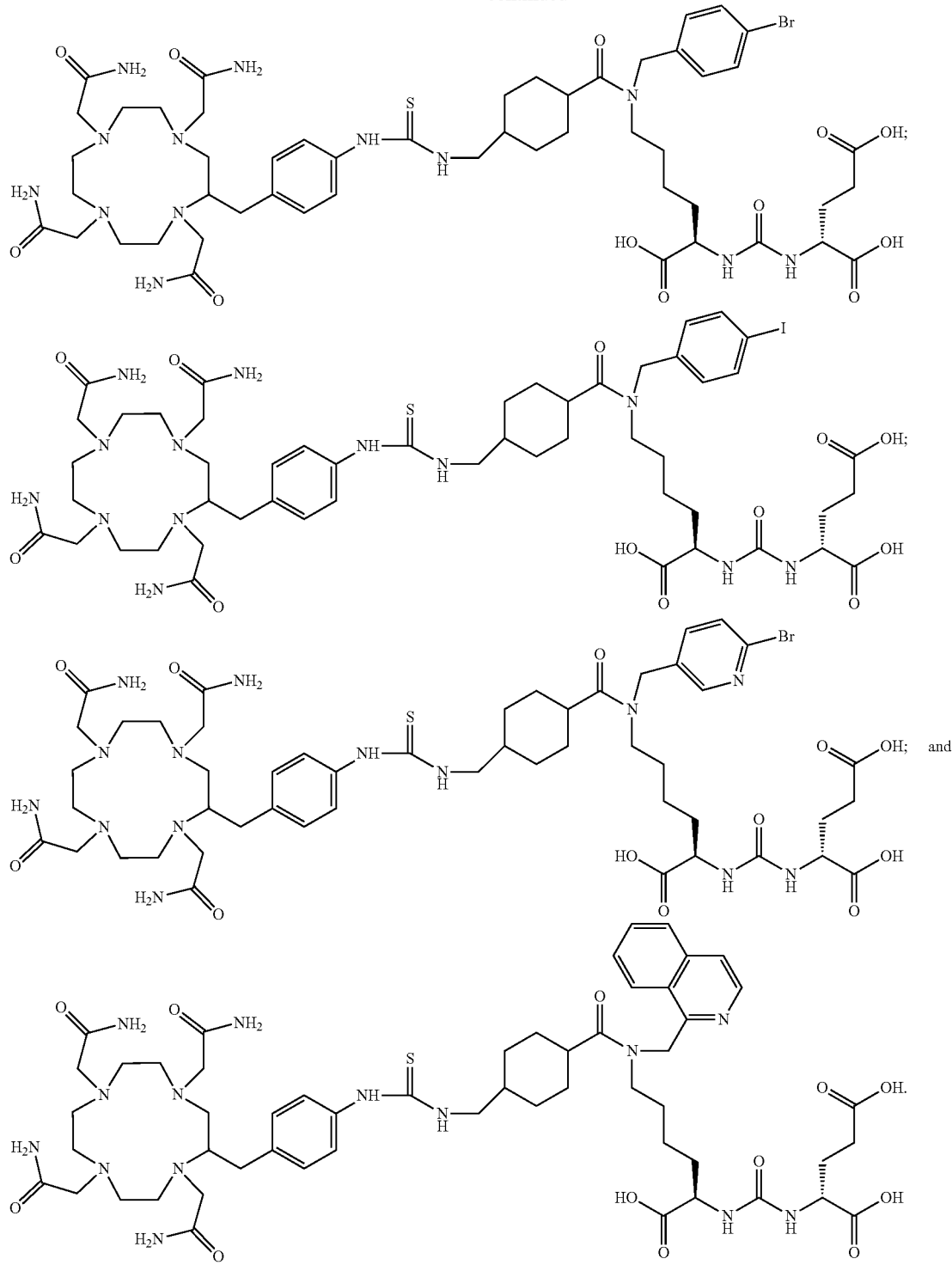

In other embodiments, the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In some other embodiments, the one or more PSMA-expressing tumor or cell is a prostate tumor or cell.

In other embodiments, the one or more PSMA-expressing tumors or cells is in vitro, in vivo or ex-vivo. In yet other embodiments, the one or more PSMA-expressing tumor or cell is present in a subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In yet some other embodiments, the method results in inhibition of the tumor growth.

C. Methods of Using Compounds of Formula (I) for Imaging One or More One or More PSMA-Expressing Tumors or Cells In other embodiments, the presently disclosed subject matter provides a method for imaging one or more prostate-specific membrane antigen (PSMA) tumors or cells, the method comprising contacting to the one or more tumors or cells, an effective amount of a compound of Formula (I) and making an image, the compound of Formula (I) comprising:

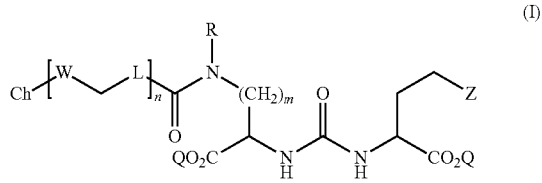

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1, 2, and 3; Ch is a chelating agent that comprises a radiometal suitable for imaging; and pharmaceutically acceptable salts thereof.

D. Kits

In yet other embodiments, the presently disclosed subject matter provides a kit comprising a compound of Formula (I).

In certain embodiments, the kit provides packaged pharmaceutical compositions comprising a pharmaceutically acceptable carrier and a compound of the invention. In certain embodiments the packaged pharmaceutical composition will comprise the reaction precursors necessary to generate the compound of the invention upon combination with a radio labeled precursor. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

E. Pharmaceutical Compositions and Administration

In another aspect, the present disclosure provides a pharmaceutical composition including a compound of Formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrosulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{25}$—S(O)—CH$_3$, —CH$_2$—CH$_2$—S(O)$_2$—CH$_3$, —CH=CH—O—CH$_3$, —Si(CH$_3$)$_3$, —CH$_2$—

CH=N—OCH$_3$, —CH=CH—N(CH$_3$)— CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

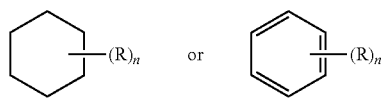

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

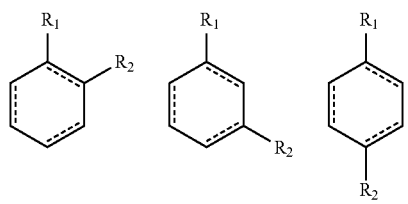

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl," and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR"'—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A—(CH$_2$)$_r$B—, wherein A and B are independently —CRR'—, —O—, —NR—, —S—, —S(O)—, —S(O)$_2$—, —S(O)$_2$NR'— r a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl)acetyl- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

The term "protecting group" in reference to compounds of formula (I) refers to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Representative examples of protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Overview

The use of PSMA binding ureas conjugated to chelated radiometals via various linking groups for imaging and possible radiotherapy of PSMA expressing tumors have been previously reported in several patent applications and publications (Tykvart et al. (2015) *Journal of medicinal chemistry* 58, 4357-63; Banerjee et al. (2015) *Journal of nuclear medicine* 56, 628-34; Benesova et al. (2015) *Journal of nuclear medicine* 56, 914-20; Weineisen et al. (2014) *EJNMMI Res* 4, 1-15; WO 2009002529 A2; WO 2009070302 A1). A new class of high affinity binding agent has been prepared by modifying the urea linker at epsilon amine position with p-Br-benzyl group. Structures of the presently disclosed compounds are shown in FIG. 1.

Without wishing to be bound to any one particular theory, it is believed that radiometal-chelated Glu-Lysine urea-based theranostic agents targeting prostate-specific membrane antigen (PSMA), when modified with p-Br-benzyl group on the epsilon amino group of lysine of Lys-Glu-urea moiety, demonstrate high binding affinity for PSMA and high uptake in PSMA-expressing tumors and low renal uptake in standard mouse model of prostate cancer. One embodiment, $^{177}$Lu-1, showed significant radiotherapeutic efficacy, about 50% remission of PSMA+ PC3 tumor bearing mice.

Example 2

Material and Methods

Chemical Synthesis of 1.

The synthesis of compound 1 is described in Scheme 1. Bromobenzaldehyde (121.0 mg, 0.654 mmol) was slowly added to a stirred solution of Boc-protected urea, 4, (300.0 mg, 0.615 mmol) in 5 ml of methanol at ice-cold bath and allowed to warm to room temperature. After one hour, sodium cyanoborohydride (158.0 mg, 2.5 mmol) was added and the reaction was left to stir overnight. Crude reaction mixture was evaporated, redissolved in dichloromethane, purified by normal phase silica chromatography (95:5, methylene chloride:methanol), and dried in vacuo to provide 5 in good yield. Yield: 80%. ESI-MS: 656.56 [M+H]$^+$, found: 656.5. TSTU (32.6 mg, 108 µmol), Boc-5-aminovaleric acid (23.5 mg, 108 µmol), and DIPEA (37.7 µL, 216 µmol) were dissolved in 300 µL DMF and stirred at room temperature. After one hour, compound 5 (71.0 mg, 108 µmol) was added with three rinses of DMF (50 µL each). The reaction mixture was stirred for four hours and stored at 4° C. overnight. Crude reaction mixture was purified by semi-preparative HPLC on C s column (40% water (0.1 TFA)/60% ACN (0.1 TFA)/for 5 min, 60-90% over 20 minutes. R$_t$ 21 minutes. Purified fractions were combined, evaporated, and dried under high vacuum for 10 minutes. ESI-MS: 572.44 [M+H]+, found: 572.4. Compound 6 was dissolved in dichloromethane (1.5 mL) and chilled in an ice bath. After equilibration, TFA (1.5 mL) was added and the mixture was stirred for 3 hours allowing to warm to room temperature in the process. Mixture was spurge to dryness under a nitrogen stream, dissolved in water, and lyophilized to yield 31.8 mg of compound 7.Yield: 54 µmol, 54%. p-SCN-bn-DOTA (12.2 mg, 17.7 µmol) was added to a stirred solution of 6 (12.2 mg of TFA salt) and DIPEA (15.2 µL, 87.0 µmol) in DMSO (130 µL) equilibrated to 40° C. Reaction mixture was stirred at 40° C. for four hours and stored at 4° C. overnight. Reaction mixture was purified by reverse phase HPLC (hold 20% ACN for 5 min, then 20-40% over 19 minutes). Rt approximately 12 minutes. Purified fractions were combined, rotoevaporated to decrease volume, and then lyopholized. ESI-MS: 1138.37 [M+H]$^+$, found: 1138.5. The compound 1 was further purified by HPLC with gradient method The HPLC method is a gradient method containing a mobile phase 88% water (containing 0.1% TFA) and 22% CH$_3$CN (0.1% TFA) for 1-5 min followed by 0-5 min water 88% water (containing 0.1% TFA) and 12% CH$_3$CN (0.1% TFA), and from 5-25 min 88% water to 44% water and 12% acetonitrile to 56% acetonitrile with flow rate 8 mL/min.

Chemical Synthesis of 2.

This compound was synthesized by using the same intermediate 7 and coupled with commercially available DOTA-NHS ester. ESI-MS: 974.86. [M+H]$^+$, found: 974.5 Chemical Synthesis of 3. This compound was synthesized by using the intermediate 4 and coupled with commercially available Boc-5-aminovaleric acid and DOTA-NHS ester. ESI-MS: 970.05[M+H]$^+$, found: 970.1.

Radiolableing of $^{177}$Lu-1.

1.0 l of $^{177}$LuCl$_3$ (1 mCi) in 0.1 N HCl was added 70 µl NH$_4$OAc buffer (0.2 M, pH 4) and to 5 µl of 2 mM in 0.2M NH$_4$OAc. The pH of the mixture was about 4.0. The mixture was kept at 80° C. for an hour and purified by HPLC. The HPLC method is a gradient method containing a mobile phase 77% water (containing 0.1% TFA) and 23% CH$_3$CN (0.1% TFA) for 1-5 min followed by 5-25 min water, 77% to 57% and acetonitrile, 23% to 43%; 25.01-30 min water 5% to 5% and acetonitrile, 95% to 95%, 30.01 to 37 min, water 77% to 77% and acetonitrile, 23% to 23%. Flow rate: 1.0 ml/min; X: 200 nm, and a C$_8$ column (25×4.6 mm), Varian microsob-MV 100-5. Radiolabeled $^{177}$Lu-1 was eluted at 17.1-20 min whereas unlabeled chelating agent was eluted at 21-22 min.

The HPLC method was used to prepare $^{177}$Lu-2 and $^{177}$Lu-3: The HPLC method is a gradient method containing a mobile phase 88% water (containing 0.1% TFA) and 22% CH$_3$CN (0.1% TFA) for 1-5 min followed by 5-27 min water, 88% to 75% and acetonitrile, 12% to 25%; 27.01-32 min water 5% to 5% and acetonitrile, 95% to 95%, 32.01 to 37 min, water 88% to 18% and acetonitrile, 12% to 22%. Flow rate: 1.0 ml/min; X: 200 nm, and a C, column (25×4.6 mm), Varian microsob-MV 100-5. Radiolabeled $^{177}$Lu-2 was eluted at 13.1-15.0 min whereas unlabeled chelating agent was eluted at 16-17 min. Radiolabeled $^{177}$Lu-3 was eluted at 13.1-15.0 min whereas unlabeled chelating agent was eluted at 10-12 min a18-20 min and the unlabeled agent came 14-16 min.

Scheme 1. Synthesis of compound 1

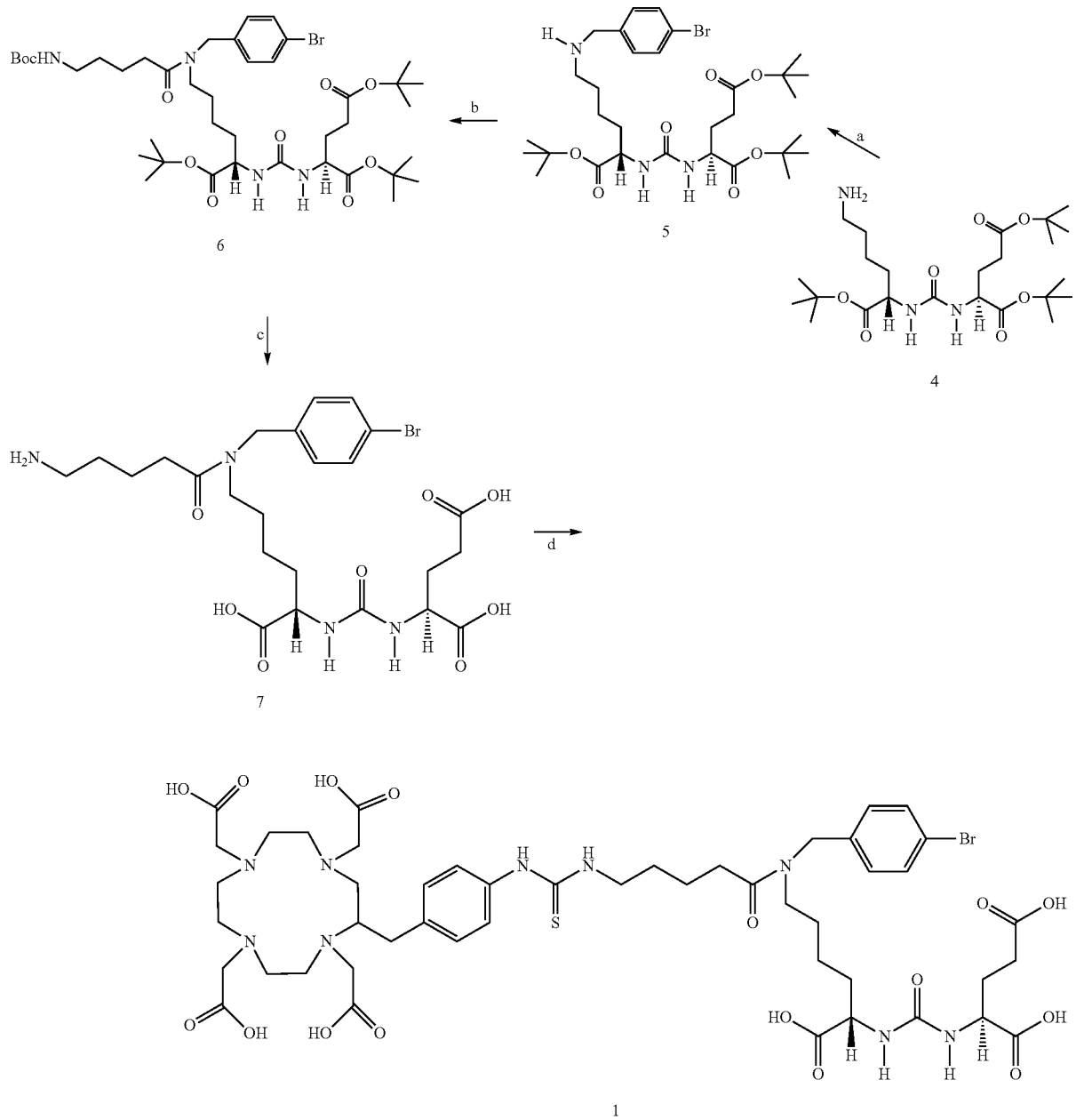

a. 4-Bromobenzaldehyde, NaBH$_3$CN, MeOH, 1% acetic acid;
b. BocNH(CH$_2$)$_4$CO$_2$H, HATU, DIEA, DMF; c. TFA/CH$_2$Cl$_2$;
d. DOTA—Bn—SCN, DMSO, DIEA

Example 3

Results and Discussion

Chemical and Radiochemical Syntheses and Characterization.

p-Bromobenzyl group modified of Glu-Lys urea (2) was prepared by reductive alkylation of 2 with p-Bromobenzaldehyde in presence of sodium cyanoborohydride in methanol in good yield to provide 4 following a literature procedure (Tykvart et al. (2015) *Journal of medicinal chemistry* 58, 4357-63). A small aliphatic linker, Boc-5-aminovaleric acid was coupled on the same ε-Lys amine of 4 followed by removal of BOC group and conjugation with commercially available DOTA-Bn-SCN with 6 to provide 1 in moderate yield. The compound 2 was synthesized by using DOTA-NHS ester as the chelating agent and coupling with the same intermediate 6. Compound 3 was synthesized as a control agent, without any p-Bromobenzyl group. All three agents were radiolabeled with $^{177}$Lu in good yield and purity at pH 4 in ammonium acetate buffer at 80° C. Binding affinities of the new compounds are listed in Table 1. Both 1 and 2 modified with p-Bromo-benzyl group showed higher binding affinity compared to 3.

TABLE 1

Binding affinities of the representative agents

| Compound | 1 | 2 | 3 | ZJ43 (for 2) | ZJ43 (for 1, 3) |
|---|---|---|---|---|---|
| IC50 (nM) | 0.57 nM | 0.64 nM | 2.16 nM | 1.91 nM | 2.7 nM |
| Ki (nM) | 1.15 nM | 1.28 nM | 0.43 nM | 0.38 nM | 0.66 nM |
| ClogD | −4.6 | −3.5 | −4.1 | nd | nd |
| LogPoct/water | −3.0 | −3.53 | −3.2 | nd | nd |
| Polar Surface area | 359 | 327 | 368 | nd | nd |

Cell-Binding Properties.

The $^{177}$Lu agents were further evaluated in cells and animals using standard isogenic cell lines PSMA+ PC3 PIP and PSMA-negative PC3 flu cells. Both $^{177}$Lu-1 and $^{177}$Lu-2 demonstrated higher uptake in PSMA+ PC3 cells compared to $^{177}$Lu-3. Further internalization studies revealed that $^{177}$Lu-1 has higher nearly 2-fold higher internalized activity compared to $^{177}$Lu-3. All three agents showed significantly low uptake in PSMA-negative PC3 flu cells. The $^{177}$Lu-1 was further evaluated for treatment efficacy in a clonogenic assay and compared with previous lead compound SR6 (Banerjee et al. (2015) *Journal of nuclear medicine* 56, 628-34) and agents in the clinical trials including $^{177}$Lu-PSMA-617 (Benesova et al. (2015) *Journal of nuclear medicine* 56, 914-20) and $^{177}$Lu PSMA-I&T (Weineisen et al. (2014) *EJNMMI Res* 4, 1-15). $^{177}$Lu-1 was able to produce about 100% cell killing efficacy using 10 µCi dose in PSMA+ PC3 PIP cells whereas no significant toxicity was seen for PSMA-PC3 flu cells.

TABLE 2

Cell binding properties of the agents at 4 h incubation (values are expressed as percent incubated dose per one million cells) (n = 3)

| Compound | $^{177}$Lu-1 | $^{177}$Lu-2 | $^{177}$Lu-3 |
|---|---|---|---|
| Cell uptake PSMA + PC3 PIP | 42.60 | 40.6 | 24.50 |
| Cell uptake PSMA − PC3 flu | 0.09 | 0.12 | 0.05 |
| Internalization (cell lysate) | 15.88 | n.d. | 8.75 |
| Cell surface | 27.68 | n.d. | 12.50 |

Biodistribution.

In vivo tissue biodistribution studies were done for $^{177}$Lu-1 and $^{177}$Lu-2 and are listed in Table 3 and 4. $^{177}$Lu-1 showed higher uptake and retention in PSMA+ PC3 PIP tumor uptake than $^{177}$Lu-2. Significantly $^{177}$Lu-2 agent showed 5-fold lower renal uptake than $^{177}$Lu-1 and as shown in FIG. 3 tumor/kidney of the presently disclosed compounds were compared with previous lead $^{177}$Lu-SR6, $^{177}$Lu-PSMA-617 and $^{177}$Lu-PSMA-I&T. The PSMA+ PC3 PIP tumor-to-kidney ratio for $^{177}$Lu-2 was higher than $^{177}$Lu-1. Due to the higher tumor uptake and retention, $^{177}$Lu-1 was further evaluated for theranostic efficacy (imaging and therapeutic effect) in a pilot study using a small group of animals.

TABLE 3

In vivo tissue biodistribution of $^{177}$Lu-1, Values expressed as percent injected dose per gram ± standard deviation) (N = 4)

| Tissue | 2 h | 24 h | 48 h | 72 h |
|---|---|---|---|---|
| Blood | 0.68 ± 0.25 | 0.01 ± 0.01 | 0.00 ± 0.01 | 0.00 ± 0.04 |
| Heart | 0.28 ± 0.08 | 0.02 ± 0.05 | 0.01 ± 0.00 | 0.01 ± 0.00 |
| Lung | 1.12 ± 0.33 | 0.06 ± 0.01 | 0.04 ± 0.01 | 0.04 ± 0.02 |
| Liver | 0.39 ± 0.13 | 0.11 ± 0.01 | 0.09 ± 0.02 | 0.07 ± 0.00 |
| Stomach | 0.87 ± 0.63 | 0.04 ± 0.01 | 0.05 ± 0.04 | 0.04 ± 0.00 |
| Pancreas | 0.28 ± 0.09 | 0.02 ± 0.00 | 0.01 ± 0.01 | 0.01 ± 0.00 |
| Spleen | 3.76 ± 0.70 | 0.15 ± 0.05 | 0.08 ± 0.03 | 0.08 ± 0.02 |
| Fat | 0.35 ± 0.10 | 0.08 ± 0.15 | 0.01 ± 0.01 | 0.06 ± 0.07 |
| Kidney | 87.10 ± 25.99 | 1.65 ± 0.30 | 1.02 ± 0.58 | 0.62 ± 0.04 |
| Muscle | 0.68 ± 0.98 | 0.01 ± 0.00 | 0.00 ± 0.00 | 0.02 ± 0.02 |
| Sm. Int. | 0.51 ± 0.32 | 0.03 ± 0.01 | 0.02 ± 0.00 | 0.02 ± 0.01 |
| Sal. Gl | 1.09 ± 0.08 | 0.09 ± 0.02 | 0.05 ± 0.03 | 0.05 ± 0.02 |
| Bladder | 3.39 ± 2.78 | 0.31 ± 0.13 | 0.12 ± 0.07 | 0.06 ± 0.03 |
| PC-3 PIP | 55.04 ± 7.23 | 40.61 ± 7.00 | 27.00 ± 7.03 | 24.90 ± 2.27 |
| PC-3 Flu | 0.39 ± 0.03 | 0.10 ± 0.02 | 0.05 ± 0.01 | 0.06 ± 0.01 |

TABLE 4

In vivo tissue biodistribution of $^{177}$Lu-2, Values expressed as percent injected dose per gram ± standard deviation (N = 4)

| Tissue | 2 h | 24 h | 48 h |
|---|---|---|---|
| Blood | 0.81 ± 0.80 | 0.01 ± 0.01 | 0.00 ± 0.00 |
| Heart | 0.31 ± 0.19 | 0.02 ± 0.01 | 0.01 ± 0.01 |
| Lung | 0.39 ± 0.13 | 0.02 ± 0.00 | 0.02 ± 0.00 |
| Liver | 0.19 ± 0.05 | 0.04 ± 0.01 | 0.04 ± 0.00 |
| Stomach | 7.95 ± 4.17 | 0.03 ± 0.02 | 0.03 ± 0.01 |
| Pancreas | 0.19 ± 0.08 | 0.02 ± 0.02 | 0.01 ± 0.00 |
| Spleen | 1.10 ± 0.62 | 0.05 ± 0.02 | 0.04 ± 0.01 |
| Fat | 0.70 ± 0.54 | 0.11 ± 0.10 | 0.03 ± 0.04 |
| Kidney | 14.04 ± 8.19 | 0.73 ± 0.70 | 0.24 ± 0.07 |
| Muscle | 0.20 ± 0.05 | 0.01 ± 0.00 | 0.00 ± 0.00 |
| Sm. Int. | 2.02 ± 2.86 | 0.06 ± 0.09 | 0.02 ± 0.00 |
| Salivary gland | 0.89 ± 0.51 | 0.04 ± 0.02 | 0.02 ± 0.01 |
| Bladder | 3.48 ± 1.66 | 0.17 ± 0.06 | 0.08 ± 0.02 |
| Bone | 0.46 ± 0.10 | 0.10 ± 0.01 | 0.08 ± 0.02 |

TABLE 4-continued

In vivo tissue biodistribution of $^{177}$Lu-2, Values expressed as percent injected dose per gram ± standard deviation (N = 4)

| Tissue | 2 h | 24 h | 48 h |
|---|---|---|---|
| PC-3 PIP | 43.18 ± 5.32 | 24.76 ± 5.13 | 20.13 ± 3.35 |
| PC-3 Flu | 0.29 ± 0.02 | 0.08 ± 0.04 | 0.05 ± 0.01 |

Small Animal SPECT Imaging and Therapeutic Effect.

FIG. 4 shows SPECT imaging of $^{177}$Lu-1 during treatment studies for 1-8 days post-injection. A single dose of 3 mCi was injected via tail-vain injection in mice (n=10) bearing PSMA+ PC3 PIP tumor (size 3-5 mm). Saline was injected to another group of mice (n=10) for control study. Mice were monitored for body weight tumor size measure for two times per week. The control group of mice was euthanized after 4-8 weeks as the size of tumors over were >12 mm. For the treatment group, 50% of mice showed complete eradication of tumors. These mice were initially gone through an initial body weight which was regained after 2 weeks. Results are shown in FIG. 5. FIG. 6A and FIG. 6B demonstrated therapeutic efficacy (decrease in tumor volume) of $^{177}$Lu-1 compared to the control group using saline. Five mice are showed complete remission of the disease, and surviving for more than five months.

In summary, the radiometal-chelated Glu-Lysine urea-based theranostic agents targeting prostate-specific membrane antigen (PSMA) when modified with p-Br-benzyl group on the epsilon amino group of lysine of Lys-Glu-urea moiety demonstrated high binding affinity for PSMA and high uptake in PSMA-expressing tumors and low renal uptake in standard mouse model of prostate cancer. One representative compounds, $^{177}$Lu-1, showed significant radiotherapeutic efficacy, about 50% remission of PSMA+ PC3 tumor bearing mice.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

International PCT Patent Application Publication No. PCT/US2008/007947 to Pomper, M. G., Ray, S., Mease, R. C., Foss, C. for Labeled inhibitors of prostate specific membrane antigen (PSMA), biological evaluation, and use as imaging agents, published 2008 Dec. 31 (WO 2009/002529 A2);

International PCT Patent Application Publication No. PCT/US2008/013158 to Chandran S. S., Ray S., Denmeade S. R., Pomper M. G., Mease R. C. for Prostate specific membrane antigen targeted nanoparticles for therapy of prostate cancer, published 2009 Jun. 4 (WO 2009070302 A1);

International PCT Patent Application Publication No. PCT/US2010/028020 to Pomper M. G., Mease R. C.; Ray S., Chen Y. for PSMA-targeting compounds and uses thereof, published 2010 Sep. 23 (WO 2010108125 A2);

Banerjee, S. R., Foss, C. A., Pullambhatla, M., Wang, Y., Srinivasan, S., Hobbs, R. F., Baidoo, K. E., Brechbiel, M. W., Nimmagadda, S., Mease, R. C., Sgouros, G., and Pomper, M. G. (2015) Preclinical evaluation of 86Y-labeled inhibitors of prostate-specific membrane antigen for dosimetry estimates. *Journal of nuclear medicine* 56, 628-34;

Benesova, M., Schafer, M., Bauder-Wust, U., Afshar-Oromieh, A., Kratochwil, C., Mier, W., Haberkom, U., Kopka, K., and Eder, M. (2015) Preclinical Evaluation of a Tailor-Made DOTA-Conjugated PSMA Inhibitor with Optimized Linker Moiety for Imaging and Endoradiotherapy of Prostate Cancer. *Journal of nuclear medicine* 56, 914-20;

Tykvart, J., Schimer, J., Jancarik, A., Barinkova, J., Navratil, V., Starkova, J., Sramkova, K., Konvalinka, J., Majer, P., and Sacha, P. (2015) Design of Highly Potent Urea-Based, Exosite-Binding Inhibitors Selective for Glutamate Carboxypeptidase II. *Journal of medicinal chemistry* 58, 4357-63;

Weineisen, M., Simecek, J., Schottelius, M., Schwaiger, M., and Wester, H.-J. (2014) Synthesis and preclinical evaluation of DOTAGA-conjugated PSMA ligands for functional imaging and endoradiotherapy of prostate cancer. *EJNMMI Res* 4, 1-15.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of Formula (I):

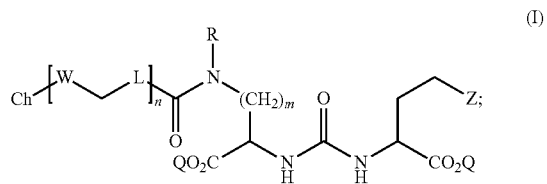

wherein:
Z is tetrazole or $CO_2Q$;
Q is H or a protecting group;
m is an integer selected from the group consisting of 1, 2, 3, 4, and 5;
R is $-CH_2-R^1$;
$R^1$ is:

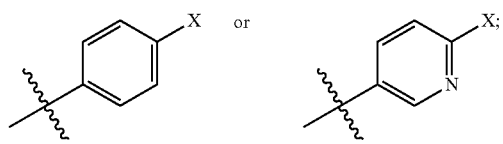

wherein each X is independently Br or I;
L consists of a $C_1$-$C_6$ alkylene linker;
W is —(C=O)—$NR^2$;
$R^2$ is H or a $C_1$-$C_4$ alkyl;
n is 1;
Ch is a chelating agent having a structure of:

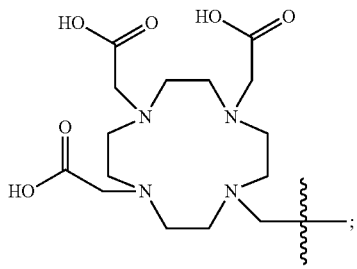 [SMILES: *CN1CCN(CC(=O)O)CCN(CC(=O)O)CCN(CC(=O)O)CC1]

that can comprise a metal or a radiometal;
and pharmaceutically acceptable salts thereof.

2. The compound of claim 1, wherein the chelating agent comprises a metal selected from the group consisting of: Y, Lu, Tc, Zr, In, Sm, Re, Cu, Pb, Ac, Bi, Al, Ga, Re, Ho and Sc.

3. The compound of claim 2, wherein the metal is a radiometal and is selected from the group consisting of: $^{68}$Ga, $^{64}$Cu, $^{86}$Y, $^{90}$Y, $^{89}$Zr, $^{99m}$Tc, $^{177}$Lu, $^{153}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

4. The compound of claim 1, wherein the compound of Formula (I) is selected from the group consisting of:

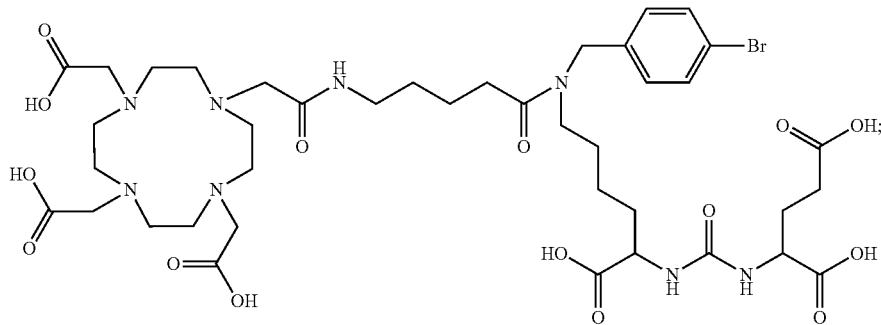 [SMILES: O=C(O)CCC(NC(=O)NC(CCCCN(Cc1ccc(Br)cc1)C(=O)CCCCNC(=O)CN1CCN(CC(=O)O)CCN(CC(=O)O)CCN(CC(=O)O)CC1)C(=O)O)C(=O)O]

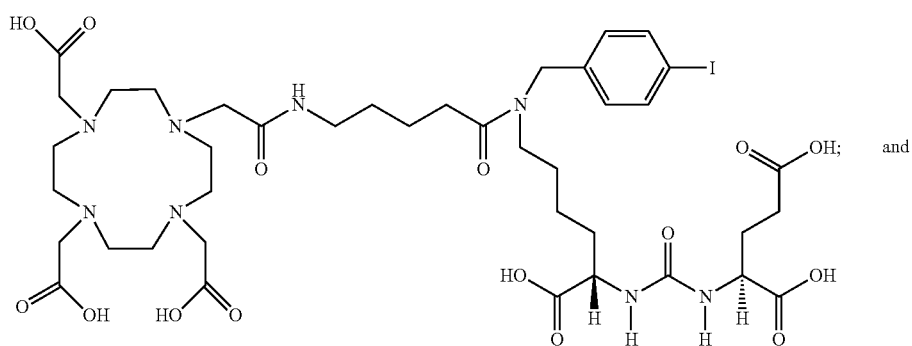

and

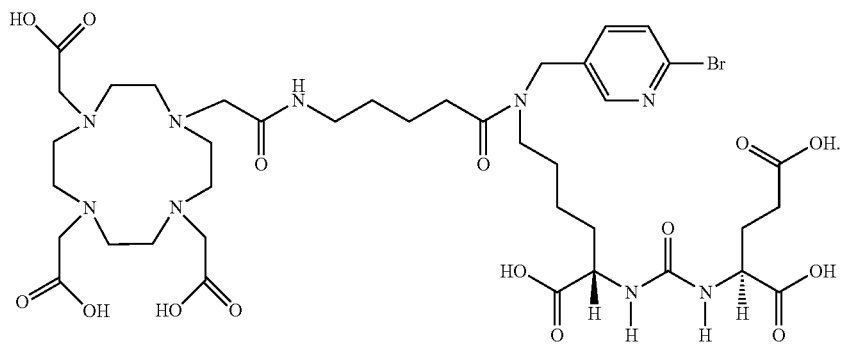

P2

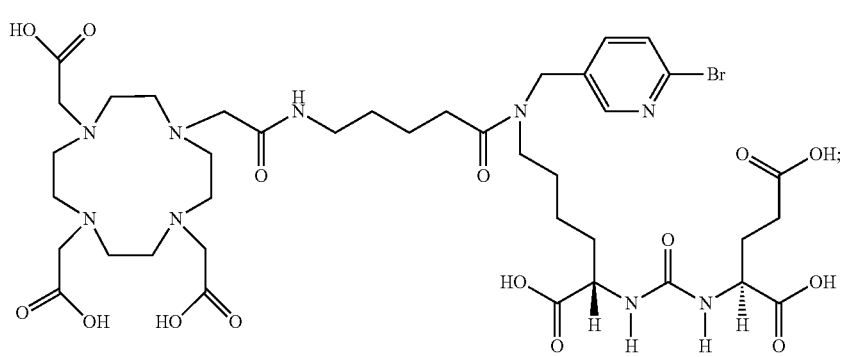

P2

5. A method for treating one or more PSMA expressing tumors or cells, the method comprising contacting the one or more PSMA expressing tumors or cells with an effective amount of a compound of formula (I), the compound of formula (I) comprising:

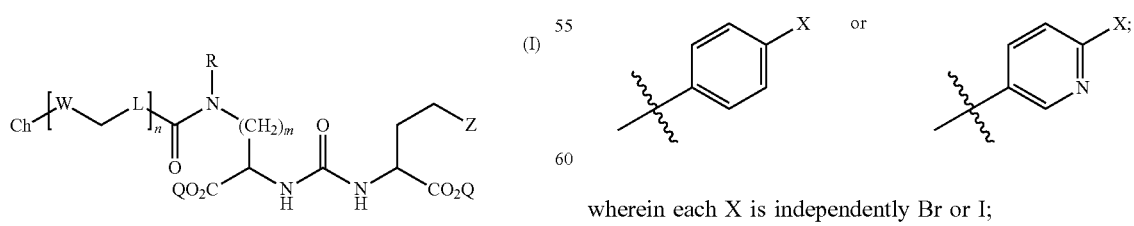

(I)

wherein:

Z is tetrazole or $CO_2Q$;

Q is H or a protecting group;

m is an integer selected from the group consisting of 1,2,3,4, and 5;

R is —$CH_2$—$R^1$;

$R^1$ is wherein each X is independently Br or I;

L consists of a $C_1$-$C_6$ alkylene linker;

W is (C=O)—$NR^2$;

$R^2$ is H or a $C_1$-$C_4$ alkyl;

n is 1;

Ch is a chelating agent having a structure of:

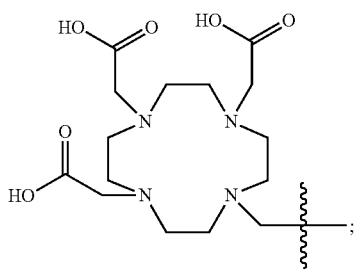 [SMILES: *CN1CCN(CC(=O)O)CCN(CC(=O)O)CCN(CC(=O)O)CC1]

that comprises a radiometal suitable for radiotherapy;

and pharmaceutically acceptable salts thereof.

6. The method of claim 5, wherein the radiometal is selected from the group consisting of: $^{90}$Y, $^{177}$Lu, $^{211}$At, $^{111}$In, $^{153}$Sm, $^{186}$Re, $^{188}$Re, $^{67}$Cu, $^{212}$Pb, $^{225}$Ac, $^{213}$Bi, $^{212}$Bi, $^{212}$Pb, and $^{67}$Ga.

7. The method of claim 5, wherein the compound is selected from the group consisting of:

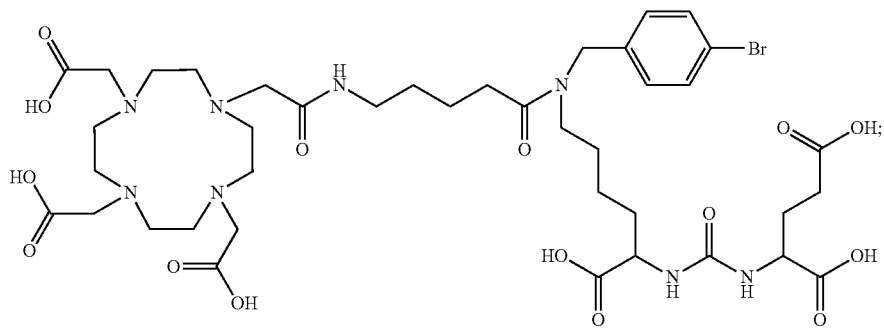 [SMILES: O=C(O)CCC(NC(=O)NC(CCCCN(Cc1ccc(Br)cc1)C(=O)CCCCNC(=O)CN1CCN(CC(=O)O)CCN(CC(=O)O)CCN(CC(=O)O)CC1)C(=O)O)C(=O)O]

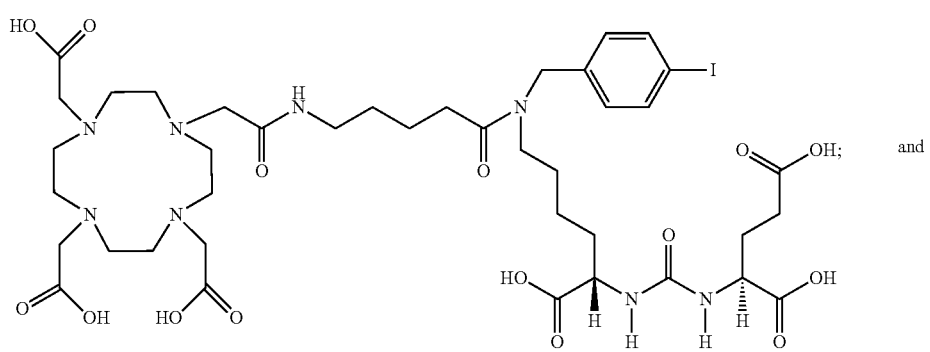

P2 and

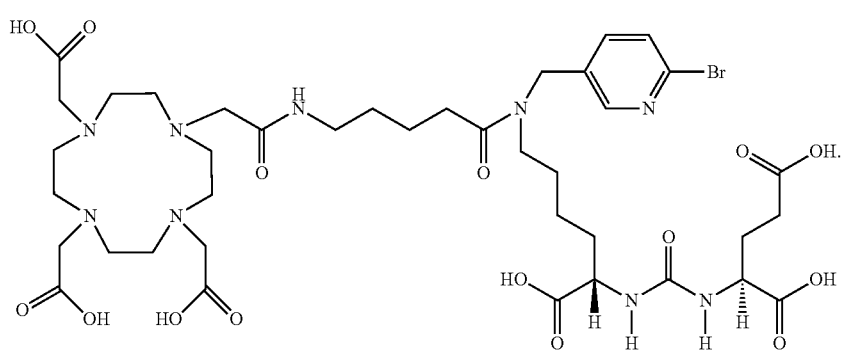

P2

-continued

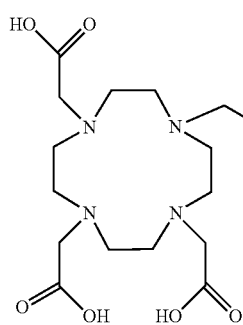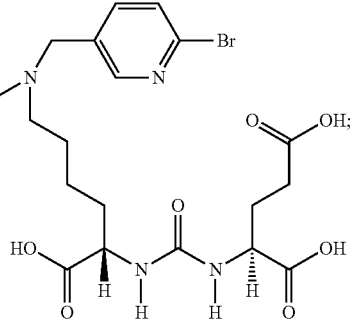

8. The method of claim 5, wherein the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

9. The method of claim 5, wherein the one or more PSMA-expressing tumor or cell is a prostate tumor or cell.

10. The method of claim 5, wherein the one or more PSMA-expressing tumor or cell is in vitro, in vivo, or ex vivo.

11. The method of claim 5, wherein the one or more PSMA-expressing tumor or cell is present in a subject.

12. The method of claim 11, wherein the subject is human.

13. The method of claim 5, wherein the method results in inhibition of the tumor growth.

14. A compound of Formula (I):

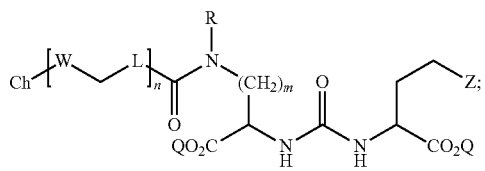

wherein:
Z is $CO_2Q$;
Q is H;
m is 4;
R is —$CH_2$—$R^1$;
$R^1$ is

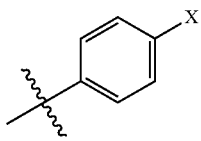

wherein X is Br;
L consists a of a $C_1$-$C_6$ alkylene linker;
W is —(C=O)—$NR^2$—;
$R^2$ is H;
n is 1;
Ch is a chelating agent having a structure of:

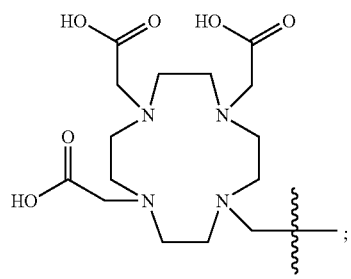 [SMILES: *CN1CCN(CC(=O)O)CCN(CC(=O)O)CCN(CC(=O)O)CC1]

that comprises the radiometal $^{177}$Lu;
and pharmaceutically acceptable salts thereof.

* * * * *